(12) United States Patent
Lucas et al.

(10) Patent No.: US 7,189,892 B2
(45) Date of Patent: Mar. 13, 2007

(54) NUCLEIC ACIDS ENCODING PHLOEM SMALL RNA-BINDING PROTEINS AND TRANSGENIC PLANTS COMPRISING THEM

(75) Inventors: William J. Lucas, Davis, CA (US); Byung-Chun Yoo, Newark, DE (US); Tony J. Lough, Auckland (NZ); Erika Varkonyi-Gasic, Auckland (NZ)

(73) Assignees: The Regents of the University of California, Oakland, CA (US); Agrigenesis Biosciences Limited, Auckland (NZ)

( * ) Notice: Subject to any disclaimer, the term of this patent is extended or adjusted under 35 U.S.C. 154(b) by 24 days.

(21) Appl. No.: 10/871,841

(22) Filed: Jun. 17, 2004

(65) Prior Publication Data

US 2005/0050588 A1    Mar. 3, 2005

Related U.S. Application Data

(60) Provisional application No. 60/487,358, filed on Jul. 14, 2003.

(51) Int. Cl.
| | |
|---|---|
| *C12N 15/09* | (2006.01) |
| *C12N 15/29* | (2006.01) |
| *C12N 15/82* | (2006.01) |
| *A01H 5/00* | (2006.01) |

(52) U.S. Cl. .................. 800/278; 800/298; 536/23.6
(58) Field of Classification Search ............... 800/278, 800/298, 286, 295; 435/468; 536/23.6
See application file for complete search history.

(56) References Cited

OTHER PUBLICATIONS

Aoki, Koh et al., (2002) "A Subclass of Plant Heat Shock Cognate 70 Chaperones Carries A Motif That Facilitates Trafficking Through Plasmodesmata" *PNAS*, 99(25):16342-16347.
Atkins, C. A. (1999) Spontaneous Phloem Exudation Accompanying Abscission in *Lupinus mutabilis* (Sweet) *J. Exp. Bot.* 50, 805-812.
Balachandran, S. et al., (1997) Phloem Sap Proteins from *Cucurbita maxima* and *Ricinus communis* Have the Capacity to Traffic Cell to Cell through Plasmodesmata *Proc. Natl. Acad. Sci. U.S.A.* 94, 14150-14155.
Bernstein, E. et al., (2001) "Role for a Bidentate Ribonuclease in the Initiation Step of RNA Interference" *Nature* 409, 363-366.
Carrington, J. C. et al., (1996) "Cell to Cell and Long Distance Transport of Viruses in Plants" *Plant Cell* 8, 1669-1681.
Dalmay, T. et al., (2000) "An RNA-Dependent RNA Polymerase Gene in Arabidopsis is Required for Posttranscriptional Gene Silencing Mediated by a Transgene but not by a Virus" *Cell* 101, 543-553.
Dalmay, T. et al., (2001) "SDE3 Encodes an RNA Helicase Required for Posttranscriptional Gene Silencing in Arabidopsis" *EMBO J.* 20(8): 2069-2077.
Di Serio, F. et al., (2001) "Sense- and Antisense-Mediated Gene Silencing in Tobacco is Inhibited by the Same Viral Suppressors and is associated With Accumulation of Small RNAs" *Proc. Natl. Acad. Sci.* 98(11): 6506-6510.
Elbashir, M. et al., (2002) "Analysis of Gene Function in Somatic Mammalian Cells Using Small Interfering RNAs" *Methods* 26, 199-213.
Elbashir, S. M. (2001) "RNA Interference is Mediated by 21 and 22-Nucleotide RNAs" *Genes Dev.* 15, 188-200.
Fagard, M. et al., (2000) (Trans) Gene Silencing in Plants: How Many Mechanisms? *Annu Rev. Plant Physiol. Plant Mol. Biol.* 51, 167-194.
Fire, et al., (1998) "Potent and Specific Genetic Interference by Double-Stranded RNA in *Caenorhabditis elegans*" *Nature* 391, 806-811.
Gilbertson, R. L. et al., (1996) How Do Viruses Traffic on the 'Vascular Highway'? *Trends Plant Sci.* 1(8):260-268.
Gou, H. S. et al., (2002) "A Viral Protein Inhibits the Long Range Signaling Activity of the Gene Silencing Signal" *EMBO J.* 21(3):398-407.
Hamilton, A. J. et al., (2002) Two Classes of Short Interfering RNA in RNA Silencing *EMBO J.* 21(17): 4671-4679.
Hamilton, A. J. et al., (1999) "A Species of Small Antisense RNA in Posttranscriptional Gene Silencing in Plants" *Science* 286, 950-952.
Hammond, S. M. et al., (2000) "An RNA Directed Nuclease Meditates Post-Transcriptional Gene Silencing in *Drosophila* Cells" *Nature* 404, 293-296.
Hannon, G. J. (2002) "RNA Interference" *Nature* 418, 244-251.
Hartono, S. J. (2003) "Nucleotide Sequence and Genome Organization of Cucumber Yellows Virus, a Member of the Genus Crinivirus"*Gen. Virol.* 84, 1007-1012.
Havey, M. J. et al., (1998) Differential Transmission of the *Cucumis* Organellar Genomes *Theor. Applied Genet.* 97, 122-128.
Haywood, V. et al., (2002) "Plasmosdesmata: Pathways for Protein and Ribonucleoprotein Signaling" *Plant Cell* 14, S303-S325.
Hutvagner, G. et al., (2001) "A Cellular Function for the RNA Interference Enzyme Dicer in the Maturation of the *let-7* Small Temporal RNA" *Science* 293, 834-838.
Hutvagner, G. et al., (2002) "A microRNA in a Multiple Turnover RNAi Enzyme Complex" *Science* 297, 2056-2060.

(Continued)

*Primary Examiner*—Medina A. Ibrahim
(74) *Attorney, Agent, or Firm*—Morrison & Foerster LLP

(57) ABSTRACT

The present invention provides a polynucleotide sequence encoding a component of the protein machinery involved in small RNA trafficking, *Cucurbita maxima* phloem small RNA-binding protein (CmPSRB 1), and the corresponding polypeptide sequence. The invention also provides genetic constructs and transgenic plants comprising the polynucleotide sequence encoding a phloem small RNA-binding protein to alter (e.g., prevent, reduce or elevate) non-cell autonomous signaling events in the plants involving small RNA metabolism. These signaling events are involved in a broad spectrum of plant physiological and biochemical processes, including, for example, systemic resistance to pathogens, responses to environmental stresses, e.g., heat, drought, salinity, and systemic gene silencing (e.g., viral infections).

8 Claims, 11 Drawing Sheets

OTHER PUBLICATIONS

Jackson, D. (2001) "The Long and the Short of it: Signaling Development through Plasmodesmata" *Plant Cell* 13, 2569-2571.

Jeschke, W. D. et al., (1991) "Cation and Chloride Partitioing through Xylem and Phloem within the Whole Plant *Ricinus communis L.* Under Conditions of Salt Stress" *J. Exp. Bot.* 42(242): 1105-1116.

Jorgensen, R. A. et al., (1998) "An RNA-Based Information Superhighway in Plants" *Science* 279 (5356): 1486-1487.

Kim, J. Y. et al., (2001) "Development Changes Due to Long-Distance Movement of a Homeobox Fusion Transcript in Tomato" *Science* 293, 287-289.

Kim, M. et al., (2002) "Intercellular Trafficking of a KNOTTED 1 Green Fluorescent Fusion in the Leaf and Shoot meristem of *Arabidopsis*" *Proc. Natl. Acad. Sci. USA* 99(6): 4103-4108.

Kovalchuk, I. et al., (2003) "Pathogen-Induced Systemic Plant Signal Triggers DNA Rearrangements" *Nature* 423, 760-762.

Llave, C. et al., (2002) "Endogenous and Silencing Associated Small RNAs in Plants" *Plant Cell* 14, 1605-1619.

Llave, C. et al., (2002) "Cleavage of Scarecrow-Like mRNA Targets Directed by a Class of *Arabidopsis* miRNA" *Science* 297, 2053-2056.

Lucas, W. J. et al., (1995) "Selective Trafficking of KNOTTED1 Homeodomain Protein and its mRNA Through Plasmodesmata" *Science* 270, 1980-1983.

Lucas, W. J. et al., (2001) "RNA as a Long-Distance Information Macromolecule in Plants" *Nat. Rev. Mol. Cell Biol.* 2, 849-857.

Mallory, A. C. et al., (2001) "HC-Pro Suppression of Transgene Silencing Eliminates the Small RNAs but not Transgene Methylation or the Mobile Signal" *Plant Cell* 13, 571-583.

Matzke, M. et al., (2001) "RNA: Guiding Gene Silencing" *Science* 293, 1080-1083.

Mlotshwa, S. et al., (2002) "RNA Silencing and the Mobile Silencing Signal" *Plant Cell* 14, S289-S301.

Mourrain, P. et al., (2000) "*Arabidopsis* SGS2 and SGS3 Genes are Required for Posttranscriptional Gene Silencing and Natural Virus Resistance" *Cell* 101, 533-542.

Nakajima, K. et al., (2001) "Intercellular Movement of the Putative Transcription Factor SHR in Root Patterning" *Nature* 413, 307-311.

Olsen, P. H. et al., (1999) "The lin-4 Regulatory RNA Controls Developmental Timing in *Caenorhabditis elegans* by Blocking LIN-14 Protein Synthesis after the Initiation of Translation" *Dev. Biol.* 216, 671-680.

Palauqui, J.-C et al., (1997) "Systematic Acquired Silencing: Transgene-Specific Post-Transcriptional Silencing is Transmitted by Grafting from Silenced Stocks to non-Silenced Scions" *EMBO J* 16(15): 4738-4745.

Pang, S. Z. et al., (2000) "Resistance to Squash Mosaic Comovirus in Transgenic Squash Plants expressing its Coat Protein Genes" *Mol. Breeding* 6, 87-93.

Reinhart, B. J. et al., (2002) "MicroRNAs in Plants" *Genes Dev.* 16, 1616-1626.

Robards, A. W. et al., (1990) "Plasmodesmata" *Annu Rev. Plant Phys. Plant Mol. Biol.* 41, 369-419.

Roignant, et al., (2003) "Absence of Transitive and Systematic Pathways Allows Cell-Specific and Isoform-Specific RNAi in *Drosophila*" *RNA* 9, 299-309.

Rojas, M. R. et al., (1997) "Capsid Protein and Helper Component-Proteinase Function as Potyvirus Cell-to-Cell Movement Proteins" *Virology* 237, 283-295.

Ruiz-Medrano, R. (1999) "Phloem Long Distance Transport of CmNACP mRNA: Implications for Supracellular Regulations in Plants" *Development* 126, 4405-4419.

Schiefelbein, J. (2003) "Cell-Fate Specification in the Epidermis: A Common Patterning Mechanism in the Root and Shoot" *Curr. Opin. Plant Biol.* 6, 74-78.

Sessions, A. et al., (2000) "Cell—Cell Signaling and Movement by the Floral Transcription Factors LEAFY and APETALA 1" *Science* 289, 779-781.

Sijen, T. et al., (2001) "On the Role of RNA Amplification in dsRNA-Triggered Gene Silencing" *Cell* 107, 465-476.

Tang, G. et al., (2003) "A Biochemical Framework for RNA Silencing in Plants" *Genes Dev.* 17, 49-63.

van Bel, A. J. E. (2003) "The Phloem, A Miracle of Ingenuity" *Plant Cell Environ.* 26, 125-149.

Vance, V. et al., (2001) "RNA Silencing in Plants—Defense and Counterdefense" *Science* 292, 2277-2280.

Voinnet, O. et al., (1998) "Systematic Spread of Sequence-Specific Transgene RNA Degradation in Plants is Initiated by Localized Introduction of Ectopic Promoterless DNA" *Cell* 95, 177-187.

Voinnet, O. (2001) "RNA Silencing as a Plant Immune System Against Viruses" *Trends Genet.* 17(8):449-459.

Volpe, T. A. et al., (2002) "Regulation of Heterochromatic Silencing and Histone H3 Lysine-9 Methylation by RNAi" *Science* 297, 1833-1837.

Wada, T. et al., (2002) "Role of a Positive Regulator of Root Hair Development, CAPRICE, in *Arabidopsis* Root Epidermal Cell Differentiation" *Development* 129, 5409-5419.

Winston, W. M. et al., (2002) Systemic RNAi in *C. elegans* Requires the Putative Transmembrane Protein SID-1 *Science* 295, 2456-2459.

Wu, X. et al., (2002) "Signaling in Plants by Intercellular RNA and Protein Movement" *Genes Dev.* 16, 151-158.

Xoconostle-Cazares, B. et al., (1999) "Plant Paralog to Viral Movement Protein that Potentiates Transport of mRNA into the Phloem" *Science* 283, 94-98.

Yoo, B.-C. et al., (2002) "Analysis of the Complexity of Protein Kinase within the Phloem Sieve Tube System" *J. Biol. Chem.* 277, 15325-15332.

Zambryski, P. et al., (2000) "Plasmodesmata: Gatekeepers for Cell-to-Cell Transport of Developmental Signals in Plants" *Annu. Rev. Cell Dev. Biol.* 16, 393-421.

Zamore, P. D. et al., (2000) "RNAi: Double-Stranded RNA Directs the ATP-Dependent Cleavage of mRNA at 21 to 23 Nucleotide Intervals" *Cell* 101, 25-33.

Figure 5
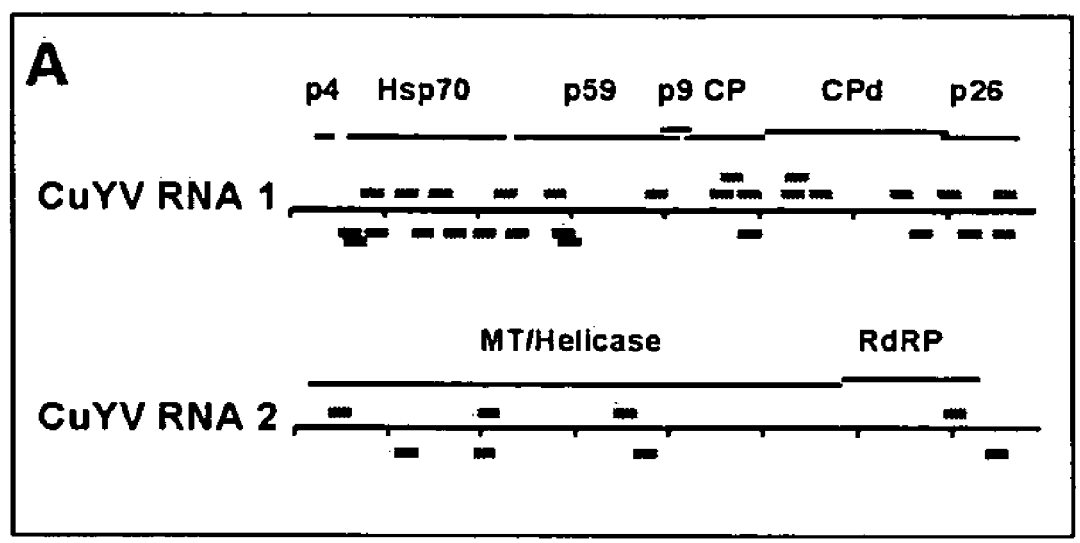
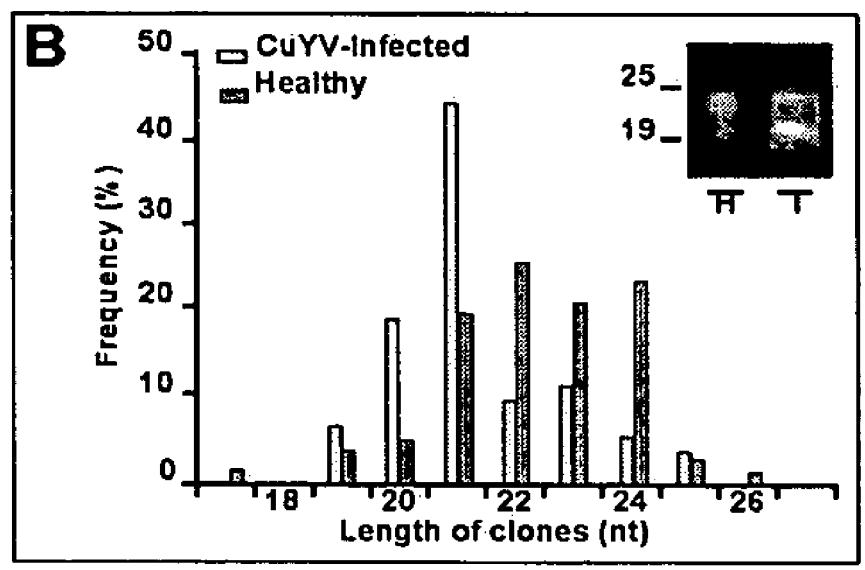

Figure 8

A  Purification of phloem CmPSRB1

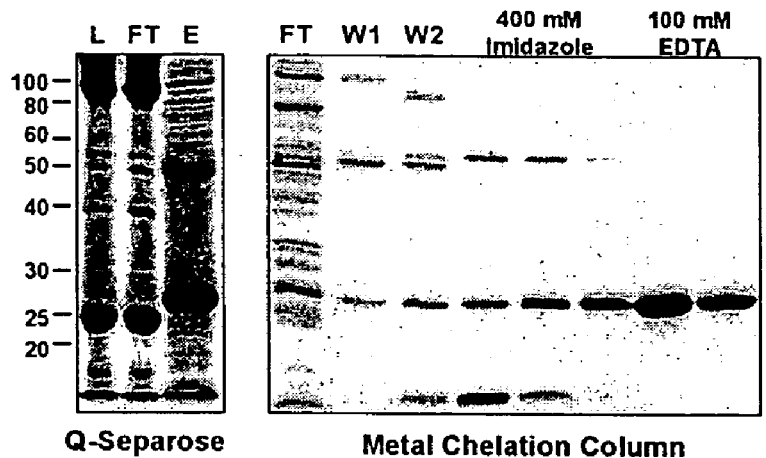

Q-Separose    Metal Chelation Column

B  Amino acid sequence of CmPSRB1

```
  1  MASFQCNKPAERSHHQRHDQCHQEHQHHHG
 31  HGPAGGHGHGPAWGHGHGPSGGHGCGPSGG
 61  HGHGPSGGHGHGPSGGHGHGPAWGHGHGPS
 91  GGHGCGPSGGHGHGPSGGHGHGPSGGHGHG
121  PSGGHGHGPSGGHGHGPAWGHGHGPSGGHG
151  CGPAGGHGHGPAGGQGHCQPANPNVGHCQP
181  ANPNVGHCQPASPNVGHHSDSSDSDNDCRR
211  GQH
```

C  Purification of R-CmPSRB1

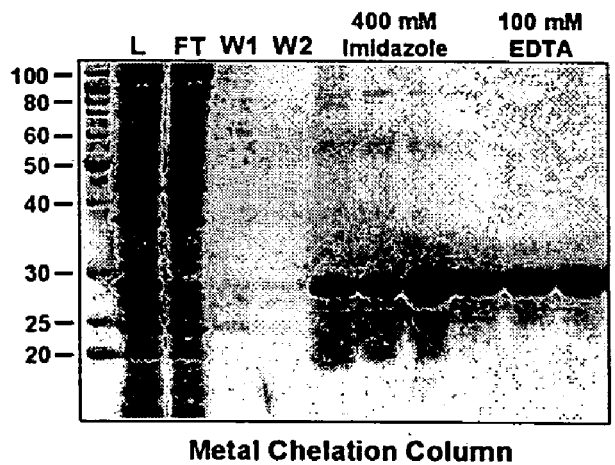

Metal Chelation Column

NUCLEIC ACIDS ENCODING PHLOEM SMALL RNA-BINDING PROTEINS AND TRANSGENIC PLANTS COMPRISING THEM

CROSS-REFERENCE TO RELATED APPLICATIONS

This application claims the benefit of U.S. Provisional Patent Application Ser. No. 60/487,358 filed Jul. 14, 2003, the disclosure of which is incorporated herein by reference in its entirety.

GOVERNMENT RIGHTS

This invention was made with Government support under Grant (or Contract) No. DE-FG03-94ER20134, awarded by the Department of Energy. The Government has certain rights in this invention.

FIELD OF THE INVENTION

This invention is in the field of plant molecular biology. In particular, this invention is in the field of small RNA signaling in plants.

BACKGROUND OF THE INVENTION

In eukaryotic organisms, a paradigm is emerging in which RNA functions as non-cell-autonomous signaling molecules (1–4). Full citations for the references are provided before the claims. In plants, a role for non-cell-autonomous RNA has been established in terms of systemic signaling associated both with RNA interference (RNAi) (1, 5–7) and development (8–10). Plasmodesmata (PD), the intercellular organelles of the plant kingdom (11), serve as the conduit through which proteins and RNA-protein complexes move, cell to cell, to exert supracellular control (11–15). The vascular system, and specifically the specialized cell-types of the phloem, provides the pathway for the long-distance translocation of non-cell-autonomous RNA-protein complexes, to distantly located tissues and organs (1, 5, 8–10). Delivery of such informational macromolecules into and out of the phloem translocation stream appears to occur through PD (10, 16).

The protein machinery involved in RNAi is under intense investigation (17). It is now evident that an RNase-III type enzyme, termed Dicer (18), and plant homologs of Dicer are pivotal to this process. Dicer binds and cleaves double-stranded (ds)RNA into 21–25 nt dsRNA species (19). These small RNA cleavage products then function as sequence-specific small interfering RNA (siRNA) or micro-RNA (miRNA) to mediate changes in gene expression by diverse mechanisms, including targeted degradation of gene transcripts, methylation and translational control (20, 21, 32). The cell-to-cell and systemic spread of RNAi is considered to occur through PD (3, 6) and the phloem (1, 3, 5–7), respectively; however, the RNA species and underlying mechanism of trafficking remain to be elucidated (7). There is thus a tremendous need both to better understand the underlying mechanism of RNA trafficking and to apply this knowledge to plant modification and improvement

SUMMARY OF THE INVENTION

The present invention provides an isolated and purified plant polynucleotide sequence encoding a phloem small RNA binding protein, which we refer to generically as PSRB or PSRB1. An exemplary amino acid sequence is shown in FIG. 8B. This protein, and its orthologs in other plant species, is believed essential for non-cell autonomous signalling processes involving small RNA. The protein binds specifically to, and mediates the cell-to-cell and long distance (systemic) trafficking of small RNA molecules. The invention encompasses the coding sequences and their complements, and sequences that hybridize under high stringency conditions to sequences that encode the protein sequence depicted in FIG. 8B. Variants and homologs of the inventive polynucleotide sequence which encode proteins that bind specifically to, and mediate the cell-to-cell and long distance (systemic) trafficking of small RNAs are intended to be covered by in this invention.

The invention also provides genetic constructs comprising the polynucleotide sequences encoding a PSRB1 protein, for transforming a host organism, preferably a plant, or a portion or cell thereof. It is expected that any biological process involving small RNA acting non-cell autonomously can be manipulated by altering the expression of PSRB1, for example, by knockout, overexpression or expression of dominant negative forms of the protein in plants.

The invention also provides oligonucleotide probes and primers for hybridization-based and/or PCR-based detection, quantitation and/or amplification of PSRB1 polynucleotide sequences from genomic DNA, DNA libraries and plant tissues, e.g., plant vascular tissues, and expression profiling, e.g., in situ hybridization, microarray screening. In another aspect, the invention is directed to transgenic plants comprising a PSRB1 sequence, and portions, thereof, which contain altered levels and distribution of small RNAs, and changes in the profile of small RNA populations in plant tissues and phloem. The present invention is further directed to seed produced by the transgenic plants of the invention.

Methods are also provided for using these PSRB1 sequences and constructs to alter (e.g., prevent, reduce or elevate) non-cell autonomous signaling events in plants involving small RNA metabolism. These signaling events are involved in a broad spectrum of plant developmental, physiological and biochemical processes, including, for example, flowering, coordination of plant growth and development, systemic resistance to pathogens, responses to environmental stresses, e.g., heat, drought, salinity, systemic gene silencing (e.g., viral infections), biomass distribution, regulation of carbon metabolism and control of plant size and developmental timing and patterning.

The invention also provides isolated and purified PSRB polypeptides and methods of use. In one embodiment, the present invention is directed to isolated PHLOEM SMALL RNA-BINDING PROTEIN1 (PSRB1). PSRB1 can be isolated from any plant utilizing the procedures illustrated herein. The amino acid sequences of PSRB proteins from different plants will likely vary from each other. However, while the sequences will vary, their activity will be similar in that they all will exhibit RNA binding activity and will be expressed in the phloem of plants.

An exemplary PSRB1 sequence is the *Cucurbita maxima* PSRB1 sequence depicted in FIG. 8B. The DNA sequence is as follows:

```
  1 tctaatcttt  gcatccatgg  cgtctttcca  atgcaacaaa  ccggctgagc  gcagccacca    (SEQ ID NO: 1)
 61 ccagaggcac  gatcaatgcc  atcaggaaca  ccaacaccat  cacggccacg  gtccggcggg
121 gggtcacggc  cacggtccgg  cgtggggtca  cggccacggt  ccgtcggggg  gtcacggctg
181 cggtccgtcg  ggggtcacg   gccacggtcc  gtcgggggt   cacggccacg  gtccgtcggg
241 gggtcacggc  cacggtccgg  cgtggggtca  cggccacggt  ccgtcggggg  gtcacggctg
301 cggtccgtcg  ggggtcacg   gccacggtcc  gtcgggggt   cacggccacg  gtccgtcggg
361 gggtcacggc  cacggtccgt  cggggggtca  cggccacggt  ccgtcggggg  gtcatggcca
421 cggtccggcg  tggggtcacg  gccacggtcc  gtcgggggt   cacggctgcg  gtccggcggg
481 gggtcacggc  cacggtcctg  cggggggca   aggccactgc  cagccagcca  atcccaatgt
541 cggacactgc  cagccagcca  atcccaacgt  cggccactgc  cagccagcca  gtcccaatgt
601 cggccaccac  agcgacagca  gtgacagtga  caacgattgt  cgcagaggtc  agcactaaag
661 gaagaattgg  aaggaggaag  tggaagggta  cttgctagat  tgaagggaag  ggaatcagag
721 agtgcatcta  aactgctact  gatactccta  ctactaagta  ttcgagtgac  gcctaaaata
781 aataagacaa  tttataagac  accctaactt  tatctccttt  tccttctttc  aaataaagtt
841 tctgtattgc  taaaaaaaaa  aaaaaaaaaa The amino acid sequence as shown in FIG. 8B is:

1 MASFQCNKPAERSHHQRHDQCHQEHQHHHG                                            (SEQ ID NO: 2)
 31 HGPAGGHGHGPAWGHGHGPSGGHGCGPSGG
 61 HGHGPSGGHGHGPSGGHGHGPAWGHGHGPS
 91 GGHGCGPSGGHGHGPSGGHGHGPSGGHGHG
121 PSGGHGHGPSGGHGHGPAWGHGHGPSGGHG
151 CGPAGGHGHGPAGGQGHCQPANPNVGHCQP
181 ANPNVGHCQPASPNVGHHSDSSDSDNDCRR
211 GQH
```

The present invention is directed to proteins having sequences similar to *Cucurbita maxima* PSRB1 and exhibiting small RNA molecule binding activity. Such similar sequence may include amino acid substitutions, insertions and deletions so long as the protein retains its ability to bind small RNA molecules from plant cells. The present invention is further directed to homologs and orthologs of the *Cucurbita maxima* PSRB1 protein.

The PSRB1 polypeptides, and portions thereof which bind selectively to small RNA species, may be utilized for detection, isolation and characterization of candidate small RNA systemic signaling molecules. The polypeptides can also be used to screen for modulators of PSRB1 activity, e.g., agonists and antagonists of small RNA binding. Modulation of the activity of PSRB1 polypeptides may be useful for manipulating small RNA metabolism in plants. PSRB1 polypeptides may also be utilized to prepare antibodies for detection and PSRB1.

The present invention is further directed to phloem-mobile small RNA molecules isolated using the methods and compositions of the invention. These small RNA molecules can be over- or underexpressed in transgenic plants utilizing procedures well known in the art to identify their regulatory roles in plant growth and developmental processes.

One such small RNA molecules are identified, various bioinformatic analyses such as those illustrated herein permit identification of potential targets for these phloem small RNAs, including transposon-like genes. In addition to potential targets, developmental, physiological and biochemical responses can be identified. The small RNA molecules can be over- or under-expressed in transgenic plants utilizing procedures well known in the art to determine the physiological relevance and involvement of the molecules in plant developmental, biochemical and physiological processes. Thus, this invention establishes a foundation for understanding and modifying systemic signaling processes for plant modification and improvement.

BRIEF DESCRIPTION OF THE DRAWINGS

FIG. 5. Identification of RNA species in the phloem of virus infected pumpkin plants.

(A) Distribution of sense (green) and antisense (red) clones directed against both RNA 1 and RNA 2 of the Cucumber yellows closterovirus (CuYV) genome: Viral ORFs are as described (Hartono et al., 2003) and the presence of viral transcripts in the phloem sap was confirmed using standard protocols. (B) Size distribution of clones reflected in phloem small RNA databases prepared from healthy and CuYV-infected pumpkin plants; inset, small RNA populations present in healthy (H) and infected (I) phloem sap. Bioinformatic analysis revealed that 57% of the small RNA clones from CuYV-infected plants displayed 100% identity to this viral genome; majority 20–21 nt size-class. Database for healthy plants lacked any clones having sequence homology to CuYV.

Figure 6:
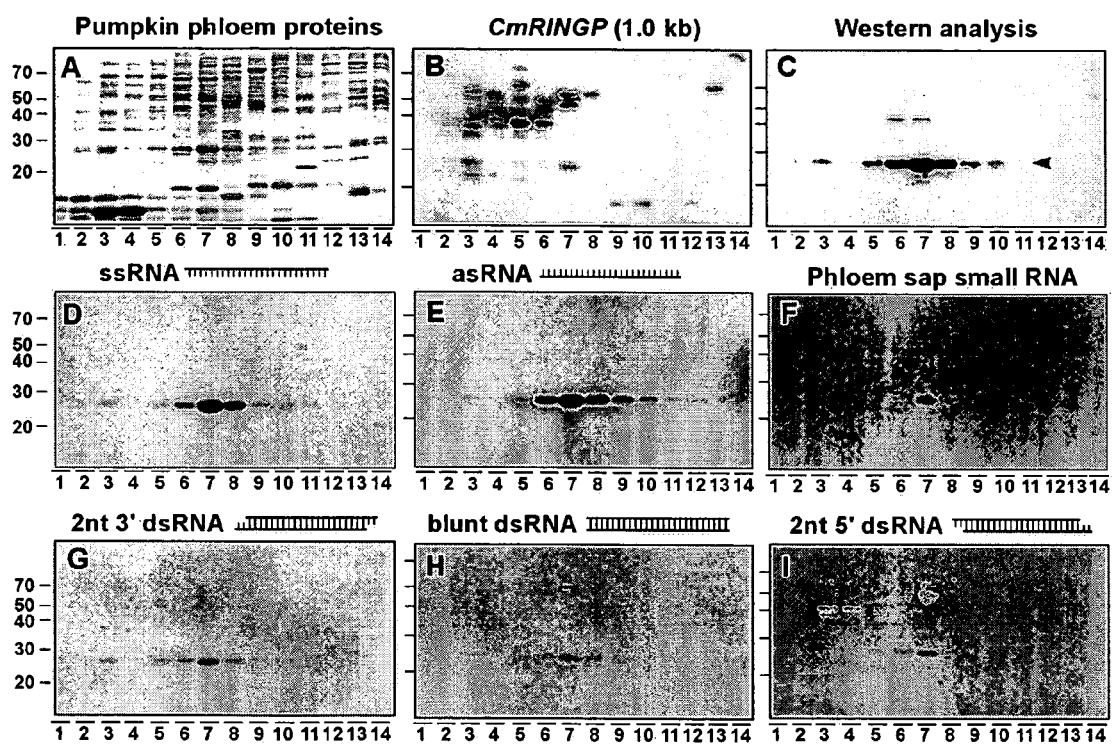

FIG 6. Identification of a phloem small RNA-binding protein present in pumpkin phloem sap. (A) Pumpkin phloem sap FPLC-fractionated proteins. (B) Northwestern assay performed on FPLC-fractionated proteins (A) using a CmRINGP-specific riboprobe (Ruiz-Medrano et al., 1999). Note the complement of phloem small RNA-binding proteins (PSRB) capable of recognizing this phloem-mobile mRNA. (C) Detection of a 27 kDa PSRB (dart) by a monoclonal anti-His$_6$ antibody. (D to I) Northwestern assays performed on FPLC-fractionated phloem proteins (A) using the indicated forms of small RNA riboprobes. Note that all probes bound to a 27 kDa PSRB.

Figure 7:
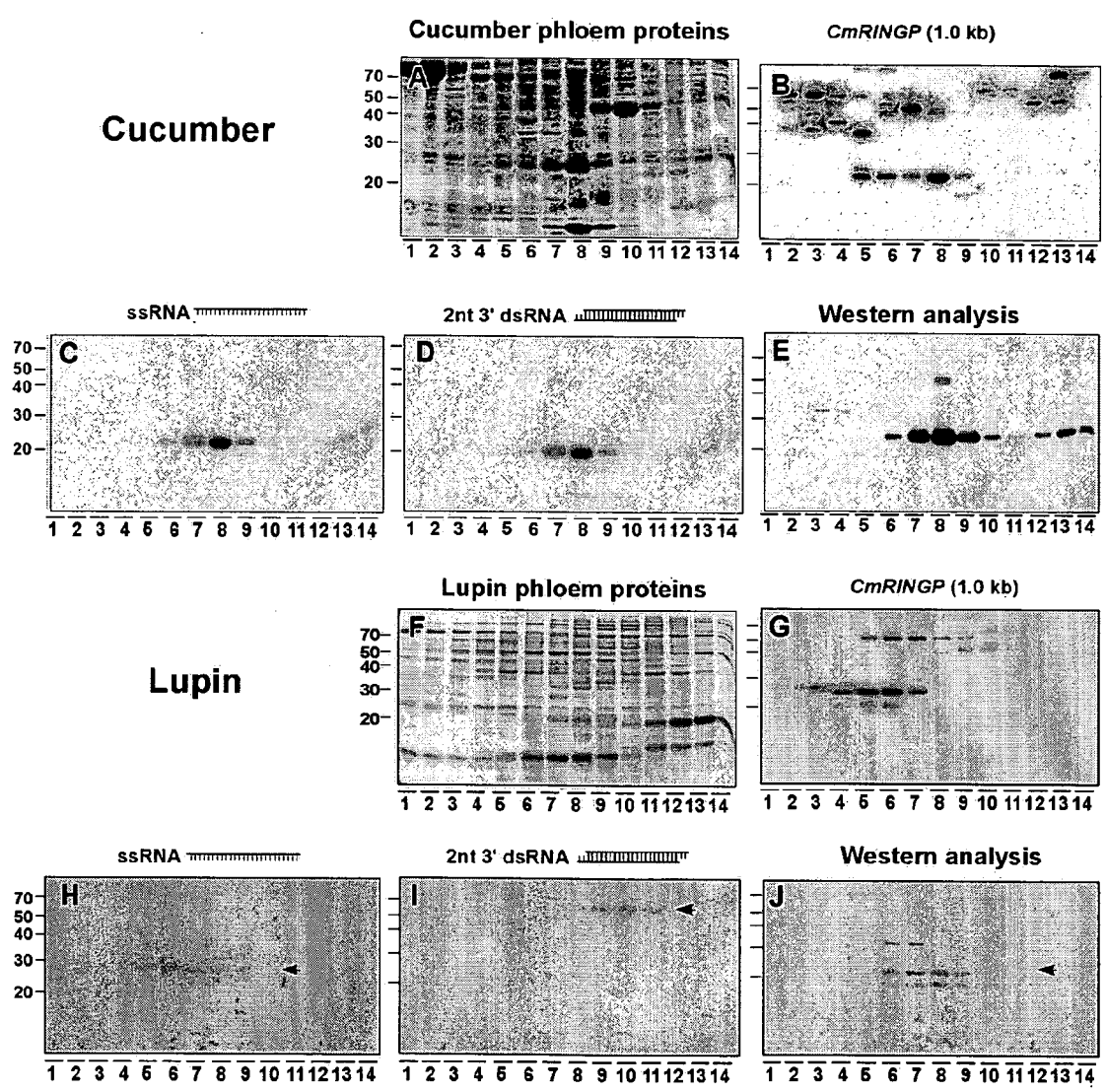

FIG. 7. Identification of a phloem small RNA-binding protein present in cucumber and lupin phloem sap. (A) Cucumber phloem sap FPLC-fractionated proteins. (B) Northwestern assay performed on FPLC-fractionated proteins (A) using a CmRINGP-specific riboprobe. Note the set of cucumber phloem small RNA-binding proteins (PSRB) capable of recognizing this pumpkin phloem-mobile mRNA. (C and D) Northwestern assays performed on FPLC-fractionated phloem proteins (A) using the indicated forms of small RNA riboprobes. Note that both probes bound to a single PSRB in the 27 kDa size range. (E) Detection of a 27 kDa PSRB by a monoclonal anti-His$_6$ antibody. (F) Lupin phloem sap FPLC-fractionated proteins. (G) Northwestern assay performed on FPLC-fractionated proteins (A) using a CmRINGP-specific riboprobe. Note the set of lupin PSRB capable of recognizing this pumpkin phloem-mobile mRNA. (H and I) Northwestern assays performed on FPLC-fractionated phloem proteins (F) using the indicated forms of small RNA riboprobes. Note that the ssRNA probe bound to a 27 kDa protein, whereas the dsRNA probe bound to a 55 kDa protein. (J) Detection of a 27 kDa PSRB by a monoclonal anti-His$_6$ antibody.

FIG. 8. Purification, cloning and expression of PSRB1. (A) Purification of the 27 kDa PSRB from pumpkin phloem sap using a combination of Q-Sepharose and metal chelation chromatography. Protein profiles contained within the anion-exchange fractions (L, loading; FT, flow-through; E, elution) were resolved by 10% SDS-PAGE (an equal volume [20 µl] was loaded for each fraction). Protein profiles for metal chelation resolved as above (FT, flow-through; W1/2, washes). (B) Conceptual translation of CmPSRB1 SEQ ID NO: 2 (GenBank accession number: AY326308) yielded a 20,454 Da protein. The predicted molecular mass was consistent with the value of 21,004 Da as determined by mass spectroscopy with the 27 kDa PSRB (A). (C) Purification of recombinant (R)-PSRB1 using metal chelation chromatography. Proteins from each step were resolved by 10% SDS-PAGE and visualized using GelCode Blue™.

Figure 9:
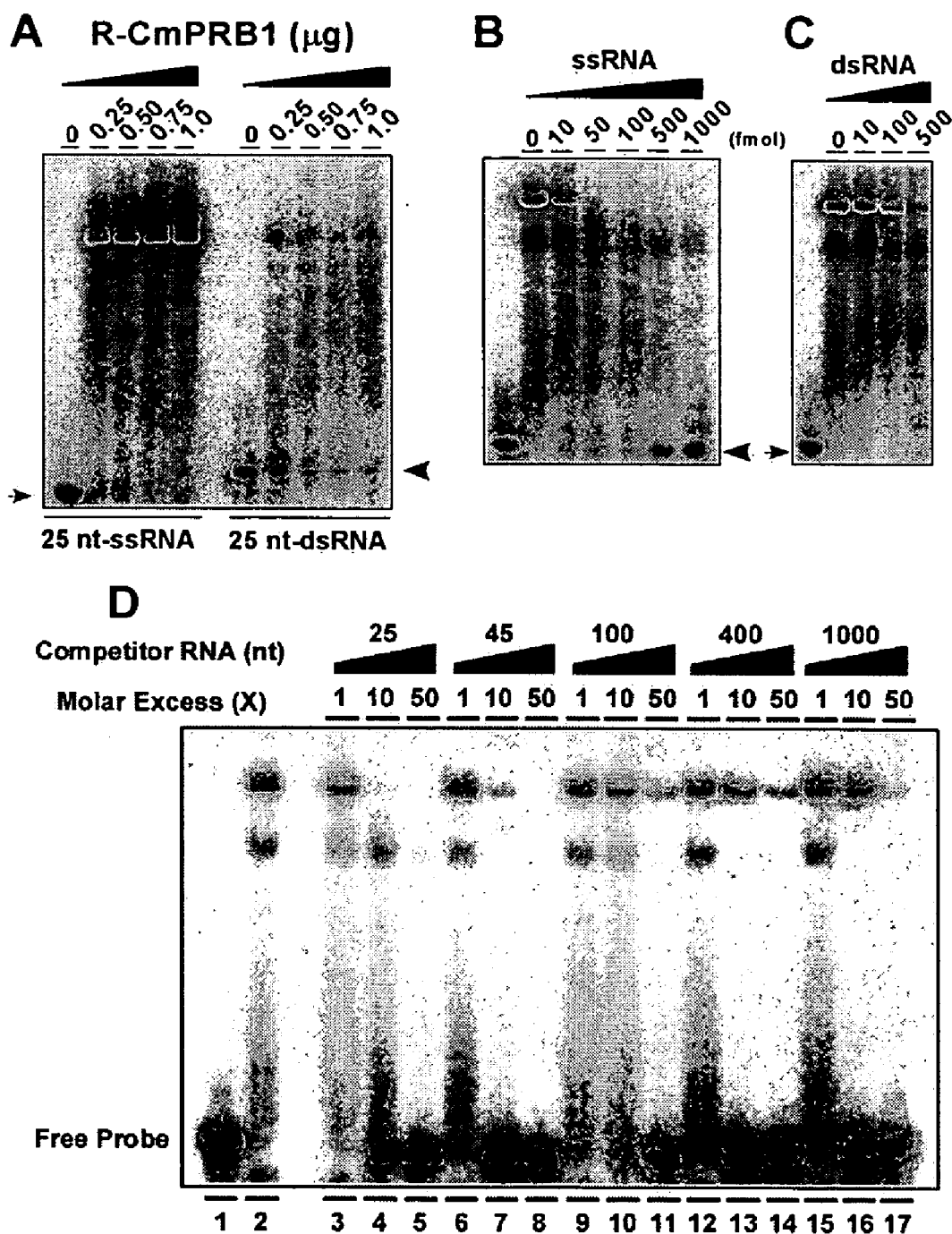

FIG. 9. Recombinant PSRB1 displayed form- and size-specific RNA binding properties. (A) Gel mobility-shift assays performed using R-PSRB1 and ss- and dsRNA probes (10 fmol). (B and C) Competition experiments carried out by pre-incubating R-PSRB1 (0.25 µg) with different concentrations of unlabeled ss- or dsRNA, respectively, followed by competition with $^{32}$P-labeled 25 nt ssRNA (10 fmol). R-PSRB1 dissociation constants ($K_d$) for 25 nt ssRNA and 2nt 3'25 nt dsRNA were $3.13\times10^{-8}$ M and $3.06\times10^{-5}$ M, respectively. (D) Competition experiments performed with ssRNA of various lengths. Purified R-PSRB1 (0.2 µg) was mixed with different amounts (molar excess indicated) of unlabeled 25 nt (lanes 3–5), 45 nt (lanes 6–8), 100 nt (lanes 9–11), 400 nt (lanes 12–14), or 1,000 nt (lanes 15–17) ssRNA molecules, followed by addition of radioactively labeled 25 nt ssRNA (10 fmol) probe. Complexes were analyzed by 5% PAGE. Lane 1, free probe only; lane 2, probe with R-PSRB1 only; Different length for each competitor RNA was taken into account in calculating the molar excess concentration. Note that R-PSRB1 bound preferentially to ssRNA molecules in the following order: 25 nt>45 nt>100 nt=400 nt=1000 nt.

Figure 10:
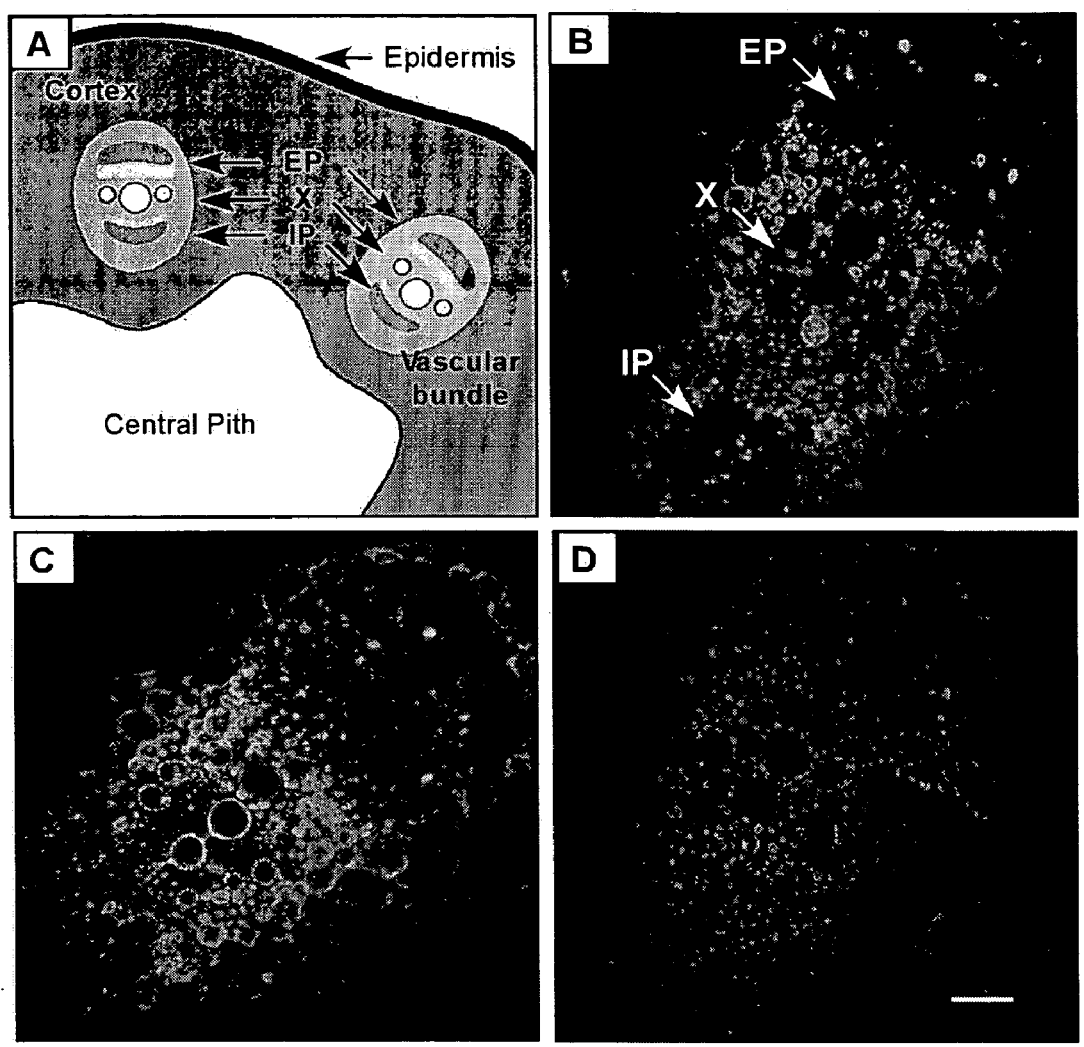

FIG. 10. In situ RT-PCR-based detection of CmPSRB1 transcripts in the vascular system. (A) Schematic transverse section of a portion of the pumpkin petiole. Vascular bundles are comprised of internal and external phloem (IP and EP, respectively) and xylem (X), with an intervening cambium (yellow). (B) Confocal laser scanning microscopy image of a pumpkin petiole (transverse section) demonstrating the presence of CmPSRB1 RNA (green signal represents incorporation of Alexa Fluor-labeled nucleotides) in phloem cells. (C) Equivalent cellular pattern detected for CmPP16 (Xoconostle-Cázares et al., 1999). (D) Negative control in which primers were omitted from the RT-PCR reaction mixture. Red fluorescence represents tissue autofluorescence and the green signal associated with the xylem reflects residual non-specific binding of unincorporated Alexa Fluor-labeled nucleotides. Scale bar in (D), 100 µm, common to (B), (C).

Figure 11:
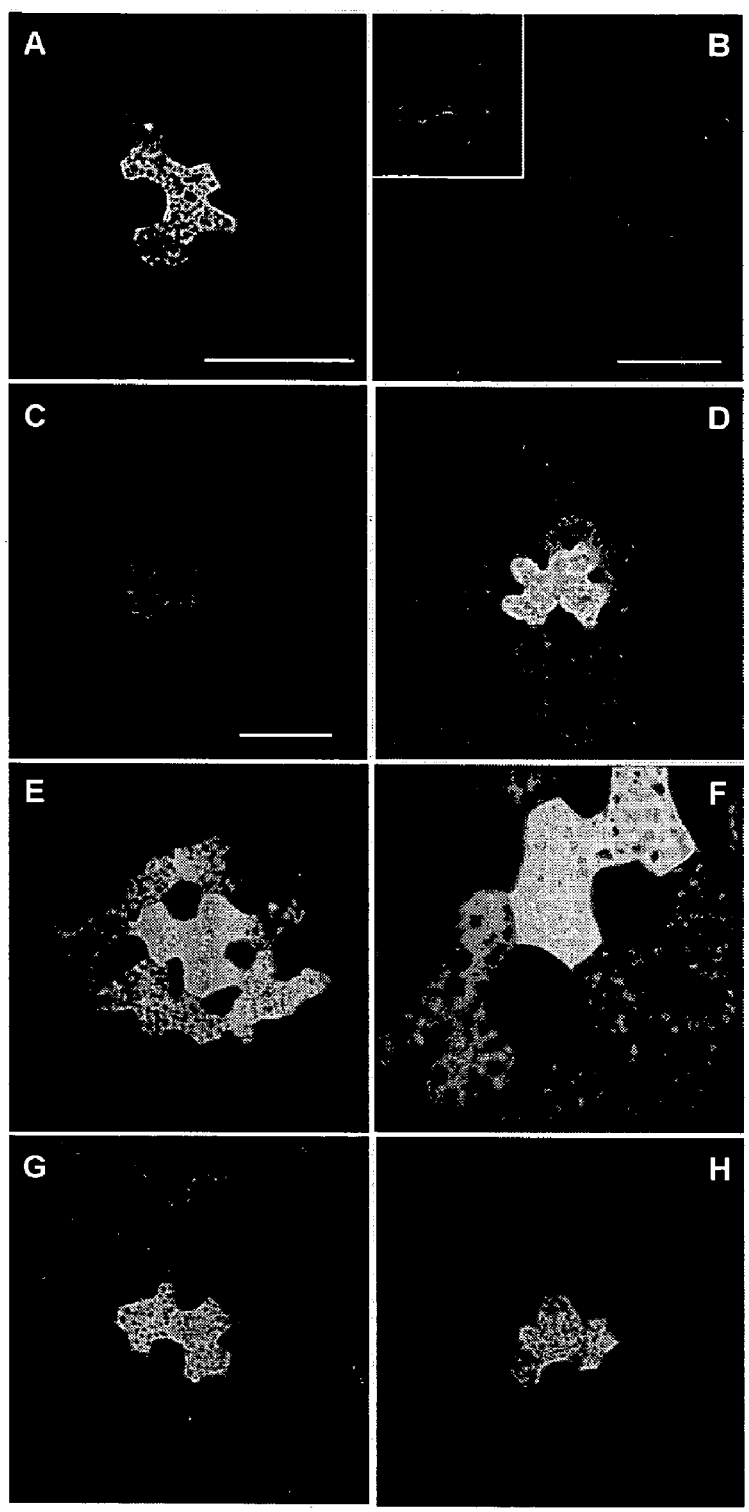

FIG. 11. PSRB1 can mediate form-specific cell-to-cell movement of small RNA. (A and B) Retention in the target cell of microinjected fluorescently labeled synthetic 25 nt ss- (A) or dskNA (B) (inset: low-magnification image of entire cell). (C and D) Cell-to-cell trafficking of KN1 through plasmodesmata potentiated extensive movement of FITC-labeled 20 kDa dextran (D, green signal), but the co-injected 25 nt ssRNA (red signal) was unable to diffuse out of the target cell (C). (E) Phloem-purified CmPSRB1 mediated cell-to-cell movement of co-injected fluorescently labeled (green) 25 nt ssRNA. (F) Equivalent experiment to that presented in (E) demonstrating movement of both 20 kDa dextran (green) and 25 nt ssRNA (red). Note the confinement of the fluorescent signals to neighboring cells (E and F). (G and H) Neither 25 nt dsRNA (G) nor 25 nt ssDNA (H) moved from the target cell when co-injected with phloem-purified CmPSRB1. All images were collected by confocal microscopy 20 min after injection into mesophyll cells in mature leaves of *Nicotiana benthamiana*. Scale bars, 100 µm; (C) common to (D)–(H).

DETAILED DESCRIPTION OF THE INVENTION

Before explaining at least one embodiment of the invention in detail, it is to be understood that the invention is not limited in its application to the details of construction and the arrangement of the components set forth in the following description. The invention is capable of other embodiments or of being practiced or carried out in various ways. Also, it is to be understood that the phraseology and terminology employed herein is for the purpose of description and should not be regarded as limiting.

Throughout this disclosure, various publications, patents and published patent specifications are referenced. The disclosures of these publications, patents and published patent specifications are hereby incorporated by reference into the present disclosure to more fully describe the state of the art to which this invention pertains. The practice of the present invention will employ, unless otherwise indicated, conventional techniques of plant breeding, immunology, molecular biology, microbiology, cell biology and recombinant DNA, which are within the skill of the art. See, e.g., Sambrook, Fritsch and Maniatis, MOLECULAR CLONING: A LABORATORY MANUAL, 2nd edition (1989); CURRENT PROTOCOLS IN MOLECULAR BIOLOGY [(F. M. Ausubel, et al. eds., (1987)]; Plant Breeding: Principles and Prospects (Plant Breeding, Vol 1) M. D. Hayward, N. O. Bosemark, I. Romagosa; Chapman & Hall, (1993.); Coligan, Dunn, Ploegh, Speicher and Wingfeld, eds. (1995) CURRENT PROTOCOLS IN PROTEIN SCIENCE (John Wiley & Sons, Inc.); the series METHODS IN ENZYMOLOGY (Academic Press, Inc.): PCR 2: A PRACTICAL APPROACH (M. J. MacPherson, B. D. Hames and G. R. Taylor eds. (1995)], Harlow and Lane, eds. (1988) ANTIBODIES, A LABORATORY MANUAL, and ANIMAL CELL CULTURE [R. I. Freshney, ed. (1987)].

Unless otherwise noted, technical terms are used according to conventional usage. Definitions of common terms in molecular biology may be found in Lewin, Genes V, published by Oxford University Press, 1994 (SBN 0-19-854287-9); Kendrew et al. (eds.), The Encyclopedia of Molecular Biology, published by Blackwell Science Ltd., 1994 (SBN 0-632-02182-9); and Robert A. Meyers (ed.), Molecular Biology and Biotechnology, a Comprehensive Desk Reference, published by VCH Publishers, Inc., 1995 (ISBN 1-56081-569-8); Ausubel et al. (1987) Current Protocols in Molecular Biology, Green Publishing; Sambrook et al. (1989) Molecular Cloning: A Laboratory Manual, Cold Spring Harbor, N.Y.

In order to facilitate review of the various embodiments of the invention, the following definitions are provided:

Phloem Small RNA Binding (PSRB) protein or polypeptide: A PSRB protein or PSRB polypeptide is a protein present in plant phloem that binds small RNA molecules and mediates the selective cell-to-cell movement of these molecules. PSRB and PSRB1 are used interchangeably herein. The present invention may be practiced using full length PSRB1 proteins as well as PSRB derived proteins that retain PSRB activity. For certain uses disclosed herein, the retention of small RNA—binding activity alone may be sufficient. Thus, PSRB derived proteins which retain PSRB biological activity include fragments of PSRB, generated either by chemical (e.g. enzymatic) digestion or genetic engineering means; chemically functionalized protein molecules obtained using exemplified protein or nucleic acid sequences as starting materials; protein sequence variants, such as for example, allelic variants and mutational variants, which may be produced by in vitro mutagenesis techniques, e.g., gene shuffling (Stemmer et al., 1994a, 1994b) and protein homologs and orthologs. Thus, the term "PSRB protein" encompasses full-length PSRB proteins, as well as such PSRB derived proteins that retain PSRB activity.

Promoter: A regulatory nucleic acid sequence, typically located upstream (5') of a gene or protein coding sequence that, in conjunction with various cellular proteins, is responsible for regulating the expression of the gene or protein coding sequence. The promoters suitable for use in the constructs of this invention are functional in plants and in host organisms used for expressing the inventive polynucleotides. Many plant promoters are publicly known. These include constitutive promoters, inducible promoters, tissue- and cell-specific promoters and developmentally-regulated promoters. Exemplary promoters and fusion promoters are described, e.g., in U.S. Pat. No. 6,717,034, which is herein incorporated by reference.

The promoters may be those normally associated with a transgene of interest, or heterologous promoters which are derived from genes of other plants, viruses, and plant pathogenic bacteria and fungi. Those skilled in the art will be able, without undue experimentation, to select promoters that are suitable for use in practicing the subject invention.

Sequence Identity: Sequences that show similarity to those described in this application can be identified by computer-based methods, using public domain sequence alignment algorithms and sequence similarity search tools to search sequence databases (public domain databases include Genbank, EMBL, Swiss-Prot, PIR and others).

Similarity searches retrieve and align sequences for comparison with a target sequence to be analyzed (i.e., a query sequence). The optimal alignment between local regions of the compared sequences is known as a local alignment. Sequence comparison algorithms use scoring matrices to assign an overall score to each of the alignments.

Polynucleotide and polypeptide sequences may be aligned, and percentage of identical residues in a specified region may be determined against other polynucleotide and polypeptide sequences, using computer algorithms that are publicly available. The percentage identity score is dependent on the length of the overlap region of the sequences being compared.

The similarity between two nucleic acid sequences, or two amino acid sequences may be expressed in terms of sequence identity (or, for proteins, also in terms of sequence similarity). Sequence identity is frequently measured in terms of percentage identity; the higher the percentage, the more similar the two sequences are. As described herein, homologs and variants of the PSRB1 nucleic acid molecules may be used in the present invention. Homologs and variants of these nucleic acid molecules will possess a relatively high degree of sequence identity when aligned using standard methods. Such homologs and variants will hybridize under high stringency conditions to one another.

Methods of alignment of sequences for comparison are well known in the art. Various programs and alignment algorithms are described in: Smith and Waterman (1981); Needleman and Wunsch (1970); Pearson and Lipman (1988); Higgins and Sharp (1988); Higgins and Sharp (1989); Corpet et al. (1988); Huang et al. (1992); and Pearson et al. (1994). Altschul et al. (1994) presents a detailed consideration of sequence alignment methods and homology calculations.

The NCBI Basic Local Alignment Search Tool (BLAST) (Altschul et al., 1990) is available from several sources, including the National Center for Biotechnology Information (NCBI, Bethesda, Md.) and on the Internet, for use in connection with the sequence analysis programs blastp, blastn, blastx, tblastn and tblastx. It can be accessed at the NCBI Website. A description of how to determine sequence identity using this program is available at the NCBI website.

Homologs of the disclosed protein sequences are typically characterized by possession of at least 40% sequence identity counted over the full length alignment with the amino acid sequence of the disclosed sequence using the NCBI Blast 2.0, gapped blastp set to default parameters. The adjustable parameters are preferably set with the following values: overlap span 1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity. Proteins with even greater similarity to the reference sequences will show increasing percentage identities when assessed by this method, such as at least about 50%, at least about 60%, at least about 70%, at least about 75%, at least about 80%, at least about 90% or at least about 95% sequence identity.

Homologs of the disclosed nucleic acid sequences are typically characterized by possession of at least 40% sequence identity counted over the full length alignment with the amino acid sequence of the disclosed sequence using the NCBI Blast 2.0, gapped blastn set to default parameters. In addition, such sequences hybridize to homologous sequences under high stringency conditions. A preferred method utilizes the BLASTN module of WU-BLAST-2 (Altschul et al., 1996); set to the default parameters, with overlap span and overlap fraction set to 1 and 0.125, respectively. Nucleic acid sequences with even greater similarity to the reference sequences will show increasing percentage identities when assessed by this method, such as at least about 50%, at least about $^{60}$%, at least about 70%, at least about 75%, at least about 80%, at least about 90% or at least about 95% sequence identity.

The alignment may include the introduction of gaps in the sequences to be aligned. In addition, for sequences which contain either more or fewer amino acids than the protein depicted in FIG. 8B, it is understood that in one embodiment, the percentage of sequence identity will be determined based on the number of identical amino acids in relation to the total number of amino acids. Thus, for example, sequence identity of sequences shorter than that shown in the figures as discussed below, will be determined using the number of amino acids in the longer sequence, in one embodiment. In percent identity calculations relative weight is not assigned to various manifestations of sequence variation, such as, insertions, deletions, substitutions, etc.

In one embodiment, only identities are scored positively (+1) and all forms of sequence variation including gaps are assigned a value of "0", which obviates the need for a weighted scale or parameters as described herein for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

Proteins can be classified according to their sequence relatedness to other proteins in the same genome (paralogs) or a different genome (orthologs). Ortholog genes are genes that evolved by speciation from a common ancestral gene. These genes normally retain the same function as they evolve. Paralog genes are genes that are duplicated within a genome. These genes may acquire new specificities or modified functions which may be related to the original one. Phylogenetic analysis methods are well-known to those with ordinary skill in bioinformatics.

As will be appreciated by those skilled in the art, the sequences of the present invention may contain sequencing errors. That is, there may be incorrect amino acid sequences, nucleotides, frameshifts, unknown nucleotides, or other types of sequencing errors in any of the sequences; however, the correct sequences will fall within the homology and stringency definitions herein.

High Stringency: High stringency refers to hybridization conditions which are chosen to optimize binding of polynucleotide sequences with a high degree of complementarity. Stringency is affected by factors such as temperature, salt conditions, the presence of organic solvents in the hybridization mixtures, and the lengths and base compositions of the sequences to be hybridized and the extent of base mismatching, and the combination of parameters is more important than the absolute measure of any one factor. An example of high stringency conditions for hybridizing a probe to a filter-bound DNA is 5×SSC, 2% sodium dodecyl sulfate (SDS), 100 ug/ml single stranded DNA at 55–65° C. for 20 minutes, and washing in 0.1×SSC and 0.1% SDS at 60–65° C. for 20 minutes.

Construct: Unless otherwise stated, the term "construct" refers to a recombinant genetic molecule comprising one or more isolated polynucleotide sequences of the invention.

Genetic constructs used for transgene expression in a host organism comprise in the 5'–3' direction, a gene promoter sequence; an open reading frame coding for at least a functional portion of a polypeptide of the present invention; and a gene termination sequence. The open reading frame may be orientated in either a sense or anti-sense direction. The construct may also comprise selectable marker gene(s) and other regulatory elements for gene expression.

Vector: The term "vector" refers to a nucleic acid molecule which is used to introduce a polynucleotide sequence into a host cell, thereby producing a transformed host cell. A "vector" may comprise genetic material in addition to the above-described genetic construct, e.g., one or more nucleic acid sequences that permit it to replicate in one or more host cells, such as origin(s) of replication, selectable marker genes and other genetic elements known in the art (e.g., sequences for integrating the genetic material into the genome of the host cell, and so on).

Transformed: A transformed cell is a cell into which has been introduced a nucleic acid molecule by molecular biology techniques. As used herein, the term transformation encompasses all techniques by which a nucleic acid molecule might be introduced into such a cell, plant or animal cell, including transfection with viral vectors, transformation by *Agrobacterium*, with plasmid vectors, and introduction of naked DNA by electroporation, lipofection, and particle gun acceleration and includes transient as well as stable transformants.

Isolated: An "isolated" biological component (such as a nucleic acid or protein or organelle) has been substantially separated or purified away from other biological components in the cell or the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term embraces nucleic acids including chemically synthesized nucleic acids and also embraces proteins prepared by recombinant expression in vitro or in a host cell and recombinant nucleic acids as defined below.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter controls the transcription or expression of the coding sequence. Generally, operably linked DNA sequences are contiguous and, where necessary, join two protein-coding regions in the same reading frame. With respect to polypeptides, two polypeptide sequences may be operably linked by covalent linkage, such as through peptide bonds or disulfide bonds.

Recombinant: By "recombinant nucleic acid" herein is meant a nucleic acid that has a sequence that is not naturally occurring or has a sequence that is made by an artificial combination of two otherwise separated segments of sequence. This artificial combination is often accomplished by chemical synthesis or, more commonly, by the artificial manipulation of nucleic acids, e.g., by genetic engineering techniques, such as by the manipulation of at least one nucleic acid by a restriction enzyme, ligase, recombinase, and/or a polymerase. Once introduced into a host cell, a recombinant nucleic acid is replicated by the host cell, however, the recombinant nucleic acid once replicated in the cell remains a recombinant nucleic acid for purposes of this invention. By "recombinant protein" herein is meant a protein produced by a method employing a recombinant nucleic acid. As outlined above "recombinant nucleic acids" and "recombinant proteins" also are "isolated" as described above.

Complementary DNA (cDNA): A piece of DNA that is synthesized in the laboratory by reverse transcription of an RNA, preferably an RNA extracted from cells. cDNA produced from MRNA may include 5' and/or 3' noncoding sequences (i.e., 5' UTR, 3' UTR) but typically lacks internal, non-coding segments (introns) and regulatory sequences, such as promoters, that determine transcription.

Open reading frame (ORF): A continuous coding sequence of a gene flanked by a start and stop codon. An ORF lacks internal termination codons and can usually be translated into an amino acid sequence.

Non-naturally Occurring Plant: A non-naturally occurring plant is a plant that does not occur in nature without human intervention. Non-naturally occurring plants include transgenic plants and plants produced by non transgenic means such as plant breeding.

Transgenic plant: As used herein, this term refers to a plant or tree that contains recombinant genetic material not normally found in plants or trees of this type and which has been introduced into the plant in question (or into progenitors of the plant) by human manipulation. Thus, a plant that is grown from a plant cell into which recombinant DNA is introduced by transformation is a transgenic plant, as are all offspring of that plant that contain the introduced transgene (whether produced sexually or asexually). It is understood that the term transgenic plant encompasses the entire plant or tree and parts of the plant or tree, for instance grains, seeds, flowers, leaves, roots, fruit, pollen, stems etc.

Ortholog: Two nucleotide or amino acid sequences are orthologs of each other if they share a common ancestral sequence and diverged when a species carrying that ancestral sequence split into two species, sub-species, or cultivars. Orthologous sequences are also homologous sequences. Orthologous sequences hybridize to one another under high-stringency conditions. The term "polynucleotide", "oligonucleotide", or "nucleic acid" refers to a polymeric form of nucleotides of any length, either deoxyribonucleotides or ribonucleotides, or analogs thereof. The terms "polynucleotide" and "nucleotide" as used herein are used interchangeably. Polynucleotides may have any three-dimensional structure, and may perform any function, known or unknown. The following are non-limiting examples of polynucleotides: a gene or gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. A "fragment" or "segment" of a nucleic acid is a small piece of that nucleic acid.

Gene: A "gene" refers to a polynucleotide containing at least one open reading frame that is capable of encoding a particular protein after being transcribed and translated. In the present invention, the gene for PSRB1 is an open reading frame that is capable of encoding the amino acid sequence depicted in FIG. 8B or an orthologous or homologous protein.

Primer: The terms "primer" and "nucleic acid primer" are used interchangeably herein. A "primer" refers to a short polynucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a polymerase and at a suitable temperature and pH. The primer may be either single-stranded or double-stranded and must be sufficiently long to prime the synthesis of the desired extension product. The exact length of the primer will depend upon many factors, including temperature, source of primer and use of the method.

Polymerase chain reaction: A "polymerase chain reaction" ("PCR") is a reaction in which replicate copies are made of a target polynucleotide using a "primer pair" or a "set of primers" consisting of an "forward" and a "reverse" primer, and a catalyst of polymerization, such as a DNA polymerase, and particularly a thermally stable polymerase enzyme. Methods for PCR are taught in U.S. Pat. No. 4,683,195 (Mullis) and U.S. Pat. No. 4,683,202 (Mullis et al.). All processes of producing replicate copies of the same polynucleotide, such as PCR or gene cloning, are collectively referred to herein as "amplification" or "replication".

Small RNA Molecules: Small RNA molecules are single stranded or double stranded RNA molecules generally less than 200 nucleotides in length. Such molecules are generally less than 100 nucleotides and usually vary from 10 to 100 nucleotides in length. In a preferred format, small RNA molecules have 11, 12, 13, 14, 15, 16, 17, 18, 19, 20, 21, 22, 23, 24, 25, 26, 27, 28, 29 or 30 nucleotides. Small RNAs include microRNAs (miRNA) and small interfering RNAs (siRNAs), which are circa 21–25 nt length, and have 5' phosphate and 3'hydroxyl. MiRNAs are produced by the cleavage of short stem-loop precursors by Dicer-like enzymes, whereas siRNAs are produced bu the cleavage of long double-stranded RNA molecules. MiRNAs are single-stranded, whereas siRNAs are double-stranded.

Non-cell autonomous: Small RNA mediated signaling events operating both locally between cells and long-distance via the phloem system.

DESCRIPTION OF PREFERRED EMBODIMENTS

This application discloses the identification, purification and characterization of a novel protein component of the phloem translocation stream in higher plants which binds to phloem-mobile small RNA molecules and mediates their cell-to-cell transport through plasmodesmata. The protein is believed to be essential for non-cell autonomous signalling processes which utilize small RNA.

In one of its aspects, the present invention provides isolated polynucleotide sequences encoding phloem small RNA binding proteins (PSRB). An exemplary PSRB amino acid sequence purified from Cucurbita maxima phloem sap is shown below in FIG. 8B. The invention-encompasses the coding sequences and their complements, and sequences that hybridize under high stringency conditions to sequences that encode the protein sequence depicted in FIG. 8B: Variants and homologs of the inventive polynucleotide sequence that encode proteins that bind specifically to, and mediate cell-to-cell movement of, small RNAs are intended to be covered by in this invention.

In another of its aspects, the invention provides genetic constructs comprising polynucleotide sequences encoding a PSRB protein and modified forms of these sequences, e.g., dominant negative mutations. The genetic constructs can be used to transform a host organism, preferably a plant, or a portion or cell thereof, to manipulate the expression of a PSRB protein, for example, by knockout, overexpression or expression of dominant negative forms of the protein in plants. Changes in expression of PSRB protein is expected to result in changes in systemic signaling processes involving small RNA signalling molecules.

In yet another aspect, the invention provides oligonucleotide probes and primers for hybridization-based and/or PCR-based detection, quantitation and/or amplification of PSRB polynucleotide sequences.

In another aspect, the invention is directed to transgenic plants comprising a PSRB polynucleotide sequence. Such transgenic plants may contain altered levels and activities of PSRB proteins, and exhibit changes in physiological responses that depend on non cell autonomous signaling. The present invention is further directed to seed produced by the transgenic plants of the invention.

The invention further provides methods for using genetic constructs comprising PSRB sequences to modulate non-cell autonomous signaling events involving small RNA molecules, e.g., siRNA and miRNA. These signaling events underlie a broad spectrum of plant developmental, physiological and biochemical processes, including, for example, flowering, coordination of plant growth and development, systemic resistance to pathogens, responses to environmental stresses, e.g., heat, drought, salinity, systemic gene silencing (e.g., viral infections), biomass distribution, regulation of carbon metabolism and control of plant size, developmental timing and developmental patterning.

The present invention also provides isolated PSRB polypeptide sequences and various methods of using these sequences.

The present invention is further directed to the identification and isolation of small RNA molecules which are involved in systemic signaling processes, and to the use of such molecules to alter plant developmental, physiological and biochemical processes such as flowering, coordination of plant growth and development, systemic resistance to pathogens, responses to environmental stresses, e.g., heat, drought, salinity, systemic gene silencing (e.g., viral infections), biomass distribution, regulation of carbon metabolism and control of plant size, developmental timing and developmental patterning.

The present invention is further directed to transgenic plants containing altered levels and distributions of these mobile small RNA signaling molecules.

Figure 1:
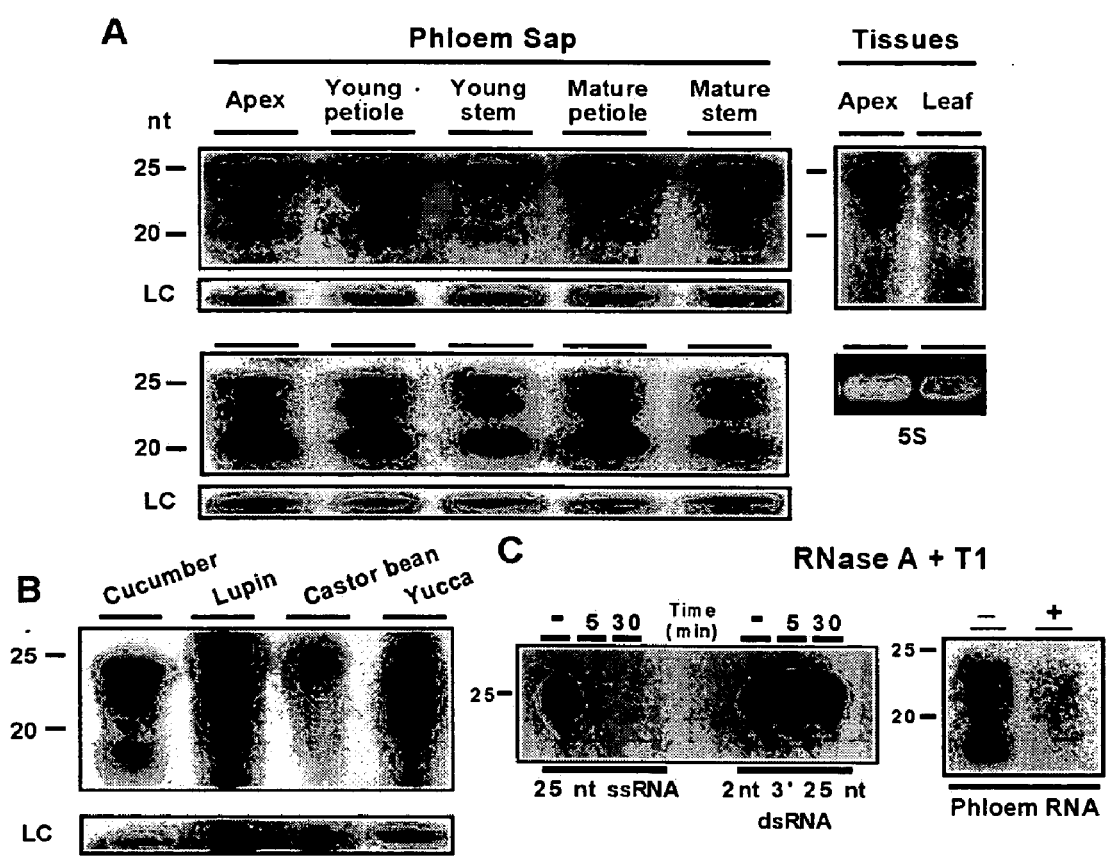
FIG. 1. Small RNA population detected in the pumpkin phloem translocation stream. (A) Small RNA species present within the phloem sap and vegetative tissues of pumpkin (*Cucurbita maxima*) were extracted, end-labeled with $^{32}$P-phosphate, separated using PAGE and then visualized by autoradiography. Left upper and lower panels; samples from summer- and winter-grown plants, respectively. Loading control (LC); a constant high molecular weight band present in the unfractionated phloem sap RNA was used for between sample calibration. Right upper and lower panels; apical and mature leaf tissues from summer-grown plants and ethidium bromide stained 5S rRNA as loading control, respectively (0.3 µg per lane). (B) Small RNA species detected in the phloem sap of cucumber (*Cucumis sativus*), white lupin (*Lupinus albus*), caster bean (*Ricinus communis*), and yucca (*Yucca filamentosa*). (C) Single-stranded RNA-specific RNase assay performed on control (synthetic 25 nt ss- and 2 nt 3'25 nt dsRNA) and phloem small RNA preparations. Note the absence of signal associated with the synthetic 25 nt ssRNA and low residual level in the phloem small RNA population after treatment.

Earlier efforts to identify the nature of the RNA species that serve as the systemic signaling agent(s) were based on analyses conducted on leaf tissues (5–7, 22–24), rather than directly on the phloem translocation stream. To overcome this limitation, we here utilized a model plant system, founded upon the *cucurbits*, from which analytical quantities of phloem sap can be collected (16, 25); this experimental system has the added advantage that established protocols are available for the isolation and analysis of phloem-mobile proteins and RNA (8, 9). Analysis of the cucurbit phloem sap (collected from pumpkin) demonstrated the presence of an endogenous population of small RNA, ranging from 18 to 24 nt in size (FIG. 1A). These experiments were performed on summer- and winter-grown plants and revealed the dynamics associated with this small RNA population. A comparison of the small RNA species present in leaves, the vegetative apex and the phloem sap indicated that each displayed a unique pattern in terms of the relative abundance of the small RNA molecules (FIG. 1A). Examination of the phloem sap collected from a number of plant species confirmed the presence of small RNA, indicating the generality of this finding (FIG. 1B). Biochemical assays established that these small RNAs were produced by the action of an RNase III-type enzyme (26) and the predominant form, within the phloem sap, appeared to exist as single-stranded (ss) entities (FIG. 1C).

Figure 2:
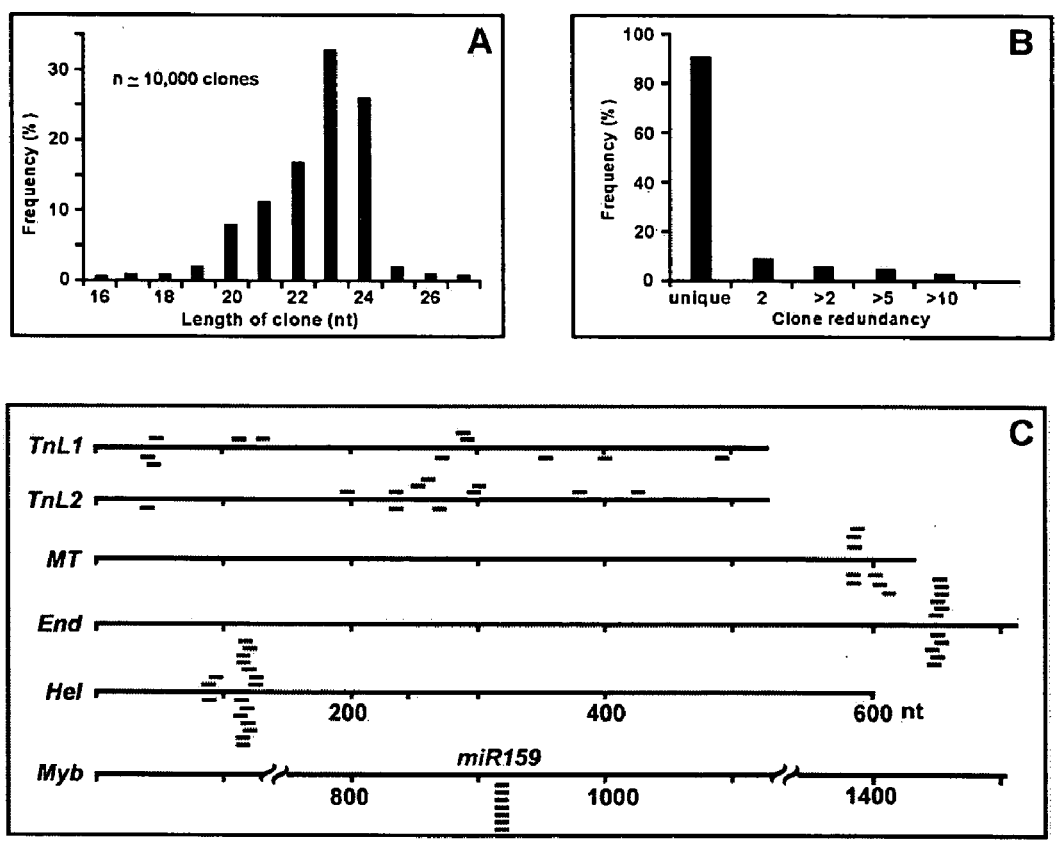
FIG. 2. Molecular size, complexity and potential targets for phloem small RNA species. (A) and (B) Size distribution and complexity, respectively, of the small RNA species contained within a phloem database (10,000 clones) generated from summer-grown pumpkin (sap collected from mature petioles). (C) Representative putative target genes of phloem small RNA with identified homology to cucurbit ESTs and/or *Arabidopsis* genes. Distribution of sense (above target gene; black, 0; green, 1; red, 2; and blue 3 mismatches, respectively) and antisense (below target gene; colors as described for sense) clones directed against the indicated genes. Targets: cucurbit transposon-like 1 and 2 (TnL1 & TnL2); cucurbit small RNA identical to *Arabidopsis* miR159 proposed to target a MYB transcription factor (GenBank accession number At2g32460); putative methyltransferase (MT; homologous to a spinach gene [GenBank accession number AF237633]), bifunctional endonuclease (End; homologous to a *Zinnia elegans* gene [GenBank accession number O80326]) and RNA helicase (Hel; homologous to a *Vigna radiata* gene [GenBank accession number AF156667]). The size-classes directed against the TnL and Myb genes were centered on 21 nt, whereas those associated with MT, End, and Hel were in the 23–24 nt range.
Figure 3:
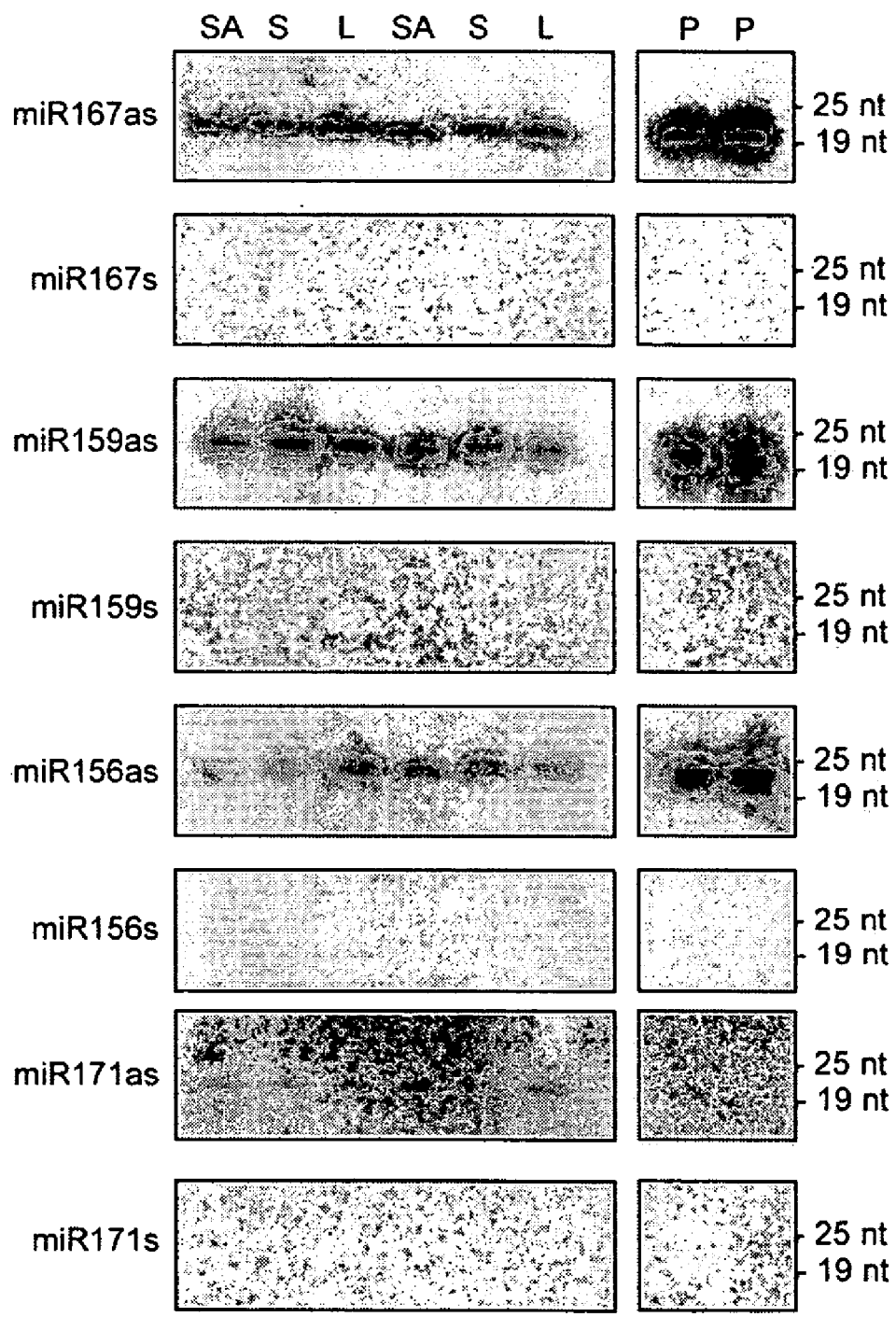
FIG. 3. Northern blot analysis of miRNA in various pumpkin tissues and phloem sap. Total RNA was extracted from shoot apices (SA), stem tissue (S), mature leaves (L) and phloem sap (P) and the small RNA species extracted by size fractionation. Duplicate RNA samples were separated on a denaturing polyacrylamide gel, transferred to Hybond-N+ nylon membrane and hybridized with either radiolabeled DNA sense (s) or antisense (as) probes complementary to four identified plant miRNAs (miR156, mir159, miR167, and miRNA171 [Reinhart et al., 2002]). Position of RNA oligonucleotide standards is indicated on the right. RNA loading was normalized by spectrometry and 2 µg of small RNA was used per lane.

We next extracted and cloned these phloem small RNA species (26) in order to gain insight into their form and identity. The distribution of the various size-classes was consistent with the phloem small RNA pattern (FIG. 2A). Interrogation of these clones revealed the underlying complexity in the nature of this population (FIG. 2B). Bioinformatic analysis using plant genomic databases confirmed the authenticity of these phloem small RNA species and, further, allowed us to identify potential targets, including transposon-like genes (FIG. 2C). The sequences of these small RNA species are provided in Table 1. The sequences in Table 1 correspond to potential targets including methyltransferase, bifunctional endonuclease, and DEAD/DEAH box RNA helicase. Sequences corresponding to cucumber yellow virus and transposon-like sequences were also among the small RNAs isolated from phloem (Table 1). These findings implicate the involvement of both siRNA and miRNA in phloem-mediated long-distance regulation of gene function in plants.

Figure 4:
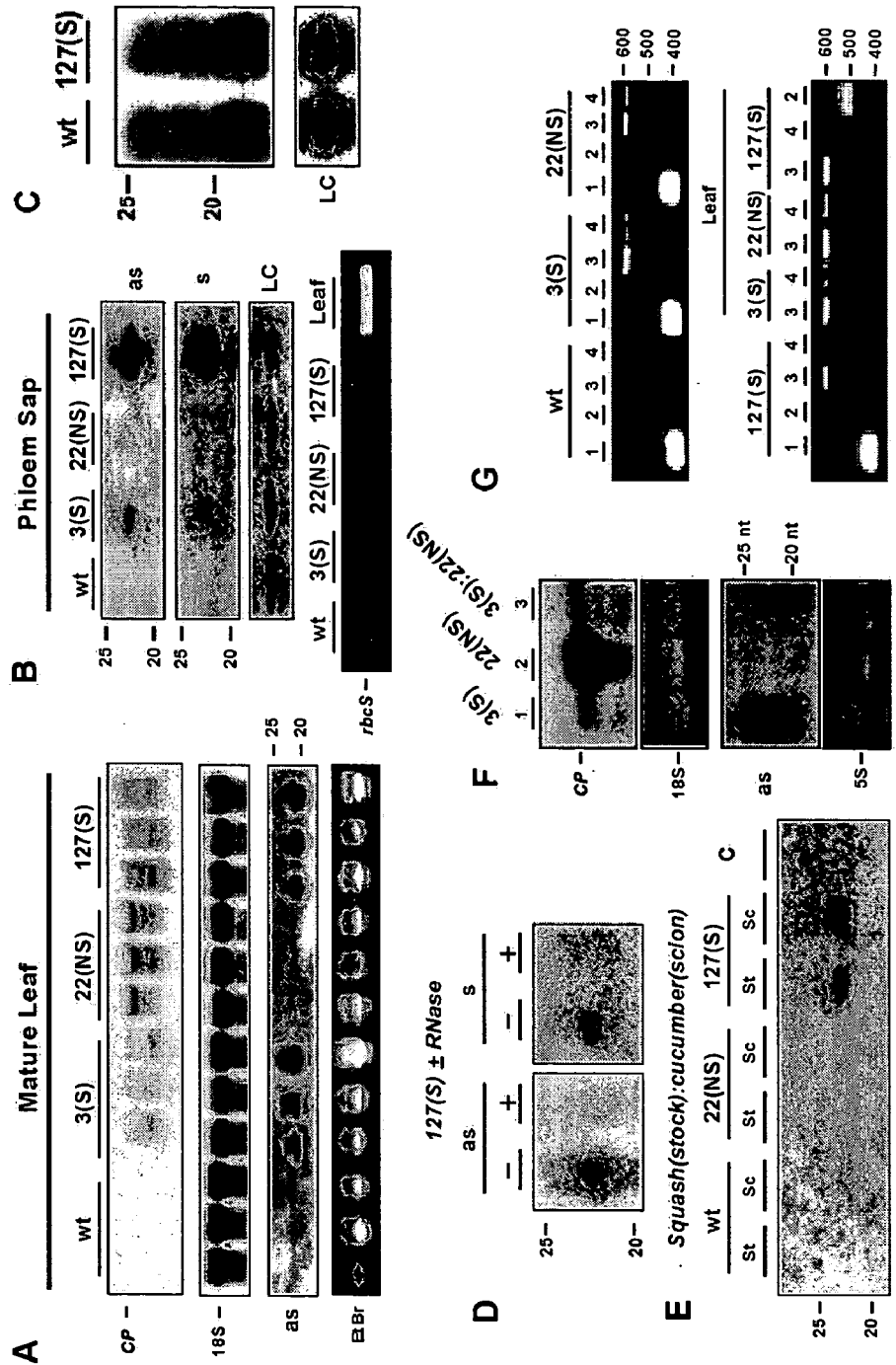
FIG. 4. Identification of RNA species in the phloem of spontaneously silencing CP transgenic squash lines. (A) Northern analysis of RNA extracted from spontaneously silencing (3[S] and 127[S]) and non-silencing (22[NS]) squash lines expressing the CP of Squash mosaic virus (SqMV; Pang et al., 2000). Upper panels: hybridization analysis performed with CP and 18S probes. Lower panels: small RNA detected using antisense (as) CP riboprobe; loading control provided by ethidium bromide staining (EtBr). (B) Northern analyses performed on phloem sap collected from squash lines in (A), using as- and sense (s)-riboprobes; LC, loading control. Lower panel: phloem sap integrity confirmed by RT-PCR using rbcS primers. (C) Comparison of small RNA populations present in the phloem sap of wild-type (wt) and CP transgenic spontaneously silencing (line 127) squash plants. (D) Single-stranded RNA-specific RNase assay. (E) Northern analysis performed on phloem sap collected from heterografted plants, using as-riboprobe. Positive signals were detected in phloem sap collected from both the stock (St, squash) and cucumber scion (Sc) samples taken from heterografted 127(S) plants, a spontaneously silencing line. Signal was not detected in the phloem from heterografted non-silencing CP transgenic line 22 (NS), nor from homografted wild-type squash (wt) or cucumber (C) plants. Equivalent results were obtained using s-riboprobe. (F) Northern analysis of SqMV CP RNA (upper panel) and siRNA (lower panel) extracted from the scion apex of control (homografted 3[S] and 22[NS]) and heterografted (3[S] stock:22[S] scion) plants. Loading controls; 18S and 5S riboprobes. (G) RT-PCR analysis detected s- and as-CP transcripts in phloem sap collected from summer-grown squash. CP primers were used to amplify full-length transcripts (600 bp) from phloem sap and leaf RNA samples collected from wild-type and CP expressing squash lines. RT-PCR performed with internal CP primers gave similar results. Controls for these experiments used primers for CmPP16 (400 bp) and rbcS (500 bp). Lanes are as follows: 1, CmPP16; 2, rbcS; 3, CP sRNA; 4, CP asRNA.

Our current understanding of RNA silencing in plants is based primarily on experiments performed using leaf tissues expressing transgenes (5–7). Such a transgenic system was next used to test for the presence, in the phloem, of the associated siRNA. Here, spontaneously silencing lines of a cucurbit species, expressing a viral coat protein (CP) gene (27; FIG. 4A), were employed for phloem sap analysis. These studies identified CP siRNA, in the 23 nt size range, present within the phloem of silenced lines; no such siRNA was detected from either non-silenced CP transgenic or wild-type plants (FIG. 4B). Comparable small RNA profiles were observed in wild-type and CP silenced squash plants (FIG. 4C), suggesting that the CP siRNA is not a dominant species. Although both sense and antisense CP siRNA were detected at similar levels, our enzyme assays revealed the absence of the dsRNA form (FIG. 4D). Grafting experiments were next performed to further test whether these CP siRNA are bonafide constituents of the phloem translocation stream, as opposed to wound-induced contaminants derived from neighboring silenced tissues. Phloem sap collected from cucumber scions grafted onto either wild-type or non-silencing CP transgenic squash lines was free of CP siRNA (FIG. 4E). In contrast, equivalent experiments performed with cucumber (scion) and the spontaneously silencing squash line 127 (stock), revealed the presence of both sense and antisense CP siRNA in the phloem sap taken from both stock and scion tissues.

The question of whether other forms of CP RNA are present in the phloem sap was investigated using RT-PCR and northern analyses. No specific amplification product was detected in experiments performed with a range of primer sets (FIG. 4G). Similar results were obtained in northern hybridization analysis (FIG. 4F). Thus, it would seem unlikely that ss/ds-full-length or aberrant forms of the CP RNA are present within the long-distance translocation stream. In this case, the detected CP siRNA would then serve as the systemic signaling agent (1, 7).

Systemic viral infection of plants occurs through the phloem translocation stream (28). Recent studies have demonstrated that plants utilize RNA silencing as a surveillance mechanism to protect against viral attack (29). Translocation of CP siRNA, in our transgenic cucurbits, is consistent with the observed systemic resistance to viral infection likely afforded through RNA silencing (27). Viral infection of cucurbits was next used to test for the presence of siRNA, in the phloem, during this process. Molecular analyses revealed that the phloem sap, collected from *Cucumber yellows closterovirus* (30; CuYV)-infected pumpkin, contained both sense and antisense siRNA (20–21 nt size-class) directed along the length of the viral genome (FIG. 5A). As expected, the phloem sap also contained CuYV transcripts (26), likely reflecting a dynamic balance between RNAi-based surveillance and viral infection. In contrast to the spontaneously silencing CP lines, a comparison of the small RNA present in the phloem of healthy and infected plants indicated that viral infection elicited a significant shift in this population resulting from an increase in siRNA derived from the viral RNA (FIG. 5B). These findings confirm the participation of small RNA species in the systemic response of the plant to viral challenge.

The phloem sap has been shown to contain proteins involved in mRNA trafficking (8). Here, we investigated whether the phloem translocation stream also contains proteins that bind specifically to small RNA. Northwestern assays were first performed using a phloem-mobile mRNA, in order to identify the spectrum of phloem proteins that could bind to this transcript (FIG. 6B). This pattern was then compared to that obtained using either sense or antisense synthetic 25 nt RNA (FIG. 6 D and E) and revealed the presence of a 27 kDa protein that bound differentially and strongly to small RNA. Parallel experiments performed using phloem-purified small RNA (18 to 24 nt) confirmed this result (FIG. 6F). Biochemical protocols were next used to purify this 27 kDa phloem protein (26) to permit cloning of the corresponding gene [FIG. 8.], termed *Cucurbita maxima* PHLOEM SMALL RNA-BINDING PROTEIN1 (CmPSRB1). The equivalent patterns obtained by western and Northwestern analysis (FIG. 6 C to E) confirmed that PSRB1 is a phloem small RNA-binding protein [FIG. 10].

The binding specificity of PSRB1 was further investigated using a range of small RNA molecules, including various ds-forms. These Northwestern studies showed that PSRB1 binds to both small ss- and dsRNA, but it displayed an apparent higher affinity for ssRNA species (FIG. 6 D to I). This observation was confirmed by gel mobility-shift assays. Here, recombinant PSRB1 (R-PSRB1) displayed high-affinity binding with ssRNA, whereas it showed only weak, or no binding to dsRNA (FIG. 9). We also noted that the phloem sap contains proteins capable of form-specific interaction with dsRNA (FIG. 6 H and I).

A database search using CmPSRB1 failed to identify highly related homologues in other plant species. This outcome was not unexpected, given the low complexity reflected in the primary sequence [FIG. 8]. This necessitated an investigation into the existence of PSRB1-like proteins in the phloem of other species, using a combination of immunological and RNA-binding assays. First, we examined the phloem sap from cucumber, as it represents a distant relative of pumpkin (31). Here, a 27 kDa phloem protein was identified having properties equivalent to those observed for CmPSRB1 [FIG. 7 A–E]. Parallel studies were next performed with lupin, a member of the legume family, and yielded similar results (FIG. 7 F–J). Collectively, these findings support the notion that PSRB1 likely represents a common component of the higher plant phloem translocation stream.

The example provided herein discloses the isolation of PSRB1 protein from pumpkin phloem, chymotryptic digestion of the protein, microsequencing of the protein, RT-PCR, and cDNA cloning and sequencing of the cDNA for PSRB1. One of ordinary skill in the art would be able to obtain the sequences of PSRB1 proteins from other plant species using standard biochemical and molecular biological techniques disclosed herein. Specifically, a person of ordinary skill in the art would be able to apply anion-exchange chromatography or similar well known chromatographic methods to isolate PSRB1 from the phloem of other plant species. The isolated PSRB1 protein can then be subjected to N-terminal amino acid sequencing and/or protease treatment to generate peptide fragments for microsequencing. The amino acid sequence information derived from these methods can be used to design oligonuculeotide primers for either screening a cDNA library or for use as RT-PCR primers. The products of RT-PCR can be used to screen a cDNA library to isolate the corresponding cDNAs, which can then be fully sequenced to ascertain the nucleic acid and protein sequences of PSRB1 proteins from other plant species. Furthermore, using the sequence of PSRB1, one of skill in the art can identify and clone homologs and orthologs of PSRB1. Routine cloning and bioinformatics techniques including database analyses can be utilized to identify core conserved regions of PSRBs. These methods are well known to one of skill in the art and are described in sources such as Sambrook, Fritsch and Maniatis, MOLECULAR CLONING: A LABORATORY MANUAL, 2nd edition (1989); CURRENT PROTOCOLS IN MOLECULAR BIOLOGY [(F. M. Ausubel, et al. eds., (1987)] and are further disclosed herein with reference to PSRB1 protein.

By virtue of their small size, it has been assumed that small ss- and dsRNA move cell to cell through PD by simple diffusion (7). In this scenario, the PSRB1 could bind to small RNA species to restrict their movement from the phloem translocation stream out into vascular cells. To address this question, we employed microinjection techniques to test first whether small RNA can indeed diffuse through PD. Various forms of 21 and 25 nt ss- and dsRNA were fluorescently labeled, injected into target cells, and their movement observed with a confocal laser scanning microscope (26). As none of these small RNA species moved out of the injected cell (FIG. 11, A and B; Table 3)i we concluded that the PD size exclusion limit (SEL; ~800 Da [32]) in this tissue must have prevented diffusion of these molecules. To further explore this potential mode of small RNA movement, we next used endogenous and viral movement proteins previously shown to mediate an increase in PD SEL during their cell-to-cell trafficking (3, 11; Table 3). These studies showed that an increase in PD SEL, to greater than 20 kDa, did not permit diffusion of the co-injected small RNA out of the target cell (FIG. 11, C and D, Table 3, Table 4). Given that the size of both the 25 nt ss- and dsRNA (~8 and ~16 kDa, respectively) is below that of the 20 kDa PD SEL, the lack of movement may reflect either sequestration within the cell or involvement of a more complex mechanism.

These studies raised the possibility that PSRB1 may function in the cell-to-cell trafficking of small RNA. Evidence in support of such a function was gained through microinjection experiments performed with native and R-PSRB1. Both forms of the protein mediated the movement of fluorescently labeled small RNA into neighboring cells (FIG. 11, E and F, Table 3). This movement capacity of PSRB1 appeared to be specific to small ssRNA, as it failed to traffic large RNA transcripts, small dsRNA and ssDNA (FIG. 11, G and H, Table 3). Finally, movement of small RNA mediated by PSRB1 was limited to the neighboring cells (FIGS. 11, E and F). This finding is of interest in the context of recent results obtained on SHR (14) and CPC (15), in that these plant transcription factors also underwent limited cell-to-cell movement.

Our findings offer support for the concept that the phloem translocation stream contains a sub-population of small RNA that is responsive to environmental/growth conditions. The various cucurbit size-classes, including the 17–19 nt, 20–21 nt, and 23–24 nt, likely reflect the involvement of different Dicer-like enzymes and suggests branches in the silencing pathways involving small RNA molecules (17). The apparent complexity in this sub-population, in conjunction with the identification of their potential target genes, supports the notion that these small RNA species function in the systemic spread of both the siRNA and miRNA epigenetic pathways. Our identification and functional characterization of the PSRB1 class of phloem small RNA binding proteins provides insight into the molecular machinery involved in systemic si-/miRNA signaling. These findings now establish a foundation for further dissection of the pathways and mechanisms utilized to exert long-distance control over viral infection, transposon activities, and transcriptional/translational processes (7, 17, 21, 33, 34).

Production of Transgenic Plants with Altered Systemic Small RNA Signaling System The polypeptides of the present invention, which are encoded by the polynucleotides of the present invention, have activity in binding phloem-mobile small RNAs that are putative signals for non-cell autonomous signaling processes. Using the methods and materials of the present invention, the developmental, physiological and biochemical responses of a plant that depend on non-cell autonomous (i.e., local cell to cell and long-distance) signaling mechanisms which involve small RNA signals may be modulated by modulating expression of polynucleotides of the present invention, or by modifying the polynucleotides or polypeptides encoded by polynucleotides. The isolated polynucleotides and polypeptides of the present invention may thus be usefully employed for example to abrogate systemic gene silencing, or alternatively, to elevate the activity of systemic silencing signals such that a signal initiated in one part of the plant would be efficiently transported to distant parts of the plant to switch off genes in a variety of plant species. Examples of systemic signaling processes that may depend on small RNA metabolism include responses to pathogens and environmental stresses, differentiation of shoot and root apical meristems and lateral organ formation (e.g., floral induction), differentiation of the vascular cambium, and others.

The level and activity of PSRB polypeptides in a target organism, such as a plant, may be modified, for example, by incorporating a polynucleotide sequence of the invention into the genome of the organism and overexpressing the sequence in a sense orientation to increase the level and activity of the polypeptide. By transforming the plant with an antisense construct or gene silencing construct, the level and activity of the polypeptide can be decreased. Similarly, by transforming a plant with a modified form of the PSRB-encoding polynucleotide sequence, e.g., a truncated sequence encoding a dominant negative form of the polypeptide, or a mutated sequence with altered small RNA binding activity, the activity of the PSRB protein can be reduced.

The present invention thus provides methods for modulating the polynucleotide and/or polypeptide content and composition of an organism, such methods involving stably incorporating into the genome of the organism a genetic construct comprising one or more polynucleotides of the present invention.

Standard molecular biology methods and plant transformation techniques can be used to produce transgenic plants that produce plants having altered levels of PSRB protein (i.e., levels that are increased or decreased compared to the levels of non-transformed plants). Such levels are generally controlled. The following sections provide general guidance as to the selection of particular constructs and transformation procedures.

Introduction of the selected construct into plants (including trees) is typically achieved using standard transformation techniques. The basic approach is to: (a) clone the construct into a transformation vector, which (b) is then introduced into plant cells by one of a number of techniques (e.g., electroporation, microparticle bombardment, *Agrobacterium* infection); (c) identify the transformed plant cells; (d) regenerate whole plants from the identified plant cells, and (d) select progeny plants containing the introduced construct.

Successful examples of the modification of plant characteristics by transformation with cloned nucleic acid sequences are replete in the technical and scientific literature. Selected examples, which serve to illustrate the knowledge in this field of technology include:U.S. Pat. No. 5,571,706 ("Plant Virus Resistance Gene and Methods"); U.S. Pat. No. 5,677,175 ("Plant Pathogen Induced Proteins"); U.S. Pat. No. 5,510,471 ("Chimeric Gene for the Transformation of Plants"); U.S. Pat. No. 5,750,386 ("Pathogen-Resistant Transgenic Plants"); U.S. Pat. No. 5,597,945 ("Plants Genetically Enhanced for Disease Resistance"); U.S. Pat. No. 5,589,615 ("Process for the Production of Transgenic Plants with Increased Nutritional Value Via the Expression of Modified 2S Storage Albumins"); U.S. Pat. No. 5,750,871 ("Transformation and Foreign Gene Expression in Brassica Species"); U.S. Pat. No. 5,268,526 ("Overexpression of Phytochrome in Transgenic Plants"); U.S. Pat. No. 5,780,708 ("Fertile Transgenic Corn Plants"); U.S. Patent No. 5,538,880 ("Method for Preparing Fertile Transgenic Corn Plants"); U.S. Pat. No. 5,773,269 ("Fertile Transgenic Oat Plants"); U.S. Pat. No. 5,736,369 ("Method for Producing Transgenic Cereal Plants"); U.S. Pat. No. 5,610,049 ("Methods for Stable Transformation of Wheat"); U.S. Pat. No. 6,235,529 ("Compositions and Methods for Plant Transformation and Regeneration").

The transgene-expressing constructs of the present invention may be usefully expressed in a wide range of higher plants and trees. The invention is applicable to monocotyledonous cereal plants including barley, wheat, rice, rye, maize, triticale, millet, sorghum, oat, forage, and turf grasses. The invention may also be applied to dicotyledenous plants, including, but not limited to, soybean, sugar beet, cotton, beans, rape/canola, alfalfa, flax, sunflower, safflower, brassica, cotton, flax, peanut, clover; vegetables such as lettuce, tomato, cucurbits, cassava, potato, carrot, radish, pea, lentils, cabbage, cauliflower, broccoli, Brussels sprouts, peppers; and tree fruits such as apples, pears, peaches, apricots, and walnuts.

Vector Construction

A number of recombinant vectors suitable for stable transformation of plant cells or for the establishment of transgenic plants have been described including those described in Weissbach and Weissbach (1989), and Gelvin et al. (1990). Typically, plant transformation vectors include one or more ORFs under the transcriptional control of 5' and 3' regulatory sequences and a dominant selectable marker with 5' and 3' regulatory sequences. The selection of suitable 5' and 3' regulatory sequences for constructs of the present invention is discussed above. Dominant selectable marker genes that allow for the ready selection of transformants include those encoding antibiotic resistance genes (e.g., resistance to hygromycin, kanamycin, bleomycin, G418, streptomycin or spectinomycin) and herbicide resistance genes (e.g, phosphinothricin acetyltransferase).

Transformation and Regeneration Techniques

Methods for the transformation and regeneration of both monocotyledonous and dicotyledonous plant cells are known, and the appropriate transformation technique will be determined by the practitioner. The choice of method will vary with the type of plant to be transformed; those skilled in the art will recognize the suitability of particular methods for given plant types. Suitable methods may include, but are not limited to: electoporation of plant protoplasts; liposome-mediated transformation; polyethylene glycol (PEG-mediated transformation); transformation using viruses; micro-injection of plant cells; micro-projectile bombardment of plant cells; vacuum infiltration; and *Agrobacterium*-mediated transformation. Typical procedures for transforming and regenerating plants are described in the patent documents listed at the beginning of this section.

Selection of Transformed Plants

Following transformation, transformants are preferably selected using a dominant selectable marker. Typically, such a marker will confer antibiotic or herbicide resistance on the seedlings of transformed plants, and selection of transformants can be accomplished by exposing the seedlings to appropriate concentrations of the antibiotic or herbicide. After transformed plants are selected and grown the plant can be assayed for expression of PSRB1

Identification of Modulators of PSRB Activity

The isolated PSRB proteins of this invention can be used in in vitro assays to identify modulators, preferably small molecules, and more preferably, small molecules that can be externally applied to plants, that increase or decrease the binding of PSRB to small RNAs. Small molecule screens of this type are well-known in the art and can be adapted for use by those of ordinary skill in the art, using routine experimentation. Microinjection assays of the type described herein can be used to test the effect of putative modulators on in planta PSRB activities related to cell-to-cell transport (e.g., altering the SEL of PDs).

Various modulators of small RNA metabolism of viral origin are known in the art. These include the polyviral HC-Pro, the CMV 2b and the TBSV P19 products. HC-Pro is known to disrupt silencing in cells where it is present and 2b is known to disrupt the long distance systemic silencing signal. Isolated and purified PSRB proteins, such as CmPSRB, may be used to screen for additional modulators of small RNA metabolism/signaling. Modulation of the activity of CmPSRB1 and its homologs in plants may be useful for manipulating small RNA metabolism.

Use of PSRB to Identify Small RNA Signaling Molecules

The PSRB proteins of the invention are able to bind small RNA molecules and may be utilized to identify putative small RNA signaling molecules present in the phloem. Such molecules can be isolated by procedures well known in the art. Such methods include affinity purification of RNAs using expressed RNA binding proteins. In one such method, the RNA binding protein can be expressed from a cloned nucleic acid using an in vitro translation system such that the protein is made with a tag such as biotinylated lysine. The biotinylated protein can then be immobilized with avidin Sepharose to make an affinity column. A sample of phloem containing RNAs can be incubated with the affinity resin in a mild buffer such as Tris-buffered saline (TBS), allowing protein-target RNA interaction to occur. Unbound RNAs can be washed from the resin, after which the bound RNA is eluted from the resin using a strong denaturing agent such as TRIzol® reagent. The RNAs can be collected by ethanol precipitation can be and then cloned and characterized as described herein in the Example. See, for example, Zaidi et al. J. Biol. Chem., 269, 24000 (1994). Alternatively, the RNA binding protein can be expressed at a larger scale and directly coupled to an activated support such as Sepharose and used as an affinity column directly, utilizing the RNA binding, washing, and elution conditions described above.

Once isolated, the small RNA molecules can be assessed for their ability to modify gene activity and expression in plants. In some cases, the identity of small RNA-regulated genes can be determined from sequence comparisons of small RNAs with known genes.

Antibody Production

Antibodies to PSRB1 can be generated using methods known in the art. PSRB1 protein can be suspended in an appropriate adjuvant and used to inoculate animals such as rabbits or goats to generate polyclonal antibodies. Alternatively, other animals including mice may be inoculated with PSRB1 antigen to generate monoclonal antibodies utilizing. hybridoma technology. Such methods are described in sources such as Harlow and Lane (1988), ANTIBODIES, A LABORATORY MANUAL.

Exemplary materials and methods for practicing the embodiments of this invention are described below. Those skilled in the art will know of other materials and methods that can be substituted for those described herein. This Example is intended to be illustrative, and not to limit the scope of the invention.

EXAMPLE

Materials and Methods

Plant Materials.

*Cucurbita Maxima* cv. Big Max (pumpkin), *Cucumis sativus* cv. Straight Eight (cucumber), and *Ricinus communis* (castor bean) plants were grown in a special insect- and pathogen-free greenhouse under natural daylight conditions (summer: midday irradiance, 1200–1500 µmol. $m^{-2}$ $sec^{-1}$ photosynthetically active radiation [PAR], 35/20° C. day/night temperatures, day length 14 h; winter: midday PAR 800 µmol. $m^{-2}$ $min^{-1}$, 30/20° C. day/night temperatures, day length 12 h, extended by 300 µmol. $m^{-2}$ $sec^{-1}$ artificial lighting). Nutrients were delivered, daily, as described online at the website: greenhouse.ucdavis.edu/materials/nutrients_soil.htm. *Lupinus albus* cv. 1234 (white lupin) plants were grown, during the winter/spring of 2003, in the Agronomy and Range Science field station at the University of California, Davis, Davis, Calif.

Grafting Protocols.

Heterografting experiments were performed as previously described (S1 refers to the first reference in the list of references at the end of the Example), with modifications. Heterografts were generated between scions, cut from 6–8-week-old cucumber plants. (vegetative apex to $2^{nd}$ mature leaf) and stocks, provided by 8–12-week-old squash plants; inclusion of mature leaves on the scions increased the grafting efficiency to >90%. Each excised cucumber scion (15–20 cm in length) was carefully inserted into an incision made in the main stem of a squash plant. The graft site was fastened and sealed with Parafilm™ and the scion was then covered with a clear plastic bag that was removed 1 week later. These grafting experiments were carried out under winter greenhouse conditions. Plants were employed for phloem sap analysis 3 weeks after grafting. Larger leaves on the scion were removed 3 days prior to phloem sap collection.

Phloem Sap Collection for Analysis of RNA and Proteins.

Phloem sap was collected from well-watered plants, as previously described (S1, S2), with modifications. Full citations for the Example references are provided at the end of the Example. Briefly, stems or petioles for cucurbits, or inflorescent stalks for lupin (S3, S4) and castor bean (S5, S6), were excised with a sterile razor blade and the cut surface blotted, several times, with sterile filter paper (#3 MM: Whatman, Maidstone, UK). Phloem sap exuded thereafter was collected using sterile micropipette tips (200 µl) and immediately mixed either with an equal volume of protein sap collection buffer (100 mM Tris, pH 7.5, 10 mM EDTA, 5 mM EGTA, 10% [v/v] glycerol, 1% [v/v] 2-mercaptoethanol, and protease inhibitors [Complete™, Roche, Indianapolis, Ind.]), or 200 µl with 500 µl of TRIzol® (Invitrogen, Carlsbad, Calif.) reagent for phloem sap RNA. All buffers were kept on ice during phloem sap collection.

Phloem RNA Quantitation.

High molecular weight phloem RNA was separated from the small RNA as described below. Contaminating genomic DNA was removed by DnaseI treatment (Invitrogen) for 15 min at 20° C., followed by phenol/chloroform extraction and ethanol precipitation. The concentration of high molecular weight RNA was measured using RiboGreen RNA Quantitation Kit (Molecular Probes, Eugene, Oreg.) according to the manufacturer's instructions. Using these methods pumpkin and cucumber had measured RNA levels of 300 and 400 ng RNA /ml phloem sap, respectively.

Small RNA Analysis.

Phloem sap was collected as described above. For end-labeling, 200 µl of phloem sap was added to 500 µl of TRIzol® reagent, 200 µl of chloroform was then added and the sample was first vortexed, followed by centrifugation (16,000×g) for 15 min at 4° C. RNA was then precipitated (1 volume isopropanol, 1/10 volume 3 M sodium acetate, and 20 µg/ml linear acrylamide [Ambion, Austin, Tex]), overnight, at −20° C., followed by centrifugation (16,000×g) for 30 min at 4° C. The RNA pellet was washed with 80% (v/v) ethanol and resuspended in 10 µl of DEPC-treated water. RNA was 5' exchange end-labeled as described (S7), using 10 U T4 Polynucleotide Kinase (New England Biolabs, Beverly, Mass.) with the supplied buffer to which was added 100 µM ADP, 2.5 nM ATP, and 165 nM [γ-$^{32}$P] ATP (3000 Ci/mmol) for 30 min at 37° C. Unincorporated $^{32}$P-label was removed using a MicroSpin™ G-25 column (Amersham Biosciences, Piscataway, N.J.), according to the manufacturer's instructions. For RNA analysis, an equal volume of Loading Buffer II (Ambion) was added and the sample heated at 95° C. for 5 min, followed by electrophoresis (7 M urea/15% PAGE gel; 1 mm thickness, 15 cm length) at 300V, for approx. 2 h, using 1×TBE as running buffer. Gels were then exposed for autoradiography (Biomax MS film [Eastman Kodak, Rochester, N.Y.]).

As the overall pattern of the phloem sap RNA was reasonably constant from sample to sample, one band in this profile was employed as a loading control for the analysis of small RNA species.

Isolation of phloem small RNA, from acrylamide gels, was performed as described (S8), with modifications. RNA was resuspended in a total of 30 µl DECP-treated water and an aliquot (5 µl) was end-labeled, as described, and added back to the unlabeled RNA sample. Next, this sample was electrophoresed on a 7 M urea/15% PAGE gel and then exposed to X-ray film. The region containing the 18–25 nt RNA was excised and purified. Isolation and enrichment of small RNA extracted from leaves was as follows: total RNA was extracted with TRIzol® reagent and a 50 µg aliquot was size-fractionated (S9; RNeasy mini column, QIAGEN, Valencia, Calif.). The small RNA present in the flow-through was precipitated, as above, and the pellet washed with 80% ethanol and resuspended in 10 µl of RNase-free water.

The concentration of small RNA in the phloem sap was determined as described above for high molecular weight RNA. The values for pumpkin were in the range of 0.3–6.0 fmol small RNA/µl phloem sap.

Confirmation that Phloem Small RNA are RNase III Products.

The chemical nature of the 5'-terminal residue of the phloem small RNA was established using the following protocols. Aliquots of small RNA (both synthetic and phloem-purified) were treated with SAP and polynucleotide kinase. (SAP will remove phosphates from either the 5' or 3' end, whereas polynucleotide kinase treatment will add a single phosphate to the 5' end of the small RNA species.) Following enzymatic treatment, these small RNAs were separated as described above and analyzed for changes in electrophoretic migration. Consistent with 5'-phosphorylation status, the phloem small RNA treated with polynucleotide kinase had the same mobility as the untreated samples. SAP treatment decreased the apparent mobility of the small RNA (by 1 nt), consistent with the removal of a negatively charged phosphate group and further treatment of these dephosphorylated small RNA with polynucleotide kinase and ATP restored the original mobility. The presence of a monophosphate group on the 5'-end of the phloem small RNA species is consistent with them being products of an RNase III.

Synthetic Small RNA.

Chemically synthesized, deprotected, and HPLC-purified 25 nt RNA oligonucleotides were obtained from Integrated DNA Technologies, Inc. (Coralville, Iowa). Oligonucleotides used in experiments included FK202, 5'rCrArGrUrGrUrCrUrUrCrUr-CrCrCrUrCrArCrUrG-3' (SEQ ID NO: 3); FK203, 5'-rCrArGrUrGrUrCrUrUrCrUrCrCr-CrUrCrArCrUrGrCrUrArCrU-3'(SEQ ID NO: 4) FK216, 5'-rGrCrArGrUrGrArGrGrGrArGrArArGrArCrArCrUrG-3' (SEQ ID NO: 5); FK221, 5'-rGrGrArArArArCrUrArCr-CrUrGUrUrCrCrArUrGrGrCrCrArA-3' (SEQ ID NO: 6); FK222, 5'-rUrGrUrUrGrGrCrCrArUrGr-GrArArCrArGrGrUrArGrUrUrUrU-3' (SEQ ID NO: 7); FK223, 5'-rUrUrGrGrCrCrArUrGrGrAArCrAr-GrGrUrArGrUrUrUrUrCrC-3' (SEQ ID NO: 8); FK224, 5'-rGrGrCrCrArUrGrGrArArCrArGr-GrUrArGrUrUrUrUrCrCrArG-3' (SEQ ID NO: 9). FK221 was in a sense-orientation whereas all others were in the antisense-orientation. These oligonucleotides were derived from GFP. Various forms of 25 nt dsRNA were generated by annealing different combinations of these oligonucleotides: 25 nt dsRNA with 5' 2 nt overhang, FK221 with FK222; blunt end, FK221 with FK223; 3' 2 nt overhang, FK221 with FK224. Protocols for annealing and validation of dsRNA formation were as described (S10). Labeling of the 5' ends of the 25 nt ss- and dsRNAs with $^{32}$P was performed with T4 polynucleotide kinase (New England Biolabs, Inc., Beverly, Mass.) as described (S8).

RNase assay.

Single-stranded specific RNase assays were carried out as described (S7). Briefly, 5'-$^{32}$P-radiolabeled ss-, ds- or phloem-sap-purified small RNA was incubated with 1 ng of RNase A and 1U of RNase T1 (Ambion), in 10 µl of RNase digestion buffer (300 mM NaCl, 50 mM Tris, pH 7.0, and 1 mM EDTA) at 37° C. for 30 min. The reaction mixtures were then analyzed by denaturating PAGE (7 M urea/15% PAGE gel) and autoradiography.

Cloning, Sequencing and Bioinformatics of Small RNA.

Phloem sap small RNA was isolated and purified as described above, with the exception that 15 to 30 nt size-range RNA was gel-purified. This population of small RNA was then ligated to adapters and amplified by RT-PCR according to procedures described (S11). Adapter and primer sequences were as described (S11) with the exception that adaptors were fluorescently tagged (3' fluorescein for the 3' adaptor and 5' Cy5 for the 5' adaptor). Ligation products were visualized using a Typhoon scanner (model 9400; Amersham Biosciences, Helsinki, Finland) or using a UV transilluminator. The amplified sequences were gel-purified and cloned into pCR4-TOPO vector (Invitrogen), followed by electroporation into *E. coli* DH10B cells.

The transformants (approx. 10,000 clones) were first sequenced with the BigDye terminator cycle sequencing kit (PE Applied Biosystems, Foster City, Calif.). These sequences were first analyzed to establish the size-class distribution of the phloem sub-population of small RNA. Redundancy was established using BlastN (available online at the site ncbi.nlm.nih.gov/BLAST/) to compare each clone in this database against every other small RNA sequence. Identity of each clone was probed by conducting an analysis against both a proprietary cucurbit EST and the public databases. Here, the e-value chosen for cutoff, 1e-05, was empirically determined to allow for a minimum 18 nt alignment and sequences were manually curated to identify those with 0–3 mismatches.

Probable rRNA and tRNA contaminants were identified as sequences with 0–3 nt changes to Arabidopsis rRNA and tRNA sequences or cucurbit rRNA sequences by using databases available online. Putative microRNA candidates were identified on the basis of phylogenetic conservation, as sequences with 0–3 nt changes to Arabidopsis intergenic region sequences (TAIR Arabidopsis Intergenic sequences; available online at the site arabidopsis.org).

Identity of potential target sequences was probed by conducting FASTA analyses with each sequence and its reverse complement against proprietary ESTs [Genesis Research and Development Corporation plant consensi including sequences from: *Actinidia, Cucurbita, Eucalyptus, Festuca, Lolium, Malus domestica, Pinus radiata* and *Vaccinium* (a total of 349411 sequences)] and public plant databases [TIGR Gene Indices (available online at the site tigr.org) including: *Chlamydomonas reinhardtii, Glycine max, Gossypium, Lycopersicon esculentum, Medicago truncatula, Pinus taeda, Triticum aestivum, Vitis vinifera, Zea mays* (a total of 412390 sequences)]. Sequences within each of these datasets were then mapped by TBLASTX against *Arabidopsis* genes (TAIR CDS; available online at the site arabidopsis.org). Criteria used to identify putative miRNA targets included: 1) a reverse orientation match to an Arabidopsis gene; 2) instances where mapping onto the same (or similar) *Arabidopsis* genes was observed from two or more species and 3) manual inspection of the *Arabidopsis* gene annotation in instances where multiple *Arabidopsis* gene IDs were identified.

Identified conserved sequences were further analysed by an RNA-folding program (RNAFold from Vienna package, available online at the site tbi.univie.ac.at/~ivo/RNA/), leading to identification of candidates with a potential fold-back precursor structure that contains the miRNA sequence within one arm of the hairpin. Small RNA candidates are then confirmed by both in silico and transcriptional profiling of phloem sap small RNA by Northern blotting.

Parallel analyses were performed on small RNA cloned from the phloem sap collected from viral-infected greenhouse-grown (summer) pumpkin plants. The virus used in these experiments was CuYV (GenBank accession numbers AB085612 [RNA 1] and AB085613 [RNA 2]), and its presence in the phloem sap was confirmed using standard molecular protocols (S7). Phloem sap used in these studies was collected during the severe phase of infection. Phloem sap used in these studies was from plants showing clear symptoms of virus infection. Sequence identity of each clone was established using BlastN against CuYV sequence (GenBank accession numbers AB085612 [RNA 1] and AB085613 [RNA 2]). Size-class analysis and sequence identity were as described above.

Northern and RT-PCR Analyses of Transgenic Squash Plants.

Analysis of leaf full-length CP transcripts was performed as follows: total RNA was extracted from mature squash leaves with TRIzol® reagent, separated on a formaldehyde-containing 1% agarose gel (10 μg total RNA/lane), and transferred to a Hybond-N+ nylon membrane (Amersham Biosciences), overnight. The membrane was UV-crosslinked and then pre-hybridized, at 65° C. for 1 h in hybridization buffer (0.5 M $Na_2HPO_4$, 1 mM EDTA, 1% BSA, and 7% SDS). The membrane was then hybridization, overnight, with full-length Squash mosaic virus (SqMV) CP DNA probe that was radiolabeled by random priming (NEN, Boston, Mass.). The membrane was washed (2×15 min at 65° C.) in 2×SSC, and again (2×15 min) in 0.1×SSC, followed by exposure to X-ray film for 12 h at −80° C. Equal loading was confirmed by stripping the membrane in 0.1% SDS at 95° C. and re-probing with a squash 18S rRNA DNA probe.

Northern analysis of the enriched small RNA preparation was carried out as follows: RNA was separated on a denaturating acrylamide gel, urea removed and the RNA stained with ethidium bromide to visualize the amounts loaded. RNA was then transferred to Hybond-N+ nylon membrane using a trans-blot SD cell (BioRad, Hercules, Calif; 1 h at 3 $mA/cm^2$). Pre-hybridization and hybridization were as described, except that the temperature was 45° C., and the probe was either full-length sense or antisense SqMV CP RNA, generated by in vitro transcription using SP6 or T7 RNA polymerase (Ambion), respectively. The membrane was washed (2×10 min, 50° C. in 2×SSC, 0.1% SDS) and then exposed to X-ray film, overnight, at −80° C.

Northern blot analyses of cucurbit miRNA were carried out as described above with the exception that DNA sense or antisense probes were end-labeled by the forward reaction as described (S7), using 10 U T4 Polynucleotide Kinase (New England Biolabs, Beverly, Mass.) with the supplied buffer to which was added 300 nM [γ-32P] ATP (3000 Ci/mmol) for 10 min at 37° C. Unincorporated 32P-label was removed using a MicroSpin™ G-25 column (Amersham Biosciences, Piscataway, N.J.), according to the manufacturer's instructions. Hybridization signal was detected using a Typhoon scanner (Model 9400; Amersham Biosciences, Piscataway, N.J.).

RT-PCR analysis of phloem sap RNA was performed as follows. An aliquot (3 μl) of the high molecular weight RNA (obtained by QIAGEN column size-fractionation), was used in RT-PCR with SuperScriptII RT (Invitrogen) according to the manufacturer's recommendations, with gene-specific primers: CmPP16-3', 5'-ATGGGTTTGAAGAAGC-CAAGCCACTTA-3' (SEQ ID NO: 10); rbcS-3', 5'-TTGTC-GAAGCCAATGACTCTGATGAA-3' (SEQ ID NO: 11); SqMVCP-3', 5'-CATGGAGCTAGATCTTGCG-CAACTTTCTCTG-3' (SEQ ID NO: 12). An aliquot (3 μl) of the RT reaction was used for PCR amplification, with the following conditions: 5 min at 95° C. (1 cycle); 30 sec at 94° C., 30 sec at 60° C., 90 sec at 72° C. (35 cycles). The same 3' primers were used as for the RT reaction, in addition to the following 5' primers: CmPP16-5',5'-GTGGTAAAGGACT-TCAAGCCCACGACC-3' (SEQ ID NO: 13); rbcS-5',5'-

ATGGCTTCCATCGTCTCATCCGCC-3' (SEQ ID NO: 14); SqMVCP-5',5'-CATGGTACAGCAGCTTGGAACT-TATATTCC A-3' (SEQ ID NO: 15).

Full-length SqMVCP was amplified using the above-described primer set. The presence of smaller SqMVCP fragments was probed using two internal primer sets: SqM-VCP-1,5'-CACTGCTGATTTGATGGAATCCACG-3' (SEQ. ID NO: 16) (begins at 86 bp) was used with SqM-VCP4,5'-AACTCGATGTCGCCTCCTCGTGGCTTA-3' (SEQ ID NO: 17) (ends at 355 bp) and SqMVCP-3,5'-GCTGCGTCAGCTAGAATAGAC-3' (SEQ ID NO: 18) (begins at 255 bp) was used with SqMVCP-5, 5'-AGGTG-GATTTAAAGTATTTCCAGCCAC-3' (SEQ ID NO: 19) (ends at 533 bp). Reverse transcription was performed as described, using SqMVCP-4 and SqMVCP-5' as primers.

Anion-Exchange Chromatography and Northwestern Analysis of Phloem Sap Proteins.

Anion-exchange chromatography of pumpkin, cucumber, and lupin phloem sap proteins was camed out as follows. Generally, 20 ml of pumpkin or cucumber phloem sap (10–20 mg/ml) or 45 ml of lupin phloem sap (0.1–0.2 mg/ml) was employed for the chromatographic separation of phloem proteins. Phloem sap was first dialyzed against buffer A (50 mM Tris, pH 7.5, 1 mM EDTA, and 30 mM 2-mercaptoethanol) and clarified by centrifugation (17,000× g, for 30 min). Phloem proteins were then loaded onto a buffer A-equilibrated HiTrap Q column, connected to an FPLC system (Amersham Biosciences). After washing the column with 20 column-volumes of buffer A, proteins were eluted with a linear gradient of 0–500 mM NaCl in buffer A supplemented with 1 M NaCl.

For northwestern analysis (S12), phloem proteins in each of the HiTrap-Q fractions were resolved by 13% SDS-PAGE and then electro-transferred to nitrocellulose membrane. After staining with Ponceau S to-mark the lanes and molecular weight markers, the membranes were thoroughly washed first with TBS (50 mM Tris, pH 8.0, and 500 mM NaCl), followed by DEPC-treated Milli-Q water (Millipore, Bedford, Mass.). Washed membranes were further rinsed, briefly, with 10 ml of RNA binding buffer (RBB; 10 mM Tris, pH 7.0, 50 mM KCl, 1 mM EDTA, 0.02% [w/v] Ficoll, and 0.02% [w/v] polyvinylpyrrolidone), and blocked at 25° C. for 1 h with 10 ml of the RBB supplemented with 0.02% (v/v) ultrapure BSA (Ambion) and 0.1 mg/ml yeast total RNA. Next, membranes were rinsed, twice, with RBB supplemented only with BSA for 10 min each. Hybridization was performed with $^{32}$P-labeled probes (2×105 cpm/ml) in 7 ml of RBB supplemented with BSA at 25° C. for 1 h. Membranes were then washed (3×5 min) with RBB, briefly air-dried, and autoradiographed.

Purification of CmPSRB1 from Pumpkin Phloem Sap and Mass Spectroscopic Analysis.

All purification steps were performed at 4° C. Phloem proteins were fractionated by anion-exchange chromatography, as described above, and then analyzed by a combination of SDS-PAGE/GelCode Blue staining (Pierce, Rockford, Ill.) and northwestern assays in order to locate the CmPSRB1-containing fractions. Next, metal chelation chromatography was employed, based on our results for amino acid composition analysis (Molecular Structure Facility, Univ. of California, Davis) that revealed a high content of histidine in this protein. For this purpose, fractions were pooled, the NaCl concentration adjusted to 500 mM, and this preparation loaded onto a metal chelation column (Novagen, Madison, Wis.), equilibrated with binding buffer (20 mM Tris, pH 8.0, 500 mM NaCl, and 10 mM imidazole). After washing with 20 column-volumes of the washing buffer containing 60 mM imidazole, CmPSRB1 was eluted with a buffer solution containing 400 mM imidazole. Remaining CmPSRB1 was released using a second elution buffer (20 mM Tris, pH 8.0, 150 mM NaCl, and 100 mM EDTA).

Mass spectroscopic analysis of phloem-purified CmPSRB1 was performed using matrix-assisted laser desorption ionization time-of-flight (MALDI-TOF) on a Biflex III system (Bruker, Billerica, Mass.) as described (S2).

Chymotryptic Digestion, Microsequencing, RT-PCR, cDNA Library Screening, and cDNA Cloning.

CmPSRB1 was found to be recalcitrant to commonly used endoproteinases. To resolve this problem, phloem-purified CmPSRB1 (1 µg) was digested with a less specific proteinase, chymotrypsin (0.1 µg), in 20 µl digestion buffer (100 mM Hepes, pH 8.0, and 10 mM $CaCl_2$) for 2 h at 25° C. Resultant peptides were then resolved on a 15% nondenaturating tricine PAGE gel, electro-blotted to a PVDF membrane, stained with Coomassie R250, and then subjected to Edman sequencing (Molecular Structure Facility). Two microsequences were obtained: HGP(G/S)(P/H)G(P/H)A(G/H)G(H/P)(G/S)GPA (SEQ ID NO: 20) and GHGP(A/S)GGHGH(G/H)P(A/S)A (SEQ ID NO: 21). Pumpkin stem mRNA was used in RT-PCR with degenerate primers; 5'-GGICAYGGICCIGCIGGIGGICAYGGICA-3' (SEQ ID NO: 22) and 5'-CAYGGICCIGGICCIGGICCIGCIGGIG-GICAY-3' (SEQ ID NO: 23) (I; inosine, Y; U/C). Cloning required a high temperature of 60° C. for reverse transcription using Thermoscript RT (Invitrogen), to yield a specific PCR product of 450 bp. This experimental condition was consistent with the high G/C content of CmPSRB1. The resultant PCR product was then used as a probe to screen a pumpkin stem cDNA library (S2). After three cycles of screening, 9 positive plaques were purified from approximately 1.5×10$^5$ pfu; cDNA inserts were then rescued in pBK-CMV by in vivo excision followed by sequencing.

Expression and Purification of Recombinant CmPSRB1.

For expression and purification of recombinant I-CmPSRB1, an expression vector, pET15b-CmPSRB1, was constructed: an NcoI-XhoI fragment from pBK-CMV/CmPSRB1 was ligated into pET15b, which was previously digested with NcoI and XhoI, and dephosphorylated with CIAP. The resultant plasmid, pET15b-CmPSRB1, permitted expression of CmPSRB1, as a native protein, without a (HiS)$_6$ fusion. *Escherichia coli*, BL21(DE3)pLysS, harboring pET15b-CmPSRB1 was induced with 0.5 mM IPTG for 2–3 h at 22° C. For purification, cells were lysed by sonication (4–6 pulses for 1 min each using a Sonic Dismembrator, Fisher Scientific, Pittsburgh, Pa.) and centrifuged at 20,000×g for 30 min at 4° C. The cleared supernatant was then applied to a metal chelation column and R-CmPSRB was purified as described above.

In situ RT-PCR Detection of CmPSRB1.

The spatial distribution of CmPSRB1 was determined using our previously established protocols for in situ RT-PCR (S1). The primer pair used to amplify CmPSRB1 transcripts was: forward primer, 5'-CTAATCTTTGCATC-CATGGCGTCTTTCCAATGC-3' (SEQ ID NO: 24); reverse primer, 5'-TTAGTGCTGACCTCTGCGA-CAATCGTTGTCAC-3' (SEQ ID NO: 25). For comparative purposes, the pattern associated with CmPP16 was determined using the following primer pair: forward primer, 5'-GTGGTAAAGGACTTCAAGCCCACGACC-3'-(SEQ ID NO: 26); reverse primer, 5'-ATGGGTTTGAAGAAGC- CAAGCCACTTA-3' (SEQ ID NO: 27). Controls for these studies were performed in the absence of the appropriate primers.

Western Analysis.

Primary antibody used to detect CmPSRB1, and its homologues in other plant species, was a monoclonal anti 6-His antibody (Covance, Berkeley, Calif.). This antibody efficiently recognized CmPSRB1 and its homologues in western analyses, due to their high histidine content. The general protocol for western analysis was as described (S7). Briefly, nitrocellulose membranes were blocked, with 5% non-fat milk made in TBS, for 0.5–1 h, incubated with the primary antibody for 1 h, washed four times with TTBS (TBS supplemented with 0.5% [v/v] Tween 20) for 5 min each, and then incubated for 30 min with secondary antibodies conjugated to horseradish peroxidase (KPL, Gaithersburg, Md.). Membranes were then washed as described above. Visualization of antigen and antibody complexes was achieved using luminol and oxidizing reagents (Renaissance™, PerkinElmer Life Sciences, Inc.) as substrates for the HRP.

Electrophoretic Mobility-shift Assay.

Electrophoretic mobility-shift assays were carried out as described (S12). Reactions were assembled on ice in 10 µl of binding buffer (20 mM Hepes, pH 7.0, 50 mM KCl, 1 mM EDTA, 1 mM DTT, and 5% [v/v] glycerol). An equal amount of $^{32}$P end-labeled 25 nt ss- or dsRNA was used in assays with various concentrations of purified and desalted R-CmPSRB1. Reaction mixtures were incubated at 30° C. for 20 min and then placed on ice. Reactions were then resolved on a 5% (v/v) nondenaturing polyacrylamide gel that was pre-run for 30 min at 50 V. Electrophoresis was typically carried out at 4° C. and 200 V. The gel was then dried and autoradiographed.

Microinjection Experiments.

RNA molecules for microinjection experiments were labeled either with Alexa Fluor 488 or 568 using ULYSIS Nucleic Acid Labeling Kit (Molecular Probes, Eugene, Oreg.), according to the manufacturer's protocol. Unincorporated fluorescent label was separated by repeated ethanol precipitation, or by a G-25 gel filtration column (Amersham Biosciences). The integrity of fluosceritly labeled probes was verified by 3% (w/v) agarose gel electrophoresis and fluorescence imaging. Recombinant proteins, KNOTTED1 (KN1) and *Cucumber mosaic virus* movement protein (CMV-MP), were expressed in and isolated from *E. coli* as previously described (S13, S14).

Eight-week-old *Nicotiana benthamiana* plants were used for microinjection studies, with a minimum of five plants for each probe tested. Leaves (3–5 cm in length) were excised and prepared for microinjection experiments as described (S15). Fluorescently labeled RNA was resuspended with 1–3 µg/µl purified protein solution to yield a final RNA concentration of 1–2 µg/µl. Fluorescein isothiocyanate-labeled dextran (20 kDa FITC-dextran, Sigma, St. Louis, Mo.) was mixed with protein to give a final concentration of 2 mM. All probes were stored at 4° C. and integrity of RNA was confirmed before use in each microinjection experiment. Microinjection protocols were as previously described (S14, S15), and probes were introduced via pressure-mediated delivery. Cell-to-cell movement of fluorescently labeled probes was observed using a confocal laser-scanning microscope (CLSM, model DM RXE TCS-4D, Leica, Heidelberg, Germany). Spatial distribution of fluorescence within the mesophyll tissue was evaluated for a 20 min period after the probe(s) was introduced into a target cell. Images were simultaneously collected for the fluorescent signals emitted in the FITC/Alexa Fluor 488 nm (green), Alexa-Flour 568 nm (red) and chlorophyll 665 nm (blue) channels. Optical sections were stacked and then combined to generate the images presented.

The following references cited herein are incorporated by reference in their entirety.

EXAMPLE REFERENCES

S1. R. Ruiz-Medrano, B. Xoconostle-Cázares, W. J. Lucas, *Development* 126, 4405 (1999).
S2. B.-C. Yoo, J.-Y. Lee, W. J. Lucas, *J. Biol. Chem.* 277, 15325 (2002).
S3. J. S. Pate, P. J. Sharkey, O. A. M. Lewis, *Planta* 120, 229 (1974).
S4. C. A. Atkins, *J. Exp. Bot.* 50, 805 (1999).
S5. S. M. Hall, D. A. Baker, *Planta* 106, 131 (1972).
S6. W. D. Jeschke, J. S. Pate, *J. Exp. Bot.* 42, 1105 (1991).
S7. J. Sambrook, E. F. Fritsch. T. Maniatis, *Molecular Cloning* (Cold Spring Harbor Press, Plainview, N.Y., 1988).
S8. F. M. Ausubel et al., *Current Protocols in Molecular Biology* (Wiley, New York, N.Y., 1998).
S9. F. Di Serio et al., *Proc. Natl. Acad. Sci. USA* 98, 6506 (2001).
S10. S. M. Elbashir, J. Harborth, K. Weber, T. Tuschl, *Methods* 26, 199 (2002).
S11. S. M. Elbashir, W. Lendeckel, T. Tuschl, *Genes Dev.* 15, 188 (2001).
S12. C. W. J. Smith, *RNA: Protein Interactions* (Oxford University Press, New York, N.Y. 1998).
S13. W. J. Lucas et al., *Science* 270, 1980 (1995).
S14. M. R. Rojas, F. M. Zerbini, R. F. Allison, R. L. Gilbertson, W. J. Lucas, *Virology* 237, 283 (1997).
S15. B. Xoconostle-Cźares et al., *Science* 283, 94 (1999).

TABLE 1

DNA Sequences of small phloem RNA molecules.

| CLONE | SEQUENCE | SEQ ID NO: | # OF MISMATCHES | SENSE(s) ANTISENSE(s) | TYPE | GENE NAME |
|---|---|---|---|---|---|---|
| CuYV01 | TTCTGTCGTTCCACTTTGCAA | SEQ ID NO: 28 | 0 | as | cucumber yellows virus (CuYV) | RNA2 |
| CuYV02 | TTCACCGACATTCACGTGATG | SEQ ID NO: 29 | 1 | As | cucumber yellows virus (CuYV) | RNA1 |

TABLE 1-continued

DNA Sequences of small phloem RNA molecules.

| CLONE | SEQUENCE | SEQ ID NO: | # OF MISMATCHES | SENSE(s) ANTISENSE(s) | TYPE | GENE NAME |
|---|---|---|---|---|---|---|
| CuYV03 | TTCAACAAGTTGGTGGTTCTT | SEQ ID NO: 30 | 0 | s | cucumber yellows virus (CuYV) | RNA1 |
| CuYV05 | TTGAACCCTACAGTAAAAGAAG | SEQ ID NO: 31 | 0 | s | cucumber yellows virus (CuYV) | RNA1 |
| CuYV06 | TTGATCACCGTACTGCAGGAGT | SEQ ID NO: 32 | 0 | as | cucumber yellows virus (CuYV) | RNA1 |
| CuYV07 | TTGCTGACAGTAGTACGACAT | SEQ ID NO: 33 | 0 | as | cucumber yellows virus (CuYV) | RNA1 |
| CuYV10 | TGGAGGTAATTTCGGAAGGCA | SEQ ID NO: 34 | 0 | s | cucumber yellows virus (CuYV) | RNA1 |
| CuYV12 | TGAAATCAGTTTGCGATTCGT | SEQ ID NO: 35 | 1 | s | cucumber yellows virus (CuYV) | RNA1 |
| CuYV13 | TCAGTCGACATCGACCAAGAA | SEQ ID NO: 36 | 1 | s | cucumber yellows virus (CuYV) | RNA1 |
| CuYV15 | TCTTTGACAGGTCTTCTGAAA | SEQ ID NO: 37 | 0 | s | cucumber yellows virus (CuYV) | RNA1 |
| CuYV16 | TCGCATTGAACAGATTTGTGA | SEQ ID NO: 38 | 0 | as | cucumber yellows virus (CuYV) | RNA2 |
| CuYV17 | TATTCAGCATACGGGAATGAA | SEQ ID NO: 39 | 0 | as | cucumber yellows virus (CuYV) | RNA1 |
| CuYV18 | TAGGAACAAGCACAAGCGTA | SEQ ID NO: 40 | 0 | s | cucumber yellows virus (CuYV) | RNA1 |
| CuYV21 | ATGAACCGTCTGCAGCAGCGA | SEQ ID NO: 41 | 0 | s | cucumber yellows virus (CuYV) | RNA1 |
| CuYV22 | ATGTTCCTGGTATACTCCCT | SEQ ID NO: 42 | 0 | s | cucumber yellows virus (CuYV) | RNA1 |
| CuYV23 | ATTGCAACCCAGATATTTCT | SEQ ID NO: 43 | 0 | as | cucumber yellows virus (CuYV) | RNA2 RNA2 |
| CuYV24 | ATTGGAGAAGAAGCAGTCGA | SEQ ID NO: 44 | 1 | s | cucumber yellows virus (CuYV) | RNA1 |
| CuYV26 | AGATGTCCGTCACTCTTCAG | SEQ ID NO: 45 | 0 | as | cucumber yellows virus (CuYV) | RNA1 |
| CuYV27 | AGAGAAAGTCTAAAAGAGAGA | SEQ ID NO: 46 | 1 | as | cucumber yellows virus (CuYV) | RNA1 |
| CuYV29 | AGAACATTGAATCTGAGCGAA | SEQ ID NO: 47 | 1 | s | cucumber yellows virus (CuYV) | RNA1 RNA1 |
| CuYV31 | AGTCGGAAGTTGAGTACGGTA | SEQ ID NO: 48 | 0 | as | cucumber yellows virus (CuYV) | RNA1 |
| CuYV33 | AGTTTACGACATGACTTTACA | SEQ ID NO: 49 | 0 | as | cucumber yellows virus (CuYV) | RNA2 |
| CuYV34 | AGCGGTGACGATAGTTTGATCT | SEQ ID NO: 50 | 0 | s | cucumber yellows virus (CuYV) | RNA2 |
| CuYV36 | ACTCTTTTCGCAATAGTACCAACT | SEQ ID NO: 51 | 0 | S | cucumber yellows virus (CuYV) | RNA |
| uYV41 | CATCTTGCTGCCAAACATGGA | SEQ ID NO: 52 | 0 | S | cucumber yellows virus (CuYV) | RNA1 |
| CuYV43 | CATCGATGACTTGTGCGGCGC | SEQ ID NO: 53 | 0 | As | cucumber yellows virus (CuYV) | RNA1 |

TABLE 1-continued

DNA Sequences of small phloem RNA molecules.

| CLONE | SEQUENCE | SEQ ID NO: | # OF MISMATCHES | SENSE(s) ANTISENSE(s) | TYPE | GENE NAME |
|---|---|---|---|---|---|---|
| CuYV45 | CAGATTGCAAGTTTGGTCGA | SEQ ID NO: 54 | 0 | S | cucumber yellows virus (CuYV) | RNA2 |
| CuYV47 | CTACTGTCATCAAGAGTACGC | SEQ ID NO: 55 | 1 | S | cucumber yellows virus (CuYV) | RNA1 |
| CuYV48 | CTGACAAGTAAAGGACGTTGAAAG | SEQ ID NO: 56 | 0 | As | cucumber yellows virus (CuYV) | RNA1 |
| CuYV49 | CTGCGAATCCACCCATCGA | SEQ ID NO: 57 | 0 | S | cucumber yellows virus (CuYV) | RNA1 |
| CuYV50 | CTCTATCACGATGTAAAGGAAG | SEQ ID NO: 58 | 0 | S | cucumber yellows virus (CuYV) | RNA2 |
| CuYV51 | CGCCTGAGTAGAAAGGTGAGA | SEQ ID NO: 59 | 0 | As | cucumber yellows virus (CuYV) | RNA1 |
| CuYV52 | CGATCTCATTATTTGCTGCGA | SEQ ID NO: 60 | 0 | As | cucumber yellows virus (CuYV) | RNA1 |
| CuYV54 | CGTCGCACAAGTCATCGATGA | SEQ ID NO: 61 | 1 | S | cucumber yellows virus (CuYV) | RNA1 |
| CuYV55 | CGACATCGACCAAGAACTTGA | SEQ ID NO: 62 | 1 | S | cucumber yellows virus (CuYV) | RNA1 |
| CuYV59 | GAGAGCGGTTGTTGGATTTGA | SEQ ID NO: 63 | 0 | As | cucumber yellows virus (CuYV) | RNA1 |
| CuYV62 | GACTCTAAGGGCGAAAATAAAA | SEQ ID NO: 64 | 0 | As | cucumber yellows virus (CuYV) | RNA2 |
| TnL1/1 | TCCAATTGAAATGTCATCTC | SEQ ID NO: 65 | 0 | As | transposonlike | TnL1 |
| TnL1/2 | GCGCTCTCAGACACAAACCAA | SEQ ID NO: 66 | 0 | As | transposon-like | TnL1 |
| TnL1/3 | CTCGACCCAGACATGATGTCAG | SEQ ID NO: 67 | 0 | As | transposon-like | TnL1 |
| TnL1/4 | TGCGCTCTGACACACAAACCAA | SEQ ID NO: 68 | 0 | As | transposon-like | TnL1 |
| TnL1/5 | CCGGTGAGATACGATAAGTGGAA | SEQ ID NO: 69 | 1 | S | transposon-like | TnL1 |
| TnL1/6 | TCTCAAGGCTGTTGACATGGA | SEQ ID NO: 70 | 2 | As | transposon-like | TnL1 |
| TnL1/7 | TTGACATCATGTCTGGGTCGG | SEQ ID NO: 71 | 1 | S | transposon-like | TnL1 |
| TnL1/8 | CTACTCGACCCAGACATGATGT | SEQ ID NO: 72 | 0 | As | transposon-like | TnL1 |
| TnL1/9 | TGGAGAACGACGCGAGGTTCAA | SEQ ID NO: 73 | 0 | S | transposon-like | TnL1 |
| TnL1/10 | TACCGATCACATACGATACGTGG | SEQ ID NO: 74 | 2 | S | transposon-like | TnL1 |

TABLE 1-continued

DNA Sequences of small phloem RNA molecules.

| CLONE | SEQUENCE | SEQ ID NO: | # OF MISMATCHES | SENSE(s) ANTISENSE(s) | TYPE | GENE NAME |
|---|---|---|---|---|---|---|
| TnL1/11 | CAGGCCTCCTAGGAATACTCG | SEQ ID NO: 75 | 2 | S | transposon-like | TnL1 |
| TnL2/1 | GAAGGGTATTCAGCAGGTGA | SEQ ID NO: 76 | 0 | As | transposon-like | TnL2 |
| TnL2/2 | AAAAGAAGGTCGAAAGAAGA | SEQ ID NO: 77 | 2 | S | transposon-like | TnL2 |
| TnL2/3 | TTCAACTCGCCCATGAATTAA | SEQ ID NO: 78 | 2 | S | transposon-like | TnL2 |
| TnL2/4 | GAGGGGAGTGGGACGATTCG | SEQ ID NO: 79 | 1 | S | transposon-like | TnL2 |
| TnL2/5 | CGTGTTAATTGATGCATTGGG | SEQ ID NO: 80 | 1 | S | transposon-like | TnL2 |
| TnL2/6 | TCGTGACACTTCTTCTTTCGAC | SEQ ID NO: 81 | 1 | As | transposon-like | TnL2 |
| TnL2/7 | CGCAGCCCGTGCGGATCTATGG | SEQ ID NO: 82 | 0 | S | transposon-like | TnL2 |
| TnL2/8 | AGAGTACACAGTACGTTGACGA | SEQ ID NO: 83 | 1 | S | transposon-like | TnL2 |
| TnL2/9 | GGCAAGAGTACACCGTACGTTGA | SEQ ID NO: 84 | 0 | S | Transposon-like | TnL2 |
| TnL2/10 | GGATCTATGGAAAGAAGGTC | SEQ ID NO: 85 | 0 | S | Transposon-like | TnL2 |
| TnL2/11 | CATAGATCCGCACGGGCTGCGG | SEQ ID NO: 86 | 0 | As | Transposon-like | TnL2 |
| MT1 | GCGCGATTGGTTATCTGATTTGT | SEQ ID NO: 87 | 2 | S | Methyltransferase | MT1 |
| MT2 | TGGTGGCGCGATTGGTTATGTGA | SEQ ID NO: 88 | 2 | S | Methyltransferase | MT1 |
| MT3 | GGATAACCAATCGCGCCATCGAC | SEQ ID NO: 89 | 2 | As | Methyltransferase | MT1 |
| MT4 | GAGTGAAAATGGATTAACACCAA | SEQ ID NO: 90 | 1 | As | Methyltransferase | MT1 |
| MT5 | CCAGGGTTCGAACCCGTGAC | SEQ ID NO: 91 | 1 | As | Methyltransferase | MT1 |
| MT6 | CGGTGGCGCGATTGGTTTATCT | SEQ ID NO: 92 | 0 | S | Methyltransferase | MT1 |
| MT7 | GTGACCGTGGAGTTGAAATGGA | SEQ ID NO: 93 | 1 | As | Methyltransferase | MT1 |
| MT11 | CAGATAACCAATAGCGCCAGCGAC | SEQ ID NO: 94 | 1 | As | Methyltransferase | MT1 |
| End1 | GACGCTGGTGTTGAACTGGTTTA | SEQ ID NO: 95 | 0 | S | bifunctional endonuclease | End |
| End2 | CGCTGGTGTTGAAGTGGTTTACG | SEQ ID NO: 96 | 1 | S | bifunctional endonuclease | End |
| End3 | GACGCTGGTGTTGAACTGGTT | SEQ ID NO: 97 | 0 | S | bifunctional endonuclease | End |
| End4 | GTTGGTGTTGAACTGGTTTACAA | SEQ ID NO: 98 | 1 | S | bifunctional endonuclease | End |
| End5 | AACCAGTTCAACACCAGCGT | SEQ ID NO: 99 | 0 | As | bifunctional endonuclease | End |

TABLE 1-continued

DNA Sequences of small phloem RNA molecules.

| CLONE | SEQUENCE | SEQ ID NO: | # OF MISMATCHES | SENSE(s) ANTISENSE(s) | TYPE | GENE NAME |
|---|---|---|---|---|---|---|
| End6 | GCTGGTGTTGAACTGGTTTA | SEQ ID NO: 100 | 0 | S | bifunctional endonuclease | End |
| End8 | TCATTGTTTGGTTGTAAACGAGTT | SEQ ID NO: 101 | 1 | As | bifunctional endonuclease | End |
| End9 | AACCAGTTFCAATACCAGCGTGAC | SEQ ID NO: 102 | 1 | As | bifunctional endonuclease | End |
| End10 | GTAAACCAGTTCAACACTAGCGT | SEQ ID NO: 103 | 1 | As | bifunctional endonuclease | End |
| End11 | TGTTTGGTTGTAAACCAGTTCAA | SEQ ID NO: 104 | 1 | As | bifunctional endonuclease | End |
| End12 | TTGGTGTTGAAATGGTTTACAAC | SEQ ID NO: 105 | 2 | S | bifunctional endonuclease | End |
| Hel1 | ACAAATTGGGGAGGGGATTACAA | SEQ ID NO: 106 | 1 | S | DEAD/DEAH box RNA helicase | Hel |
| Hel2 | CTGGTTTACAACCAAACAATGAAAC | SEQ ID NO: 107 | 0 | S | DEAD/DEAH box RNA helicase | Hel |
| Hel3 | TCGGTATTTGTAATCCTCTTCC | SEQ ID NO: 108 | 1 | As | DEAD/DEAH box RNA helicase | Hel |
| Hel4 | TGGTGTTGAGCTGGTTTACAACC | SEQ ID NO: 109 | 0 | S | DEAD/DEAH box RNA helicase | Hel |
| Hel5 | CTGGTTTACAACCAAACAATGA | SEQ ID NO: 110 | 0 | S | DEAD/DEAH box RNA helicase | Hel |
| Hel7 | AGCGCAGCGGTTTCATTGTTTGGT | SEQ ID NO: 111 | 1 | As | DEAD/DEAH box RNA helicase | Hel |
| Hel8 | TCAACACCAGCGTCAGGAGTTCGA | SEQ ID NO: 112 | 1 | As | DEAD/DEAH box RNA helicase | Hel |
| Hel9 | CACCAGCGTCACGGGTTCGTGA | SEQ ID NO: 113 | 3 | As | DEAD/DEAH box RNA helicase | Hel |
| Hel10 | CTAGTTTACAACGAAACAATGA | SEQ ID NO: 114 | 1 | S | DEAD/DEAH box RNA helicase | Hel |
| Hel12 | TGTTTGGTTGTAAACCAGTTCAA | SEQ ID NO: 115 | 1 | As | DEAD/DEAH box RNA helicase | Hel |
| Hel13 | TTCGAACTCGTGACGCTGGTGT | SEQ ID NO: 116 | 1 | S | DEAD/DEAH box RNA helicase | Hel |
| Hel14 | CATCGAACCCGTGACGCTAGTGTT | SEQ ID NO: 117 | 3 | S | DEAD/DEAH box RNA helicase | Hel |
| Hel15 | GTTTCATTATTTGGTTGTAAA | SEQ ID NO: 118 | 1 | As | DEAD/DEAH box RNA helicase | Hel |
| Hel17 | TGGTTGTAAACCAGTTCAACAC | SEQ ID NO: 119 | 1 | As | DEAD/DEAH box RNA helicase | Hel |

TABLE 1-continued

DNA Sequences of small phloem RNA molecules.

| CLONE | SEQUENCE | SEQ ID NO: | # OF MISMATCHES | SENSE(s) ANTISENSE(s) | TYPE | GENE NAME |
|---|---|---|---|---|---|---|
| Hel18 | TGTTGAACTGGTTTACAACCAA | SEQ ID NO: 120 | 1 | S | DEAD/DEAH box RNA helicase | Hel |
| Hel19 | TCGAAACCGTGACGCTGGTGT | SEQ ID NO: 121 | 1 | S | DEAD/DEAH box RNA helicase | Hel |
| Hel22 | CGCAGTGATTTCATTGTTTGGT | SEQ ID NO: 122 | 1 | As | DEAD/DEAH box RNA helicase | Hel |
| Hel16 | TGTTTGGTTGTAAATCAGTTCAAC | SEQ ID NO: 123 | 2 | As | DEAD/DEAH box RNA helicase | Hel |
| Hel21 | GAGGATTACAATACCGACTCTTTC | SEQ ID NO: 124 | 1 | S | DEAD/DEAH box RNA helicase | Hel |
| miR156 | TGACAGAAGAGAGTGAGCAC | SEQ ID NO: 125 | | | | |
| miR159 | TTTGGATTGAAGGGAGCTCTA | SEQ ID NO: 126 | | | | |
| miR167 | TCAAGCTGCCAGCATGATCTGA | SEQ ID NO: 127 | | | | |
| miR171 | GATTGAGCCGCGCCAATATC | SEQ ID NO: 128 | | | | |

TABLE 2

Bioinformatically identified Arabidopsis miRNA cloned from cucurbit phloem sap. Cloned and sequenced phloem sap small RNA were analyzed by conducting FASTA analyses with each sequence and its reverse complement against proprietary ESTs [Genesis Research and Development Corporation plant consensi including sequences from: *Actinidia*, *Cucurbita*, *Eucalyptus*, *Festuca*, *Lolium*, *Malus domestica*, *Pinus radiata* and *Vaccinium*] and public plant databases [TIGR Gene Indices (available online) including: *Chlamydomonas reinhardtii*, *Glycine max*, *Gossypium*, *Lycopersicon esculentum*, *Medicago truncatula*, *Pinus taeda*, *Triticum aestivum*, *Vitis vinifera*, *Zea mays*]. Sequences within each of these datasets were then mapped by TBLASTX against Arabidopsis genes.

| microRNA | Sequence | Databases with FASTA hits | No. of mis-matches[a] | Di-rection | Arabidopsis best bit | Description Line[b] | Target gene family |
|---|---|---|---|---|---|---|---|
| miR156[c,d,e,g] | TGACAGAAGAGA GTGAGCAC | *Actinidia* *Arabidopsis* *Populus* | 1 | R | At1g69170 | squamosa-promoter binding protein-related, similar to squamosa-promoter binding protein 1 GI:1183865 from (*Antirrhinum majus*) | SQUAMOSA-PROMOTER BINDING PROTEIN (SBP-like proteins) |
| | | *Actinidia* *Arabidopsis* *Eucalyptus* *Glycine* *Gossypium* *Malus* *Zea* | 1 | R | At2g42200 | squamosa-promoter binding protein-related | SBP-like proteins |
| | | *Arabidopsis* *Eucalyptus* *Populus* | 1 | R | At5g50670 | expressed protein, contains similarity to squamosa promoter binding protein | SBP-like proteins |
| | | *Arabidopsis* *Eucalyptus* *Pinus* *Triticum* *Vitis* | 1 to 2 | R | At5g43270 | squamosa promoter binding protein-related 2 (emb|CAB56576.1) | SBP-like proteins |

TABLE 2-continued

Bioinformatically identified Arabidopsis miRNA cloned from cucurbit phloem sap. Cloned and sequenced phloem sap small RNA were analyzed by conducting FASTA analyses with each sequence and its reverse complement against proprietary ESTs [Genesis Research and Development Corporation plant consensi including sequences from: *Actinidia, Cucurbita, Eucalyptus, Festuca, Lolium, Malus domestica, Pinus radiata* and *Vaccinium*] and public plant databases [TIGR Gene Indices (available online) including: *Chlamydomonas reinhardtii, Glycine max, Gossypium, Lycopersicon esculentum, Medicago truncatula, Pinus taeda, Triticum aestivum, Vitis vinifera, Zea mays*]. Sequences within each of these datasets were then mapped by TBLASTX against Arabidopsis genes.

| microRNA | Sequence | Databases with FASTA hits | No. of mis-matches[a] | Di-rection | Arabidopsis best bit | Description Line[b] | Target gene family |
|---|---|---|---|---|---|---|---|
|  |  | *Glycine Lolium Medicago Pinus Zea* | 1 to 3 | R | At1g53160 | transcription factor-related, similar to GB:X92369 from (*Antirrhinum majus*) | SBP-like proteins |
|  |  | *Actinidia Eucalyptus Lycopersicon Populus Vaccinium* | 2 to 3 | R | At3g15270 | squamosa promoter binding protein-related 5, identical to GB:CAB56571 from (*Arabidopsis thaliana*) | SBP-like proteins |
| miR159[c,d,g] | TTTGGATTGAAG GGAGGTCTA | *Arabidopsis Festuca Populus Triticum* | 2 to 3 | R | At5g06100 | myb family transcription factor, contains Pfam profile: PF00249 myb DNA-binding domain | MYB transcription factors |
|  |  | *Arabidopsis Populus Vitis* | 3 | R | At3g11440 | myb family transcription factor, contains Pfam profile: PF00249 myb-like DNA-binding domain | MYB transcription factors |
| similar to miR167[c,d,e,g] | TCAAGCTGCCAG CATGATCTGA | *Actinidia Arabidopsis Eucalyptus Glycine Lolium Malus Medicago Pinus Populus Triticum Vaccinium Zea* | 3 | R | At1g30330 | ARF6 (ARF6) mRNA | Auxin Response Factors |
|  |  | *Arabidopsis Glycine Medicago* | 3 | R | At5g37020 | auxin response factor 8 (ARF8) mRNA | Auxin Response Factors |
|  |  | *Actinidia* | 0 | R | At4g00150 | scarecrow-like transcription factor 6 (SCL6) | GRAS domain transcription factors (SCARECROW-like) |
| miR171[c,f,h] | GATTGAGCCGCG CCAATATC | *Arabidopsis Glycine Lotus Medicago Pinus Populus Zea* |  |  |  |  |  |
|  |  | *Cucurbita Eucalyptus Glycine Lotus Lycopersicon Populus* | 0 to 3 | R | At4g36710 | scarecrow transcription factor family | GRAS domain transcription factors (SCARECROW-like) |

[a]Bulges and G:U wobbles are included as mismatches in this analysis.
[b]Description lines taken from TAIR (http://www.arabidopsis.org/info/ontologies)
[c]Reinhart et al. (2002)
[d]Rhoades et al. (2002)
[e]Kasschau et al. (2003)
[f]Llave et al. (2002)
[g]phloem-mobile
[h]not detected in phloem

TABLE 3

CmPSRB1 mediates form-specific cell-to-cell movement of small RNA.

| | Microinjection | |
|---|---|---|
| Injected material* | Total (n) | Movement [n (%)]† |
| 21 nt ssRNA | 10 | 0 (0) |
| 25 nt ssRNA | 35 | 0 (0) |
| 25 nt dsRNA (3' 2 nt overhang) | 8 | 0 (0) |
| 25 nt dsRNA (5' 2 nt overhang) | 8 | 0 (0) |
| R-KN1 + 20 kD FITC-dextran | 26 | 24 (96)# |
| R-KN1 + 25 nt ssRNA | 6 | 0 (0) |
| R-KN1 + 20 kD FITC-dextran + 25 nt ssRNA | 5 | 5/0 (100/0)** |
| Phloem fraction 7 + 25 nt ssRNA | 13 | 8 (62)‡ |
| Phloem fraction 10 + 25 nt ssRNA | 8 | 1 (13) |
| Phloem-purified CmPSRB1 + 25 nt ssRNA | 6 | 5 (83)‡ |
| R-CmPSRB1 + 25 nt ssRNA | 26 | 20 (80)‡ |
| R-CmPSRB1 + 20 kD FITC-dextran | 11 | 11 (100)‡ |
| R-CmPSRBP1 + 20 kD FITC-dextran + 25 nt ssRNA | 5 | 5/5 (100/100) |
| R-CmPSRB1 + CmRINGP RNA (1 kb) | 8 | 0 (0) |
| R-CmPSRB1 + 25 nt dsRNA (3' 2 nt overhang) | 5 | 0 (0) |
| R-CmPSRB1 + 25 nt ssDNA | 14 | 0 (0) |

*All RNA/DNA probes used were labeled with Alexa Fluor 568 (red) or 488 (green) and injected at 1 µg/µl concentration; Fluorescein isothiocyanate (FITC)-labeled 20 kDa dextran was used as fluorescent reporter to test the PD SEL in response to injected proteins; R-KN1 and R-CmPSRB1 were expressed in *E. coli*, purified and used in microinjection studies at 1.5 µg/µl; phloem fractions 7 & 10 used at 0.1 µg/µl (26).
†Number of injections, and percent of total injections, in which probe moved from the target cell.
Control condition in which probe moved radially out through 4–5 cells.
**Co-injection experiments in which R-KN1 potentiated extensive trafficking of 20 kDa FITC-dextran but not Alexa Fluor 568-labeled 25 nt ssRNA.
‡Movement of the RNA probe (or 20 kDa FITC-dextran) was restricted to neighboring cells and the small RNA signal very often accumulated in their nuclei.

TABLE 4

Plasmodesmal trafficking of KN1 and Cucumber mosaic virus movement protein (CMV-MP) mediates cell-to-cell movement of RNA transcripts, but not various forms of 25 nt small RNA.

| | Microinjection | |
|---|---|---|
| Injected material* | Total (n) | Movement [n (%)]† |
| LYCH | 10 | 10 (100) |
| FITC-dextran (20 kDa) | 30 | 3 (10) |
| BSA + 25 nt ssRNA | 8 | 0 (0) |
| BSA + 25 nt ssDNA | 8 | 0 (0) |
| 25 nt dsRNA (blunt ended) | 10 | 0 (0) |
| 21–25 nt dsRNA (3' 4 nt overhang) | 10 | 0 (0) |
| Phloem fraction 7 + 25 nt dsRNA (blunt) | 10 | 0 (0) |
| Phloem fraction 10 + 25 nt dsRNA (blunt) | 9 | 1 (11) |
| R-KN1 + KN1 RNA (sense) | 22 | 20 (91)** |
| R-KN1 + KN1 RNA (antisense) | 10 | 2 (20)** |
| R-KN1 + CmRINGP RNA (sense, 1 kb) | 12 | 0 (0) |
| R-CMV-MP + FITC-dextran (20 kDa) | 10 | 10 (100) |
| R-CMV-MP + CmRINGP RNA (sense, 1 kb) | 10 | 10 (100) |
| R-CMV-MP + 25 nt ssRNA | 10 | 0 (0) |
| R-CMV-MP + FITC-dextran (20 kDa) + 25 nt ssRNA | 13 | 13/0 (100/0)# |
| R-CMV-MP + FITC-dextran (20 kDa) + 25 nt dsRNA | 13 | 12/0 (92/0)# |

*Fluorescent probes were as follows: LYCH, Lucifer yellow CH (small control probe that diffuses through PD microchannels); FITC-dextran, fluorescein isothiocyanate-labeled dextran (used as a fluorescent reporter to test the PD SEL in response to injected proteins); RNA/DNA Probes, Alexa Fluor 568-labeled nucleic acids injected at 1 µg/µl concentration. BSA was used to test for any non-specific effects that could be associated with injection of protein, per se, into the target cell. Phloem fraction 7/10 aliquots, 0.1 µg/µl; native R-KN1 and R-CMV-MP, 1.5 µg/µl.
†Number of injections and percent of total injections in which the probe moved into surrounding mesophyll cells within mature leaves of *Nicotiana benthamiana* plants. A minimum of 5 plants were used to test the movement of each probe.
**Data included from our previous studies in which R-KN1 was shown to mediate extensive cell-to-cell movement of its own sense but not antisense transcripts (S13).
Co-injection experiments in which R-CMV-MP potentiated trafficking of 20 kDa FITC-dextran but not Alexa Fluor 568-labeled 25 nt ss- or dsRNA.

The following references cited in the "Background of the Invention" are hereby incorporated by reference in their entirety.
1. R. A. Jorgensen, R. G. Atkinson, R. L. S. Forster, W. J. Lucas, *Science* 279, 1486 (1998).
2. Fire et al., *Nature* 391, 806 (1998); G. J. Hannon, *Nature* 418, 244 (2002); W. M. Winston, C. Molodowitch, C. P. Hunter, *Science* 295, 2456 (2002); Poignant et al., *RNA* 9, 299 (2003).
3. W. J. Lucas, B.-C. Yoo, F. Kragler, *Nat. Rev. Mol. Cell Biol.* 2, 849 (2001).
4. X. Wu, D. Weigel, P. A. Wigge, *Genes Dev.* 16, 151 (2002).
5. J.-C. Palauqui, T. Elmayan, J.-M. Pollien, H. Vaucheret, *EMBO J.* 16, 4738 (1997).
6. O. Voinnet, P. Vain, S. Angell, D. C. Baulcombe, *Cell* 95, 177 (1998).
7. M. Fagard, H. Vaucheret, *Annu Rev. Plant Physiol. Plant Mol. Biol.* 51, 167 (2000); V. Vance, H. Vaucheret, *Science* 292, 2277 (2001); S. Mlotshwa et al., *Plant Cell* 14, S289 (2002).
8. B. Xoconostle-Cázares et al., *Science* 283, 94 (1999).
9. R. Ruiz-Medrano, B. Xoconostle-Cázares, W. J. Lucas, *Development* 126, 4405 (1999).
10. M. Kim, W. Canio, S. Kessler, N. Sinha, *Science* 293, 287 (2001).
11. P. Zambryski, K. Crawford, *Annu. Rev. Cell Dev. Biol.* 16, 393 (2000); D. Jackson, *Plant Cell* 13, 2669 (2001); V. Haywood, F. Kragler, W. J. Lucas, *Plant Cell* 14, S303 (2002).
12. W. J. Lucas et al., *Science* 270, 1980 (1995); J. Y. Kim, Z. A. Yuan, M. Cilia, Z. Khalfan-Jagani, D. Jackson, *Proc. Natl. Acad. Sci. USA* 99, 4103 (2002).
13. A. Sessions, M. F. Yanofsky, D. Weigel, *Science* 289, 779 (2000).
14. K. Nakajima, G. Sena, T. Nawy, P. N. Benfey, *Nature* 413, 307 (2001).
15. T. Wada et al., *Development* 129, 5409 (2002); J. Schiefelbein, *Curr. Opin. Plant Biol.* 6, 74 (2003).
16. S. Balachandran, Y. Xiang, C. Schobert, G. A. Thompson, W. J. Lucas, *Proc. Natl. Acad. Sci. U.S.A.* 94, 14150 (1997); K. Aoki, F. Kragler, B. Xoconostle-Cázares, W. J. Lucas, *Proc. Natl. Acad. Sci. USA* 99, 16342 (2002); A. J. E. van Bel, *Plant Cell Environ.* 26, 126 (2003).
17. T. Dalmay, A. J. Hamilton, S. Rudd, S. Angell, D. C. Baulcombe, *Cell* 101, 543 (2000); P. Mourrain et al., *Cell* 101, 533 (2000); T. D. Dalmay, R. Horsefield, T. H. Braunstein, D. C. Baulcombe, *EMBO J.* 20, 2069 (2001); T. Sijen et al., *Cell* 107, 465 (2001); G. Tang, B. J. Reinhart, D. P. Bartel, P. D. Zamore, *Genes Dev.* 17, 49 (2003).
18. S. M. Hammond, E. Bernstein, D. Beach, G. Hammon, *Nature* 404, 293 (2000); E. Bernstein, A. A. Caudy, S. M. Hammond, G. J. Hannon, *Nature* 409, 363 (2001).
19. A. J. Hamilton, D. C. Baulcombe, *Science* 286, 950 (1999); P. D. Zamore, T. Tuschl, P. A. Sharp, D. P. Bartel, *Cell* 101, 26 (2000); S. M. Elbashir, W. Lendeckel, T. Tuschl, *Genes Dev.* 15, 188 (2001).
20. P. H. Olsen, V. Ambros, *Dev. Biol.* 216, 671 (1999); G. Hutvagner et al., *Science* 293, 834 (2001); G. Hutvagner, P. D. Zamore, *Science* 297, 2056 (2002).
21. C. Llave, K. D. Kasschau, M. A. Rector, J. C. Carrington, *Plant Cell* 14, 1605 (2002). B. J. Reinhart, E. G. Weinstein, M. W. Rhoades, B. Bartel, D. P. Bartel, *Genes Dev.* 16, 1616 (2002).
22. A. J. Hamilton, O. Voinnet, L. Chappell, D. C. Baulcombe, *EMBO J.* 21, 4671 (2002).
23. A. C. Mallory et al., *Plant Cell* 13, 571 (2001).
24. H. S. Gou, S. W. Ding, *EMBO J.* 21, 398 (2002).
25. B.-C. Yoo, J. Y Lee, W. J. Lucas, *J Biol. Chem.* 277, 15326 (2002).
26. S. Z. Pang et al., *Mol. Breeding* 6, 87 (2000).
27. R. L. Gilbertson, W. J. Lucas, *Trends Plant Sci.* 1, 260 (1996); J. C. Carrington, K. D. Kasschau, S. K. Mahajan, M. C. Schaad, *Plant Cell* 8, 1669 (1996).
28. O. Voinnet, *Trends Genet.* 17, 449 (2001).
29. S. Hartono, T. Natsuaki, Y. Genda, S. Okuda, *J. Gen. Virol.* 84, 1007 (2003).
30. M. J. Havey, J. D. McCreight, B. Rhodes, G. Taurick, *Theor. Applied Genet.* 97, 122 (1998).
31. A. W. Robards, W. J. Lucas, *Annu Rev. Plant Phys. Plant Mol. Biol.* 41, 369 (1990).
32. M. Matzke, A. J. M. Matzke, J. M. Kooter, *Science* 293, 1080 (2001); C. Llave, Z. X. Xie, K. D. Kasschau, J. C. Carrington, *Science* 297, 2053 (2002); T. A. Volpe et al., *Science* 297, 1833 (2002).
33. I. Kovalchuk et al., *Nature* 423, 761 (2003).

What is claimed:

1. An isolated nucleic acid, wherein said nucleic acid comprises a nucleotide sequence encoding the phloem small RNA binding protein of SEQ ID NO: 2.

2. An isolated nucleic acid, wherein said nucleic acid comprises SEQ ID NO: 1.

3. A transgenic plant expressing the nucleic acid molecule of claim 1.

4. A nucleic acid construct comprising the nucleic acid of claim 1 operatively linked to a promoter.

5. The nucleic acid construct of claim 4 wherein the promoter is selected from the group consisting of constitutive promoters, inducible promoters, tissue- and cell-specific promoters, and developmentally-regulated promoters.

6. A transgenic plant expressing the nucleic acid of claim 2.

7. A nucleic acid construct comprising the nucleic acid of claim 2 operatively linked to a promoter.

8. The nucleic acid construct of claim 7 wherein the promoter is selected from the group consisting of constitutive promoters, inducible promoters, tissue- and cell-specific promoters, and developmentally-regulated promoters.

* * * * *

UNITED STATES PATENT AND TRADEMARK OFFICE
CERTIFICATE OF CORRECTION

PATENT NO. : 7,189,892 B2 Page 1 of 1
APPLICATION NO. : 10/871841
DATED : March 13, 2007
INVENTOR(S) : William J. Lucas et al.

It is certified that error appears in the above-identified patent and that said Letters Patent is hereby corrected as shown below:

At column 81, line 64, bottom of page, claim 3, delete "molecule"

Signed and Sealed this

Tenth Day of July, 2007

JON W. DUDAS
*Director of the United States Patent and Trademark Office*

SEQUENCE LISTING

```
<160> NUMBER OF SEQ ID NOS: 128

<210> SEQ ID NO 1
<211> LENGTH: 870
<212> TYPE: DNA
<213> ORGANISM: Cucurbita maxima

<400> SEQUENCE: 1
tctaatcttt gcatccatgg cgtctttcca atgcaacaaa ccggctgagc gcagccacca      60
ccagaggcac gatcaatgcc atcaggaaca ccaacaccat cacggccacg gtccggcggg     120
gggtcacggc cacggtccgg cgtggggtca cggccacggt ccgtcggggg gtcacggctg     180
cggtccgtcg gggggtcacg gccacggtcc gtcgggggt cacggccacg gtccgtcggg     240
gggtcacggc cacggtccgg cgtggggtca cggccacggt ccgtcggggg gtcacggctg     300
cggtccgtcg gggggtcacg gccacggtcc gtcgggggt cacggccacg gtccgtcggg     360
```

```
gggtcacggc cacggtccgt cgggggggtca cggccacggt ccgtcggggg gtcatggcca    420
cggtccggcg tgggtcacg gccacggtcc gtcgggggt cacggctgcg gtccggcggg       480
gggtcacggc cacggtcctg cggggggggca aggccactgc cagccagcca atcccaatgt    540
cggacactgc cagccagcca atcccaacgt cggccactgc cagccagcca gtcccaatgt    600
cggccaccac agcgacagca gtgacagtga caacgattgt cgcagaggtc agcactaaag    660
gaagaattgg aaggaggaag tggaagggta cttgctagat tgaagggaag ggaatcagag    720
agtgcatcta aactgctact gatactccta ctactaagta ttcgagtgac gcctaaaata    780
aataagacaa tttataagac accctaactt tatctccttt tccttctttc aaataaagtt    840
tctgtattgc taaaaaaaaa aaaaaaaaaa                                      870
```

<210> SEQ ID NO 2
<211> LENGTH: 213
<212> TYPE: PRT
<213> ORGANISM: Cucurbita maxima

<400> SEQUENCE: 2

```
Met Ala Ser Phe Gln Cys Asn Lys Pro Ala Glu Arg Ser His His Gln
 1               5                   10                  15

Arg His Asp Gln Cys His Gln Glu His Gln His His Gly His Gly
                20                  25                  30

Pro Ala Gly Gly His Gly His Gly Pro Ala Trp Gly His Gly His Gly
            35                  40                  45

Pro Ser Gly Gly His Gly Cys Gly Pro Ser Gly Gly His Gly His Gly
        50                  55                  60

Pro Ser Gly Gly His Gly His Gly Pro Ser Gly Gly His Gly His Gly
65                  70                  75                  80

Pro Ala Trp Gly His Gly His Gly Pro Ser Gly Gly His Gly Cys Gly
                85                  90                  95

Pro Ser Gly Gly His Gly His Gly Pro Ser Gly Gly His Gly His Gly
            100                 105                 110

Pro Ser Gly Gly His Gly His Gly Pro Ser Gly Gly His Gly His Gly
        115                 120                 125

Pro Ser Gly Gly His Gly His Gly Pro Ala Trp Gly His Gly His Gly
    130                 135                 140

Pro Ser Gly Gly His Gly Cys Gly Pro Ala Gly Gly His Gly His Gly
145                 150                 155                 160

Pro Ala Gly Gly Gln Gly His Cys Gln Pro Ala Asn Pro Asn Val Gly
                165                 170                 175

His Cys Gln Pro Ala Asn Pro Asn Val Gly His Cys Gln Pro Ala Ser
            180                 185                 190

Pro Asn Val Gly His His Ser Asp Ser Ser Asp Ser Asp Asn Asp Cys
        195                 200                 205

Arg Arg Gly Gln His
    210
```

<210> SEQ ID NO 3
<211> LENGTH: 20
<212> TYPE: RNA
<213> ORGANISM: Artificial Sequence
<220> FEATURE:
<223> OTHER INFORMATION: Artificially Synthesized RNA Probe

<400> SEQUENCE: 3

```
cagugucuuc ucccucacug                                              20

<210> SEQ ID NO 4
<211> LENGTH: 25
<212> TYPE: RNA
<213> ORGANISM: Artificial Sequence
<220> FEATURE:
<223> OTHER INFORMATION: Artificially Synthesized RNA Probe

<400> SEQUENCE: 4
cagugucuuc ucccucacug cuacu                                        25

<210> SEQ ID NO 5
<211> LENGTH: 21
<212> TYPE: RNA
<213> ORGANISM: Artificial Sequence
<220> FEATURE:
<223> OTHER INFORMATION: Artificially Synthesized RNA Probe

<400> SEQUENCE: 5
gcagugaggg agaagacacu g                                            21

<210> SEQ ID NO 6
<211> LENGTH: 25
<212> TYPE: RNA
<213> ORGANISM: Artificial Sequence
<220> FEATURE:
<223> OTHER INFORMATION: Artificially Synthesized RNA Probe

<400> SEQUENCE: 6
ggaaaacuac cuguuccaug gccaa                                        25

<210> SEQ ID NO 7
<211> LENGTH: 25
<212> TYPE: RNA
<213> ORGANISM: Artificial Sequence
<220> FEATURE:
<223> OTHER INFORMATION: Artificially Synthesized RNA Probe

<400> SEQUENCE: 7
uguuggccau ggaacaggua guuuu                                        25

<210> SEQ ID NO 8
<211> LENGTH: 25
<212> TYPE: RNA
<213> ORGANISM: Artificial Sequence
<220> FEATURE:
<223> OTHER INFORMATION: Artificially Synthesized RNA Probe

<400> SEQUENCE: 8
uuggccaugg aacagguagu uuucc                                        25

<210> SEQ ID NO 9
<211> LENGTH: 25
<212> TYPE: RNA
<213> ORGANISM: Artificial Sequence
<220> FEATURE:
<223> OTHER INFORMATION: Artificially Synthesized RNA Probe

<400> SEQUENCE: 9
ggccauggaa cagguaguuu uccag                                        25

<210> SEQ ID NO 10
<211> LENGTH: 27
<212> TYPE: DNA
<213> ORGANISM: Artificial Sequence
```

```
<220> FEATURE:
<223> OTHER INFORMATION: Artificially Synthesized Primer Sequence

<400> SEQUENCE: 10
atgggtttga agaagccaag ccactta                                    27

<210> SEQ ID NO 11
<211> LENGTH: 26
<212> TYPE: DNA
<213> ORGANISM: Artificial Sequence
<220> FEATURE:
<223> OTHER INFORMATION: Artificially Synthesized Primer Sequence

<400> SEQUENCE: 11
ttgtcgaagc caatgactct gatgaa                                     26

<210> SEQ ID NO 12
<211> LENGTH: 31
<212> TYPE: DNA
<213> ORGANISM: Artificial Sequence
<220> FEATURE:
<223> OTHER INFORMATION: Artificially Synthesized Primer Sequence

<400> SEQUENCE: 12
catggagcta gatcttgcgc aactttctct g                               31

<210> SEQ ID NO 13
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 13
gtggtaaagg acttcaagcc cacgacc                                    27

<210> SEQ ID NO 14
<211> LENGTH: 24
<212> TYPE: DNA
<213> ORGANISM: Artificial Sequence
<220> FEATURE:
<223> OTHER INFORMATION: Artificially Synthesized Primer Sequence

<400> SEQUENCE: 14
atggcttcca tcgtctcatc cgcc                                       24

<210> SEQ ID NO 15
<211> LENGTH: 31
<212> TYPE: DNA
<213> ORGANISM: Artificial Sequence
<220> FEATURE:
<223> OTHER INFORMATION: Artificially Synthesized Primer Sequence

<400> SEQUENCE: 15
catggtacag cagcttggaa cttatattcc a                               31

<210> SEQ ID NO 16
<211> LENGTH: 25
<212> TYPE: DNA
<213> ORGANISM: Artificial Sequence
<220> FEATURE:
<223> OTHER INFORMATION: Artificially Synthesized Primer Sequence

<400> SEQUENCE: 16
cactgctgat ttgatggaat ccacg                                      25
```

<210> SEQ ID NO 17
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 17
aactcgatgt cgcctcctcg tggctta                                27

<210> SEQ ID NO 18
<211> LENGTH: 21
<212> TYPE: DNA
<213> ORGANISM: Artificial Sequence
<220> FEATURE:
<223> OTHER INFORMATION: Artificially Synthesized Primer Sequence

<400> SEQUENCE: 18
gctgcgtcag ctagaataga c                                      21

<210> SEQ ID NO 19
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 19
aggtggattt aaagtatttc cagccac                                27

<210> SEQ ID NO 20
<211> LENGTH: 15
<212> TYPE: PRT
<213> ORGANISM: Cucurbita maxima
<220> FEATURE:
<221> NAME/KEY: VARIANT
<222> LOCATION: 4
<223> OTHER INFORMATION: Xaa=Gly or Ser
<220> FEATURE:
<221> NAME/KEY: VARIANT
<222> LOCATION: 5
<223> OTHER INFORMATION: Xaa=Pro or His
<220> FEATURE:
<221> NAME/KEY: VARIANT
<222> LOCATION: 7
<223> OTHER INFORMATION: Xaa=Pro or His
<220> FEATURE:
<221> NAME/KEY: VARIANT
<222> LOCATION: 9
<223> OTHER INFORMATION: Xaa=Gly or His
<220> FEATURE:
<221> NAME/KEY: VARIANT
<222> LOCATION: 11
<223> OTHER INFORMATION: Xaa=His or Pro
<220> FEATURE:
<221> NAME/KEY: VARIANT
<222> LOCATION: 12
<223> OTHER INFORMATION: Xaa=Gly or Ser

<400> SEQUENCE: 20

His Gly Pro Xaa Xaa Gly Xaa Ala Xaa Gly Xaa Xaa Gly Pro Ala
 1               5                  10                  15

<210> SEQ ID NO 21
<211> LENGTH: 14
<212> TYPE: PRT
<213> ORGANISM: Cucurbita maxima
<220> FEATURE:
<221> NAME/KEY: VARIANT
<222> LOCATION: 5

<223> OTHER INFORMATION: Xaa=Ala or Ser
<220> FEATURE:
<221> NAME/KEY: VARIANT
<222> LOCATION: 11
<223> OTHER INFORMATION: Xaa=Gly or His
<220> FEATURE:
<221> NAME/KEY: VARIANT
<222> LOCATION: 13
<223> OTHER INFORMATION: Xaa=Ala or Ser

<400> SEQUENCE: 21

Gly His Gly Pro Xaa Gly Gly His Gly His Xaa Pro Xaa Ala
 1               5                  10

<210> SEQ ID NO 22
<211> LENGTH: 29
<212> TYPE: DNA
<213> ORGANISM: Cucurbita maxima
<220> FEATURE:
<221> NAME/KEY: misc_feature
<222> LOCATION: 3,9,12,15,18,21, 27
<223> OTHER INFORMATION: n=inosine

<400> SEQUENCE: 22
ggncayggnc cngcnggngg ncayggnca                              29

<210> SEQ ID NO 23
<211> LENGTH: 33
<212> TYPE: DNA
<213> ORGANISM: Cucurbita mxima
<220> FEATURE:
<221> NAME/KEY: misc_feature
<222> LOCATION: 6,9,12,18,21,24,27,30
<223> OTHER INFORMATION: n=inosine

<400> SEQUENCE: 23
cayggnccng gnccnggncc ngcngggnggn cay                        33

<210> SEQ ID NO 24
<211> LENGTH: 33
<212> TYPE: DNA
<213> ORGANISM: cucurbita maxima

<400> SEQUENCE: 24
ctaatctttg catccatggc gtctttccaa tgc                         33

<210> SEQ ID NO 25
<211> LENGTH: 32
<212> TYPE: DNA
<213> ORGANISM: Cucurbita maxima

<400> SEQUENCE: 25
ttagtgctga cctctgcgac aatcgttgtc ac                          32

<210> SEQ ID NO 26
<211> LENGTH: 27
<212> TYPE: DNA
<213> ORGANISM: Cucurbita maxima

<400> SEQUENCE: 26
gtggtaaagg acttcaagcc cacgacc                                27

<210> SEQ ID NO 27
<211> LENGTH: 27
<212> TYPE: DNA
<213> ORGANISM: Cucurbita maxima -continued

```
<400> SEQUENCE: 27
atgggtttga agaagccaag ccactta                                         27

<210> SEQ ID NO 28
<211> LENGTH: 21
<212> TYPE: DNA
<213> ORGANISM: Cucurbita maxima

<400> SEQUENCE: 28
ttctgtcgtt ccactttgca a                                               21

<210> SEQ ID NO 29
<211> LENGTH: 21
<212> TYPE: DNA
<213> ORGANISM: Cucurbita maxima

<400> SEQUENCE: 29
ttcaccgaca ttcacgtgat c                                               21

<210> SEQ ID NO 30
<211> LENGTH: 21
<212> TYPE: DNA
<213> ORGANISM: Cucurbita maxima

<400> SEQUENCE: 30
ttcaacaagt tggtggttct t                                               21

<210> SEQ ID NO 31
<211> LENGTH: 22
<212> TYPE: DNA
<213> ORGANISM: Cucurbita maxima

<400> SEQUENCE: 31 ttgaaccta cagtaaaaga ag                                               22

<210> SEQ ID NO 32
<211> LENGTH: 22
<212> TYPE: DNA
<213> ORGANISM: Cucurbita maxima

<400> SEQUENCE: 32
ttgatcaccg tactgcagga gt                                              22

<210> SEQ ID NO 33
<211> LENGTH: 21
<212> TYPE: DNA
<213> ORGANISM: Cucurbita maxima

<400> SEQUENCE: 33
ttgctgacag tagtacgaca t                                               21

<210> SEQ ID NO 34
<211> LENGTH: 21
<212> TYPE: DNA
<213> ORGANISM: Cucurbita maxima

<400> SEQUENCE: 34
tggaggtaat ttcggaaggc a                                               21

<210> SEQ ID NO 35
<211> LENGTH: 21
<212> TYPE: DNA
<213> ORGANISM: Cucurbita maxima
```

```
<400> SEQUENCE: 35
tgaaatcagt ttgcgattcg t                                              21

<210> SEQ ID NO 36
<211> LENGTH: 21
<212> TYPE: DNA
<213> ORGANISM: Cucurbita maxima

<400> SEQUENCE: 36
tcagtcgaca tcgaccaaga a                                              21

<210> SEQ ID NO 37
<211> LENGTH: 21
<212> TYPE: DNA
<213> ORGANISM: Cucurbita maxime

<400> SEQUENCE: 37
tctttgacag gtcttctgaa a                                              21

<210> SEQ ID NO 38
<211> LENGTH: 21
<212> TYPE: DNA
<213> ORGANISM: Cucurbita maxima

<400> SEQUENCE: 38
tcgcattgaa cagatttgtg a                                              21

<210> SEQ ID NO 39
<211> LENGTH: 20
<212> TYPE: DNA
<213> ORGANISM: Cucurbita maxima

<400> SEQUENCE: 39
tattcagcat acgggaatga                                                20

<210> SEQ ID NO 40
<211> LENGTH: 20
<212> TYPE: DNA
<213> ORGANISM: Cucurbita maxima

<400> SEQUENCE: 40
taggaacaag cacaagcgta                                                20

<210> SEQ ID NO 41
<211> LENGTH: 21
<212> TYPE: DNA
<213> ORGANISM: Cucurbita maxima

<400> SEQUENCE: 41
atgaaccgtc tgcagcagcg a                                              21

<210> SEQ ID NO 42
<211> LENGTH: 20
<212> TYPE: DNA
<213> ORGANISM: Cucurbita maxima

<400> SEQUENCE: 42
atgttcctgg tatactccct                                                20

<210> SEQ ID NO 43
<211> LENGTH: 20
<212> TYPE: DNA
```

-continued

<213> ORGANISM: Cucurbita maxima

<400> SEQUENCE: 43
attgcaaccc agatatttct                                          20

<210> SEQ ID NO 44
<211> LENGTH: 20
<212> TYPE: DNA
<213> ORGANISM: Cucurbita maxima

<400> SEQUENCE: 44
attggagaag aagcagtcga                                          20

<210> SEQ ID NO 45
<211> LENGTH: 20
<212> TYPE: DNA
<213> ORGANISM: Cucurbita maxima

<400> SEQUENCE: 45
agatgtccgt cactcttcag                                          20

<210> SEQ ID NO 46
<211> LENGTH: 21
<212> TYPE: DNA
<213> ORGANISM: Cucurbita maxima

<400> SEQUENCE: 46
agagaaagtc taaaagagag a                                        21

<210> SEQ ID NO 47
<211> LENGTH: 21
<212> TYPE: DNA
<213> ORGANISM: Cucurbita maxima

<400> SEQUENCE: 47
agaacattga atctgagcga a                                        21

<210> SEQ ID NO 48
<211> LENGTH: 21
<212> TYPE: DNA
<213> ORGANISM: Cucurbita maxima

<400> SEQUENCE: 48
agtcggaagt tgagtacggt a                                        21

<210> SEQ ID NO 49
<211> LENGTH: 21
<212> TYPE: DNA
<213> ORGANISM: Cucurbita maxima

<400> SEQUENCE: 49
agtttacgac atgactttac a                                        21

<210> SEQ ID NO 50
<211> LENGTH: 22
<212> TYPE: DNA
<213> ORGANISM: Cucurbita maxima

<400> SEQUENCE: 50
agcggtgacg atagtttgat ct                                       22

<210> SEQ ID NO 51
<211> LENGTH: 23

```
<212> TYPE: DNA
<213> ORGANISM: Cucurbita maxima

<400> SEQUENCE: 51
actctttcgc aatagtacca act                                            23

<210> SEQ ID NO 52
<211> LENGTH: 21
<212> TYPE: DNA
<213> ORGANISM: Cucurbita maxima

<400> SEQUENCE: 52
catcttgctg ccaaacatgg a                                              21

<210> SEQ ID NO 53
<211> LENGTH: 21
<212> TYPE: DNA
<213> ORGANISM: Cucurbita maxima

<400> SEQUENCE: 53
catcgatgac ttgtgcggcg c                                              21

<210> SEQ ID NO 54
<211> LENGTH: 21
<212> TYPE: DNA
<213> ORGANISM: Cucurbita maxima

<400> SEQUENCE: 54
cagattgcaa gttttggtcg a                                              21

<210> SEQ ID NO 55
<211> LENGTH: 21
<212> TYPE: DNA
<213> ORGANISM: Cucurbita maxima

<400> SEQUENCE: 55
ctactgtcat caagagtacg c                                              21

<210> SEQ ID NO 56
<211> LENGTH: 24
<212> TYPE: DNA
<213> ORGANISM: Cucurbita maxima

<400> SEQUENCE: 56
ctgacaagta aaggacgttg aaag                                           24

<210> SEQ ID NO 57
<211> LENGTH: 19
<212> TYPE: DNA
<213> ORGANISM: Cucurbita maxima

<400> SEQUENCE: 57
ctgcgaatcc acccatcga                                                 19

<210> SEQ ID NO 58
<211> LENGTH: 22
<212> TYPE: DNA
<213> ORGANISM: Cucurbita maxima

<400> SEQUENCE: 58
ctctatcacg atgtaaagga ag                                             22

<210> SEQ ID NO 59
```

-continued

```
<211> LENGTH: 21
<212> TYPE: DNA
<213> ORGANISM: Cucurbita maxima

<400> SEQUENCE: 59
cgcctgagta gaaaggtgag a                                              21

<210> SEQ ID NO 60
<211> LENGTH: 21
<212> TYPE: DNA
<213> ORGANISM: Cucurbita maxima

<400> SEQUENCE: 60
cgatctcatt atttgctgcg a                                              21

<210> SEQ ID NO 61
<211> LENGTH: 21
<212> TYPE: DNA
<213> ORGANISM: Cucurbita maxima

<400> SEQUENCE: 61
cgtcgcacaa gtcatcgatg a                                              21

<210> SEQ ID NO 62
<211> LENGTH: 21
<212> TYPE: DNA
<213> ORGANISM: Cucurbita maxima

<400> SEQUENCE: 62
cgacatcgac caagaacttg a                                              21

<210> SEQ ID NO 63
<211> LENGTH: 21
<212> TYPE: DNA
<213> ORGANISM: Cucurbita maxima

<400> SEQUENCE: 63
gagacaggtt gttggatttg a                                              21

<210> SEQ ID NO 64
<211> LENGTH: 22
<212> TYPE: DNA
<213> ORGANISM: Cucurbita maxima

<400> SEQUENCE: 64
gactctaagg gcgaaaataa aa                                             22

<210> SEQ ID NO 65
<211> LENGTH: 20
<212> TYPE: DNA
<213> ORGANISM: Cucurbita maxima

<400> SEQUENCE: 65
tccaattgaa atgtcatctc                                                20

<210> SEQ ID NO 66
<211> LENGTH: 21
<212> TYPE: DNA
<213> ORGANISM: Cucurbita maxima

<400> SEQUENCE: 66
gcgctctgac acacaaacca a                                              21
```

```
<210> SEQ ID NO 67
<211> LENGTH: 22
<212> TYPE: DNA
<213> ORGANISM: Cucurbita maxima

<400> SEQUENCE: 67
ctcgacccag acatgatgtc ag                                      22

<210> SEQ ID NO 68
<211> LENGTH: 22
<212> TYPE: DNA
<213> ORGANISM: Cucurbita maxima

<400> SEQUENCE: 68
tgcgctctga cacacaaacc aa                                      22

<210> SEQ ID NO 69
<211> LENGTH: 23
<212> TYPE: DNA
<213> ORGANISM: Cucurbita maxima

<400> SEQUENCE: 69
ccggtcacat acgataagtg gaa                                     23

<210> SEQ ID NO 70
<211> LENGTH: 21
<212> TYPE: DNA
<213> ORGANISM: Cucurbita maxima

<400> SEQUENCE: 70
tctcaaggct gttgacatgg a                                       21

<210> SEQ ID NO 71
<211> LENGTH: 21
<212> TYPE: DNA
<213> ORGANISM: Cucurbita maxima

<400> SEQUENCE: 71
ttgacatcat gtctgggtcg g                                       21

<210> SEQ ID NO 72
<211> LENGTH: 22
<212> TYPE: DNA
<213> ORGANISM: Cucurbita maxima

<400> SEQUENCE: 72
ctactcgacc cagacatgat gt                                      22

<210> SEQ ID NO 73
<211> LENGTH: 22
<212> TYPE: DNA
<213> ORGANISM: Cucurbita maxima

<400> SEQUENCE: 73
tggagaacga cgcgaggttc aa                                      22

<210> SEQ ID NO 74
<211> LENGTH: 23
<212> TYPE: DNA
<213> ORGANISM: Cucurbita maxima

<400> SEQUENCE: 74
taccgatcac atacgatacg tgg                                     23
```

```
<210> SEQ ID NO 75
<211> LENGTH: 21
<212> TYPE: DNA
<213> ORGANISM: Cucurbita maxima

<400> SEQUENCE: 75
caggcctcct aggaatactc g                                        21

<210> SEQ ID NO 76
<211> LENGTH: 20
<212> TYPE: DNA
<213> ORGANISM: Cucurbita maxima

<400> SEQUENCE: 76
gaagggtatt cagcaggtga                                          20

<210> SEQ ID NO 77
<211> LENGTH: 20
<212> TYPE: DNA
<213> ORGANISM: Cucurbita maxima

<400> SEQUENCE: 77
aaaagaaggt cgaaagaaga                                          20

<210> SEQ ID NO 78
<211> LENGTH: 21
<212> TYPE: DNA
<213> ORGANISM: Cucurbita maxima

<400> SEQUENCE: 78
ttcaactcgc ccatgaatta a                                        21

<210> SEQ ID NO 79
<211> LENGTH: 20
<212> TYPE: DNA
<213> ORGANISM: Cucurbita maxima

<400> SEQUENCE: 79
gaggggagtg ggacgattcg                                          20

<210> SEQ ID NO 80
<211> LENGTH: 21
<212> TYPE: DNA
<213> ORGANISM: Cucurbita maxima

<400> SEQUENCE: 80
cgtgttaatt gatgcattgg g                                        21

<210> SEQ ID NO 81
<211> LENGTH: 22
<212> TYPE: DNA
<213> ORGANISM: Cucurbita maxima

<400> SEQUENCE: 81
tcgtgacact tcttctttcg ac                                       22

<210> SEQ ID NO 82
<211> LENGTH: 22
<212> TYPE: DNA
<213> ORGANISM: Cucurbita maxima

<400> SEQUENCE: 82
cgcagcccgt gcggatctat gg                                       22
```

<210> SEQ ID NO 83
<211> LENGTH: 22
<212> TYPE: DNA
<213> ORGANISM: Cucurbita maxima

<400> SEQUENCE: 83
agagtacaca gtacgttgac ga                    22

<210> SEQ ID NO 84
<211> LENGTH: 23
<212> TYPE: DNA
<213> ORGANISM: Cucurbita maxima

<400> SEQUENCE: 84
ggcaagagta caccgtacgt tga                   23

<210> SEQ ID NO 85
<211> LENGTH: 20
<212> TYPE: DNA
<213> ORGANISM: Cucurbita maxima

<400> SEQUENCE: 85
ggatctatgg aaagaaggtc                       20

<210> SEQ ID NO 86
<211> LENGTH: 22
<212> TYPE: DNA
<213> ORGANISM: Cucurbita maxima

<400> SEQUENCE: 86
catagatccg cacgggctgc gg                    22

<210> SEQ ID NO 87
<211> LENGTH: 23
<212> TYPE: DNA
<213> ORGANISM: Cucurbita maxima

<400> SEQUENCE: 87
gcgcgattgg ttatctgatt tgt                   23

<210> SEQ ID NO 88
<211> LENGTH: 23
<212> TYPE: DNA
<213> ORGANISM: Cucurbita maxima

<400> SEQUENCE: 88
tggtggcgcg attggttatc tga                   23

<210> SEQ ID NO 89
<211> LENGTH: 23
<212> TYPE: DNA
<213> ORGANISM: Cucurbita maxima

<400> SEQUENCE: 89
ggataaccaa tcgcgccatc gac                   23

<210> SEQ ID NO 90
<211> LENGTH: 23
<212> TYPE: DNA
<213> ORGANISM: Cucurbita maxima

<400> SEQUENCE: 90
gagtgaaaat ggattaacac caa                                              23

<210> SEQ ID NO 91
<211> LENGTH: 20
<212> TYPE: DNA
<213> ORGANISM: Cucurbita maxima

<400> SEQUENCE: 91
ccagggttcg aacccgtgac                                                  20

<210> SEQ ID NO 92
<211> LENGTH: 21
<212> TYPE: DNA
<213> ORGANISM: Cucurbita maxima

<400> SEQUENCE: 92
cggtggcgcg attggttatc t                                                21

<210> SEQ ID NO 93
<211> LENGTH: 22
<212> TYPE: DNA
<213> ORGANISM: Cucurbita maxima

<400> SEQUENCE: 93
gtgaccgtgg agttgaaatg ga                                               22

<210> SEQ ID NO 94
<211> LENGTH: 24
<212> TYPE: DNA
<213> ORGANISM: Cucurbita maxima

<400> SEQUENCE: 94
cagataacca atagcgccac cgac                                             24

<210> SEQ ID NO 95
<211> LENGTH: 23
<212> TYPE: DNA
<213> ORGANISM: Cucurbita maxima

<400> SEQUENCE: 95
gacgctggtg ttgaactggt tta                                              23

<210> SEQ ID NO 96
<211> LENGTH: 23
<212> TYPE: DNA
<213> ORGANISM: Cucurbita maxima

<400> SEQUENCE: 96
cgctggtgtt gaactggttt acg                                              23

<210> SEQ ID NO 97
<211> LENGTH: 21
<212> TYPE: DNA
<213> ORGANISM: Cucurbita maxima

<400> SEQUENCE: 97
gacgctggtg ttgaactggt t                                                21

<210> SEQ ID NO 98
<211> LENGTH: 23
<212> TYPE: DNA
<213> ORGANISM: Cucurbita maxima

<400> SEQUENCE: 98

```
gttggtgttg aactggttta caa                                            23

<210> SEQ ID NO 99
<211> LENGTH: 20
<212> TYPE: DNA
<213> ORGANISM: Cucurbita maxima

<400> SEQUENCE: 99
aaccagttca acaccagcgt                                                20

<210> SEQ ID NO 100
<211> LENGTH: 20
<212> TYPE: DNA
<213> ORGANISM: Cucurbita maxima

<400> SEQUENCE: 100
gctggtgttg aactggttta                                                20

<210> SEQ ID NO 101
<211> LENGTH: 24
<212> TYPE: DNA
<213> ORGANISM: Cucurbita maxima

<400> SEQUENCE: 101
tcattgtttg gttgtaaacc agtt                                           24

<210> SEQ ID NO 102
<211> LENGTH: 23
<212> TYPE: DNA
<213> ORGANISM: Cucurbita maxima

<400> SEQUENCE: 102
aaccagttca ataccagcgt cac                                            23

<210> SEQ ID NO 103
<211> LENGTH: 23
<212> TYPE: DNA
<213> ORGANISM: Cucurbita maxima

<400> SEQUENCE: 103
gtaaaccagt tcaacactag cgt                                            23

<210> SEQ ID NO 104
<211> LENGTH: 23
<212> TYPE: DNA
<213> ORGANISM: Cucurbita maxima

<400> SEQUENCE: 104
tgtttggttg taaaccagtt caa                                            23

<210> SEQ ID NO 105
<211> LENGTH: 23
<212> TYPE: DNA
<213> ORGANISM: Cucurbita maxima

<400> SEQUENCE: 105
ttggtgttga atggtttac aac                                             23

<210> SEQ ID NO 106
<211> LENGTH: 24
<212> TYPE: DNA
<213> ORGANISM: Cucurbita maxima
```

-continued

```
<400> SEQUENCE: 106
acaaattggg ggagggatt acaa                                            24

<210> SEQ ID NO 107
<211> LENGTH: 25
<212> TYPE: DNA
<213> ORGANISM: Cucurbita maxima

<400> SEQUENCE: 107
ctggtttaca accaaacaat gaaac                                          25

<210> SEQ ID NO 108
<211> LENGTH: 22
<212> TYPE: DNA
<213> ORGANISM: Cucurbita maxima

<400> SEQUENCE: 108
tcggtatttg taatcctctt cc                                             22

<210> SEQ ID NO 109
<211> LENGTH: 23
<212> TYPE: DNA
<213> ORGANISM: Cucurbita maxima

<400> SEQUENCE: 109
tggtgttgag ctggtttaca acc                                            23

<210> SEQ ID NO 110
<211> LENGTH: 22
<212> TYPE: DNA
<213> ORGANISM: Cucurbita maxima

<400> SEQUENCE: 110
ctggtttaca accaaacaat ga                                             22

<210> SEQ ID NO 111
<211> LENGTH: 24
<212> TYPE: DNA
<213> ORGANISM: Cucurbita maxima

<400> SEQUENCE: 111
agcgcagcgg tttcattgtt tggt                                           24

<210> SEQ ID NO 112
<211> LENGTH: 24
<212> TYPE: DNA
<213> ORGANISM: Cucurbita maxima

<400> SEQUENCE: 112
tcaacaccag cgtcacgagt tcga                                           24

<210> SEQ ID NO 113
<211> LENGTH: 22
<212> TYPE: DNA
<213> ORGANISM: Cucurbita maxima

<400> SEQUENCE: 113
caccagcgtc acgggttcgt ga                                             22

<210> SEQ ID NO 114
<211> LENGTH: 22
<212> TYPE: DNA
<213> ORGANISM: Cucurbita maxima
```

-continued

```
<400> SEQUENCE: 114
ctagtttaca accaaacaat ga                                              22

<210> SEQ ID NO 115
<211> LENGTH: 23
<212> TYPE: DNA
<213> ORGANISM: Cucurbita maxima

<400> SEQUENCE: 115
tgtttggttg taaaccagtt caa                                             23

<210> SEQ ID NO 116
<211> LENGTH: 22
<212> TYPE: DNA
<213> ORGANISM: Cucurbita maxima

<400> SEQUENCE: 116
ttcgaactcg tgacgctggt gt                                              22

<210> SEQ ID NO 117
<211> LENGTH: 24
<212> TYPE: DNA
<213> ORGANISM: Cucurbita maxima

<400> SEQUENCE: 117
catcgaaccc gtgacgctag tgtt                                            24

<210> SEQ ID NO 118
<211> LENGTH: 21
<212> TYPE: DNA
<213> ORGANISM: Cucurbita maxima

<400> SEQUENCE: 118
gtttcattat ttggttgtaa a                                               21

<210> SEQ ID NO 119
<211> LENGTH: 22
<212> TYPE: DNA
<213> ORGANISM: Cucurbita maxima

<400> SEQUENCE: 119
tggttgtaaa ccagttcaac ac                                              22

<210> SEQ ID NO 120
<211> LENGTH: 22
<212> TYPE: DNA
<213> ORGANISM: Cucurbita maxima

<400> SEQUENCE: 120
tgttgaactg gtttacaacc aa                                              22

<210> SEQ ID NO 121
<211> LENGTH: 21
<212> TYPE: DNA
<213> ORGANISM: Cucurbita maxima

<400> SEQUENCE: 121
tcgaaaccgt gacgctggtg t                                               21

<210> SEQ ID NO 122
<211> LENGTH: 22
<212> TYPE: DNA
```

```
<213> ORGANISM: Cucurbita maxima

<400> SEQUENCE: 122
cgcagtgatt tcattgtttg gt                                              22

<210> SEQ ID NO 123
<211> LENGTH: 24
<212> TYPE: DNA
<213> ORGANISM: Cucurbita maxima

<400> SEQUENCE: 123
tgtttggttg taaatcagtt caac                                            24

<210> SEQ ID NO 124
<211> LENGTH: 23
<212> TYPE: DNA
<213> ORGANISM: Cucurbita maxima

<400> SEQUENCE: 124
gaggattaca ataccgactc ttc                                             23

<210> SEQ ID NO 125
<211> LENGTH: 20
<212> TYPE: DNA
<213> ORGANISM: Cucurbita maxima

<400> SEQUENCE: 125
tgacagaaga gagtgagcac                                                 20

<210> SEQ ID NO 126
<211> LENGTH: 21
<212> TYPE: DNA
<213> ORGANISM: Cucurbita maxima

<400> SEQUENCE: 126
tttggattga agggagctct a                                               21

<210> SEQ ID NO 127
<211> LENGTH: 22
<212> TYPE: DNA
<213> ORGANISM: Cucurbita maxima

<400> SEQUENCE: 127
tcaagctgcc agcatgatct ga                                              22

<210> SEQ ID NO 128
<211> LENGTH: 20
<212> TYPE: DNA
<213> ORGANISM: Cucurbita maxima

<400> SEQUENCE: 128
gattgagccg cgccaatatc                                                 20
```